(12) United States Patent
Biedermann et al.

(10) Patent No.: US 6,506,572 B2
(45) Date of Patent: Jan. 14, 2003

(54) INHIBITORS OF CELLULAR NIACINAMIDE MONONUCLEOTIDE FORMATION AND THEIR USE IN CANCER THERAPY

(75) Inventors: Elfi Biedermann, Vaterstetten (DE); Rolf Eisenburger, Kirchseeon (DE); Max Hasmann, Neuried (DE); Roland Löser, Feldafing (DE); Benno Rattel, Munich (DE); Friedemann Reiter, Putzbrunn (DE); Barbara Schein, Neufahrn (DE); Isabel Schemainda, Munich (DE); Michael Schulz, Aschheim (DE); Klaus Seibel, Gräfelfing- (DE); Klaus Vogt, Munich (DE); Katja Wosikowski, Poing (DE)

(73) Assignee: Klinge Pharma GmbH, Munich (DE)

( * ) Notice: Subject to any disclaimer, the term of this patent is extended or adjusted under 35 U.S.C. 154(b) by 0 days.

(21) Appl. No.: 09/935,772

(22) Filed: Aug. 23, 2001

(65) Prior Publication Data

US 2002/0160968 A1 Oct. 31, 2002

Related U.S. Application Data

(63) Continuation of application No. PCT/EP00/01628, filed on Feb. 28, 2000.

(30) Foreign Application Priority Data

Feb. 26, 1999 (EP) .............................. 99103814

(51) Int. Cl.[7] .............................. C12Q 1/48; C12Q 1/00; C12Q 1/02

(52) U.S. Cl. .............................. 435/15; 435/4; 435/29; 424/573; 424/172.1; 424/174

(58) Field of Search .............................. 435/15, 4, 29; 424/573, 172.1, 174

(56) References Cited

U.S. PATENT DOCUMENTS

| 4,283,541 A | 8/1981 | Shroff et al. ................. 546/336 |
| 5,169,856 A | 12/1992 | Goto et al. ................... 514/331 |
| 5,260,323 A | 11/1993 | Baader et al. ................. 514/356 |
| 5,326,772 A | 7/1994 | Klemm et al. ................. 514/318 |

FOREIGN PATENT DOCUMENTS

| CA | 2085954 | 6/1993 |
| DE | 4020570 | 1/1992 |
| EP | 048045 | 3/1982 |
| EP | 210782 | 2/1987 |
| EP | 271023 | 6/1988 |
| EP | 330026 | 8/1989 |
| EP | 343307 | 11/1989 |
| EP | 416581 | 3/1991 |
| EP | 471236 | 2/1992 |
| EP | 479601 | 4/1992 |
| EP | 522606 | 1/1993 |
| EP | 530444 | 3/1993 |
| EP | 548883 | 6/1993 |

(List continued on next page.)

OTHER PUBLICATIONS

Ross, "The Preparation of Some 4–Substituted Nicotinic Acids and Nicotinamides" J. Chem. Soc. (C), 1966, 1816–1820.

*Primary Examiner*—Louise N. Leary
(74) *Attorney, Agent, or Firm*—Fitch, Even, Tabin & Flannery

(57) ABSTRACT

New biologically active compounds are described which inhibit the cellular formation of niacinamide mononucleotide, and essential intermediate of the NAD(P) biosynthesis in the cell. These compounds can represent the active ingredient of a pharmaceutical composition for the treatment of cancers, leukaemias or for immunosuppression. Furthermore, screening methods are described as a tool for detecting the above active compounds, and for examination of a given cell type for its dependency on niacinamide as a precursor for NAD synthesis.

25 Claims, 28 Drawing Sheets

FOREIGN PATENT DOCUMENTS

| | | |
|---|---|---|
| EP | 512902 | 4/1994 |
| EP | 428434 | 5/1994 |
| EP | 1031564 A1 * | 2/1999 |
| GB | 2304714 | 11/1998 |
| WO | WO89/07443 | 8/1989 |
| WO | WO91/15484 | 10/1991 |
| WO | WO91/15485 | 10/1991 |
| WO | WO93/14113 | 7/1993 |
| WO | WO95/10514 | 4/1995 |
| WO | WO95/10515 | 4/1995 |
| WO | WO95/10516 | 4/1995 |
| WO | WO95/24894 | 9/1995 |
| WO | WO93/14070 | 9/1996 |
| WO | WO96/31478 | 10/1996 |
| WO | WO94/01402 | 3/1997 |
| WO | WO93/13083 | 4/1997 |
| WO | WO97/48397 | 12/1997 |
| WO | WO97/48696 | 12/1997 |
| WO | WO96/31477 | 1/1998 |
| WO | WO97/48695 | 1/1998 |
| WO | WO99/31060 | 6/1999 |
| WO | WO99/31063 | 6/1999 |
| WO | WO99/31064 | 6/1999 |
| WO | WO99/31087 | 6/1999 |

* cited by examiner

- ❶ niacinamide phosphoribosyl transferase
- ❷ niacin phosphoribosyl transferase
- ❸ quinolinic acid phosphoribosyl transferase
- ❹ NAD pyrophosphorylase
- ❺ NAD synthetase
- ❻ NAD kinase $PP_i$: inorganic phosphate, ADP: adenosine diphosphate, ATP: adenosine triphosphate Substances:
- ─o─ 6-Aminonicotinamide $1\times10^{-4}$ M
- ─△─ 6-Aminonicotinamide $3\times10^{-5}$ M
- ─×─ 6-Aminonicotinamide $1\times10^{-5}$ M
- ─◇─ 6-Aminonicotinamide $3\times10^{-6}$ M
- ─✻─ 6-Aminonicotinamide $1\times10^{-6}$ M
- ─+─ 6-Aminonicotinamide $3\times10^{-7}$ M Reference: ─▲─ x242 $3\times10^{-6}$ M ─●─ Control

INHIBITORS OF CELLULAR NIACINAMIDE MONONUCLEOTIDE FORMATION AND THEIR USE IN CANCER THERAPY

This is a continuation, of prior application number PCT/EP00/01628, filed Feb. 28, 2000 and designation U.S., which is hereby incorporated herein by reference in its entirety.

FIELD OF THE INVENTION

The present invention relates to new biologically active compounds which inhibit the cellular formation of niacinamide mononucleotide, which is one of the essential intermediates in the NAD(P) biosynthesis in the cell. The invention further concerns pharmaceutical compositions containing these compounds and their use, especially in the treatment of cancers, leukaemias or for immunosuppression. The invention also provides screening methods as a tool for detecting the above active compounds, and for examination of cell types with respect to their NAD(P) synthesis pathway.

TECHNICAL BACKGROUND OF THE INVENTION

NAD is synthesized in mammalian cells by three different pathways starting either from tryptophan via quinoline acid, from niacin (also referred to as nicotinic acid) or from niacinamide (also referred to as nicotinamide), as shown in FIG. 1.

The addition of a phosphoribosyl moiety results in the formation of the corresponding mononucleotides, niacin mononucleotide (dNAM) and niacinamide mononucleotide (NAM). Quinoline acid is utilized in a reaction with phosphoribosyl pyrophosphate (PRPP) to form niacin mononucleotide (dNAM). The enzyme catalyzing this reaction, quinoline acid phosphoribosyl transferase (❸), is found in liver, kidney and brain.

Niacin reacts with PRPP to form niacin mononucleotide (dNAM) The enzyme catalyzing this reaction is niacin phosphoribosyl transferase (❷) and is widely distributed in various tissues. Both pathways starting either from tryptophan or from niacin as NAD precursors merge at the stage of the niacin mononucleotide formalin.

Niacinamide reacts with PRPP to give niacinamide mononucleotide (NAM). The enzyme that catalyses this reaction is niacinamide phosphoribosyl transferase (z,902 ). This enzyme is specific for niacinamide and is entirely distinct from niacin phosphoribosyl transferase (❷). It is also widely distributed in various tissues.

The subsequent addition of adenosine monophosphate to the mononucleotides results in the formation of the corresponding dinucleotides: Niacin mononucleotide and niacinamide mononucleotide react with ATP to yield niacin adenine dinucleotide (dNAD) and niacinamide adenine dinucleotide (NAD), respectively. Both reactions, albeit taking place on two different pathways, are catalyzed by the same enzyme, NAD pyrophosphorylase (❹).

A further amidation step is needed to convert niacin adenine dinucleotide (dNAD) to niacinamide adenine dinucleotide (NAD) The enzyme which catalyses this reaction is NAD synthetase (❺). NAD is the immediate precursor of niacinamide adenine dinucleotide phosphate (NADP). The reaction is catalyzed by NAD kinase (❻). For details see, for example, Cory, J. G. Purine and pyrimidine nucleotide metabolism. In: Textbook of Biochemistry and Clinical Correlations, $3^{rd}$ edition, ed. Devlin, T., Wiley Brisbane 1992, pp 529–574.

Normal cells can typically utilize both precursors niacin and niacinamide for NAD(P) synthesis, and in many cases additionally tryptophan or its metabolites, which has been demonstrated for various normal tissues: Accordingly, Murine glial cells (cortex and hippocampus=brain) use: niacin, niacinamide, and quinoline acid (Grant et al. (1998), J. Neurochem. 70: 1759–1763). Human lymphocytes use niacin and niacinamide (Carson et al. (1987), J. Immunol. 138: 1904–1907; Berger et al. (1982), Exp. Cell Res. 137: 79–88). Rat liver cells use niacin, niacinamide and tryptophan (Yamada et al. (1983), Internat. J. Vit. Nutr. Res. 53: 184–191; Shin et al. (1995), Internat. J. Vit. Nutr. Res. 65: 143–146; Dietrich (1971) , Methods Enzymol. 18B: 144–149). Human erythrocytes use niacin and niacinamide (Rocchigiani et al. (1991), Purine and pyrimidine metabolism in man VII, Part B, ed. Harkness et al., Plenum Press, New York, pp 337–340. Leukocytes of guinea pigs use niacin (Flechner et al. (1970), Life Science. 9: 153–162).

NAD(P) is involved in a variety of biochemical reactions which are vital to the cell and have therefore been thoroughly investigated. This key function of NAD(P) has evoked also some investigations in the past on the role of this compound for the development and growth of tumors, and as to what the NAD(P) metabolism could also be utilized to combat tumors. Indeed, compounds aiming at the treatment of tumor diseases have been described which involve—concomitantly to other effects—also the decrease of NAD(P) levels in the cell. However, these compounds primarily act by initiating the cellular synthesis of dinucleotide derivatives which structurally deviate from natural NAD. The biochemical consequences of this approach and the putative mechanisms of the resulting cell-damage are, therefore, manifold as outlined in the Table 1.

| Compounds | Mode of action | Ref. |
| --- | --- | --- |
| 6-amino-nicotin-amide | Primary mechanism of action: Synthesis of 6-amino-AND(P), a competitive inhibitor of AND(P)-requiring enzymes, especially of 6-phosphogluconate dehydrogenase, an enzyme of the pentose-phosphate-pathway which provides the precursor of the nucleotide biosynthesis ribose-5-phosphate. Resulting biochemical effects in the cell: Inhibition of purine nucleotide de novo synthesis from [$^{14}$C]glycine. Decrease of intracellular purine (ATP, GTP) and pyrimidine (UTP, CTP) nucleotide pools resulting in the inhibition of DNA and RNA synthesis. Inhibition of PARP (an enzyme involved in the DNA repair). Reduction of the ATP to ADP ratio. Depression of intracellular AND concentration. | 1, 2, 3 |
| tiazofurin, selena-zofurin | Primary mechanism of action: Synthesis of the AND analogs TAD, SAD which are potent inhibitors of inosine monophosphate dehydrogenase, an enzyme involved in the synthesis of purine nucleotides. Resulting biochemical effects in the cell: Depletion of GMP and accumulation of IMP resulting in an inhibition of DNA and RNA synthesis. Stimulation of AND synthesis after short exposure (<24 h). Inhibition of AND synthesis after prolonged exposure (>24 h), probably due to negative feedback | 2, 4, 5 |

-continued

| Compounds | Mode of action | Ref. |
| --- | --- | --- |
| | inhibition of AND synthesis by TAD/SAD which accumulate in the cell. | |
| azaserine, 6-diazo-5-oxo-L-norleucine | Primary mechanism of action: Analogs of glutamine which block the enzymatic transfer of the amido group of glutamine. Resulting biochemical effects in the cell: Inhibition of IMP synthesis resulting in an inhibition of DNA and RNA synthesis. Inhibition of AND synthesis from the precursor niacin at the following step: dNAD → AND Mutagen, cancerogen. | 6, 7 |
| DNA-interacting compounds (e.g. N-methyl-N'-nitro-N-nitroso-guanidine) | Primary mechanism of action: Induction of DNA strand breaks. Resulting biochemical effects in the cell: Multiple consequences of DNA damage. Activation of the DNA repair enzyme PARP resulting in a decline of the intracellular AND content, since the substrate of PARP is AND. Mutagen, cancerogen. | 4, 8, 9, 10 |

Abbreviations:
PARP, poly(ADP-ribose) polymerase;
AND, niacinamide adenine dinucleotide;
NADP, niacinamide adenine dinucleotide phosphate;
dNAD, niacin adenine dinucleotide;
ATP, adenosine triphosphate;
ADP, adenosine diphosphate;
GTP, guanosine triphosphate;
GMP, guanosine monophosphate;
UTP, uridine triphosphate;
CTP, cytosine trisphosphate;
DNA, desoxyribonucleic acid;
RNA, ribonucteic acid;
TAD, tiazofurin adenine dinucleotide;
SAD, selenazofurin adenine dinucleotide;
IMP, inosine monophosphate.

It is therefore not possible to make any predictions from these data on the biological effects of a primary and specific inhibition of the NAD biosynthesis in various cell types. In particular, it remains completely speculative whether this mechanism may be advantageous over the above utilization or dinucleotide derivatives with regard to tumor selectivity of the cell damaging effect, the most important feature of a potential drug for tumor therapy.

JP-459555, published in 1970, describes the extraction of a structurally unknown constituent from potatoes, baker's yeast and bovine blood which inhibits respiration of tumor cells and NAD synthesis of erythrocytes. The inventors propose the use of this constituent for tumor therapy. However, the data presented in JP-459555 are far from making it clear or even probable that inhibition of NAD synthesis is useful for the therapy of cancer. The inventors rather come to the conclusion that the biological activity of the compound is multifaceted and not limited merely to the phenomenon of inhibition of NAD biosynthesis. In a study published later by the same research group (A. Kizu: Kyoto Furitsu Ika Daigaku Zasshi 80, pp. 14–24, 1971) it was shown that the extracted compounds (derivatives of glucose) inhibit respiration and glycolysis in tumor cells already within a few minutes in addition to inhibition of NAD synthesis. In fact, tumor cells treated with the extract for only 20 min suffered from such heavy damage that they did not grow in the abdominal cavity of mice in contrast to untreated control cells. In contrast to this finding, the present inventors have observed that compounds which promptly and selectively inhibit NAD synthesis in the cell exert a deleterious effect on tumor cells only after an exposure for 3–4 days, whereas an exposure for 20 min is completely ineffective irrespective of the concentration employed. Thus, it is very unlikely that it is NAD biosynthesis inhibition by which the extract disclosed in JP-459555 damages tumor cells. It is rather assumed that other mechanisms are primarily responsible for the cell death, while the reduction of the NAD levels is a secondary effect due to the general damage to the cell. The prompt deleterious effect on tumor cells as produced by this extract is, therefore, obviously due to a inhibition of cell respiration.

Also, the tumor preference of the cell killing effect of the extract, as described in JP-459555, can easily be explained by a characteristic feature of the respiration inhibiting effect of the extract, as this effect is marked in tumor cells but absent in liver cells. (FIG. 2 in A. Kizu). Thus, clearly JP-459555 did not disclose any means to affect tumor cells by NAD synthesis inhibition.

It was also known that DNA damaging cytotoxic compounds initiate a decrease of the cellular concentration of NAD. Some authors assumed that lowering of cellular NAD levels, with a resulting shortage of ATP within the cell, may play a role in the mechanism of cell death produced by these compounds (Daniel S. Martin and Gary K. Schwartz, Oncology Research, Vol. 9, pp. 1–5, 1997). The effect of these compounds on the NAD concentration within the cell results, however, indirectly from an enhanced NAD consumption by enzymes involved in DNA repair (see Table 1).

The primary effect of these compounds, namely damage to the DNA, has many consequences in addition to lowering cellular NAD levels. As known, the DNA is in control of the synthesis of many cellular constituents, like proteins and enzymes, which are of vital importance to the cell. Thus, the consequences of DNA damage are also manifold, lowering of the cellular NAD concentration being only one of them. The efficacy profile of a specific inhibition of the NAD biosynthesis can, therefore, not be concluded from observations made with these compounds.

Just as little information on what can be expected from a specific inhibition of the biosynthesis of NAD gives the symptomatology of niacinamide and niacin deficiency. These vitamins of the B group are precursors of the NAD biosynthesis as outlined above. Long term deficiency of these precursors results in a disease known as pellagra. Main symptoms are alterations of the skin and dementia. This syndrome shows no similarity to the chronic intoxication with any of the compounds discussed above.

WO 97/48695 describes new pyridyl alkane acid amines, methods for their production, medicaments containing these compounds as well as their use, especially in the treatment of tumor conditions and/or as cytostatic agents or as immunosuppressive agents. WO 97/48696 discloses new pyridyl alkene and pyridyl alkine acid amines, methods for their production, medicaments containing these compounds as well as their use, especially in the treatment of tumor conditions and/or as cytostatic agents or as immunosuppressive agents. In WO 97/48397 the use of pyridyl alkane, pyridyl alkene and/or pyridyl alkine acid amines, especially in the treatment of tumor conditions and/or as cytostatic agents or as immunosuppressive agents as well as medicaments with an amount of these compounds in combination with other cytostatic agents or immunosuppressive agents is disclosed. WO 99/31063, published Jun. 24, 1999, describes new piperazinyl-substituted pyridyl-alkane, alkene and alkine carboxamides with a saturated, one or several-fold unsaturated hydrocarbon residue in the carboxylic acid portion, methods for the synthesis of these compounds, medicaments containing these and their production as well as their therapeutic use especially as cytostatic agents and immunosuppresive agents, for example, in the treatment or prevention of various types of tumors and control of immune reactions, for example of autoimmune diseases. WO 99/31060, published Jun. 24, 1999, reports on new piperidinyl-substituted pyridyl-alkane, alkene and alkine carboxamides with a saturated or one or several-fold unsaturated hydrocarbon residue in the carboxylic acid portion, methods for the synthesis of these compounds, medicaments containing these and their production as well as their therapeutic use especially as cytostatic agents and immunosuppresive agents, for example, in the treatment or prevention of various types of tumors and control of immune reactions, for example of autoimmune diseases. New pyridylalkane, alkene and alkine carboxamides substituted with a cyclic imide and with a saturated or one or several-fold unsaturated hydrocarbon residue in the carboxylic acid group, methods for the synthesis of these compounds, medicaments containing these and their production as well as their therapeutic use especially as cytostatic agents and immunosuppresive agents, for example, in the treatment or prevention of various types of tumors inhibition of abnormal cell growth and control of immune reactions, for example of autoimmune diseases is the subject of WO 99/31087, published on Jun. 24, 1999. In WO 99/31064, published on Jun. 24, 1999, new pyridylalkane, alkene and alkine carboxamides substituted with a saturated, one or several-fold unsaturated hydrocarbon residue in the carboxylic acid grouping, methods for the synthesis of these compounds, medicaments containing these and their production as well as their therapeutic use especially as cytostatic agents and immunosuppresive agents, for example, in the treatment or prevention of various types of tumors and control of immune reactions, for example of autoimmune diseases are disclosed. All these applications disclose compounds or the use of compounds which have cytostatic activity and/or are useful in the treatment of tumor conditions, however neither do these applications give any indication that the biosynthesis of NAD is inhibited by these compounds nor do they implicitly disclose these compounds as being specific niacinamide phosphoribosyltransferase (NAPRT) inhibitors.

Thus, in summary, the state of the art does not allow to draw conclusions as to what can be expected from a primary and specific inhibition of the cellular synthesis of NAD because the compounds known to lower the cellular NAD concentration exert other primary effects which may affect cell survival by themselves. There exists no other reliable means to solve this question than the use of a specific inhibitor of NAD synthesis. But no such compound was available in the past.

Morton (R. K. Morton: Nature 181, pp. 540–543, 1958) proposes for human cancer therapy to aim at compounds which inhibit the NAD pyrophosphorylase (Enzyme ❹ in FIG. 1) as the activity of this enzyme was assumed to be the limiting factor of NAD synthesis. Note that the biosynthesis pathway from both niacin and niacinamide, and also from tryptophan would be blocked by an inhibition of the NAD pyrophosphorylase since it acts on a late step of the biosynthesis pathway where the initially separated pathways starting from the different precursors tryptophan, niacin or niacinamide have already been united or are equally affected. No specific inhibitor of this enzyme has been found until now. Thus, no evidence for the correctness of this assumption is available.

DETAILED DESCRIPTION OF THE INVENTION

The present invention is based on the surprising finding that in specific cell types utilization of niacinamide for cellular NAD(P) biosynthesis is of vital importance. Niacin or tryptophan which constitute alternative precursors in many other cell types investigated so far cannot be utilized, or at least not to an extent sufficient for cell survival. Accordingly, the present invention provides for biologically active compounds which inhibit the cellular formation of niacinamide mononucleotide. Compounds having this activity can easily be identified by the screening assay described below (also referred to hereinafter as NAPRT assay). Preferably, the present compounds at concentrations of $\leq 10$ $\mu M$ exhibit an inhibitory activity on cellular NAD biosynthesis from the precursor niacinamide of at least 50%, more preferably at least 80% and most preferably at least 90% in such an assay.

Figure 1:
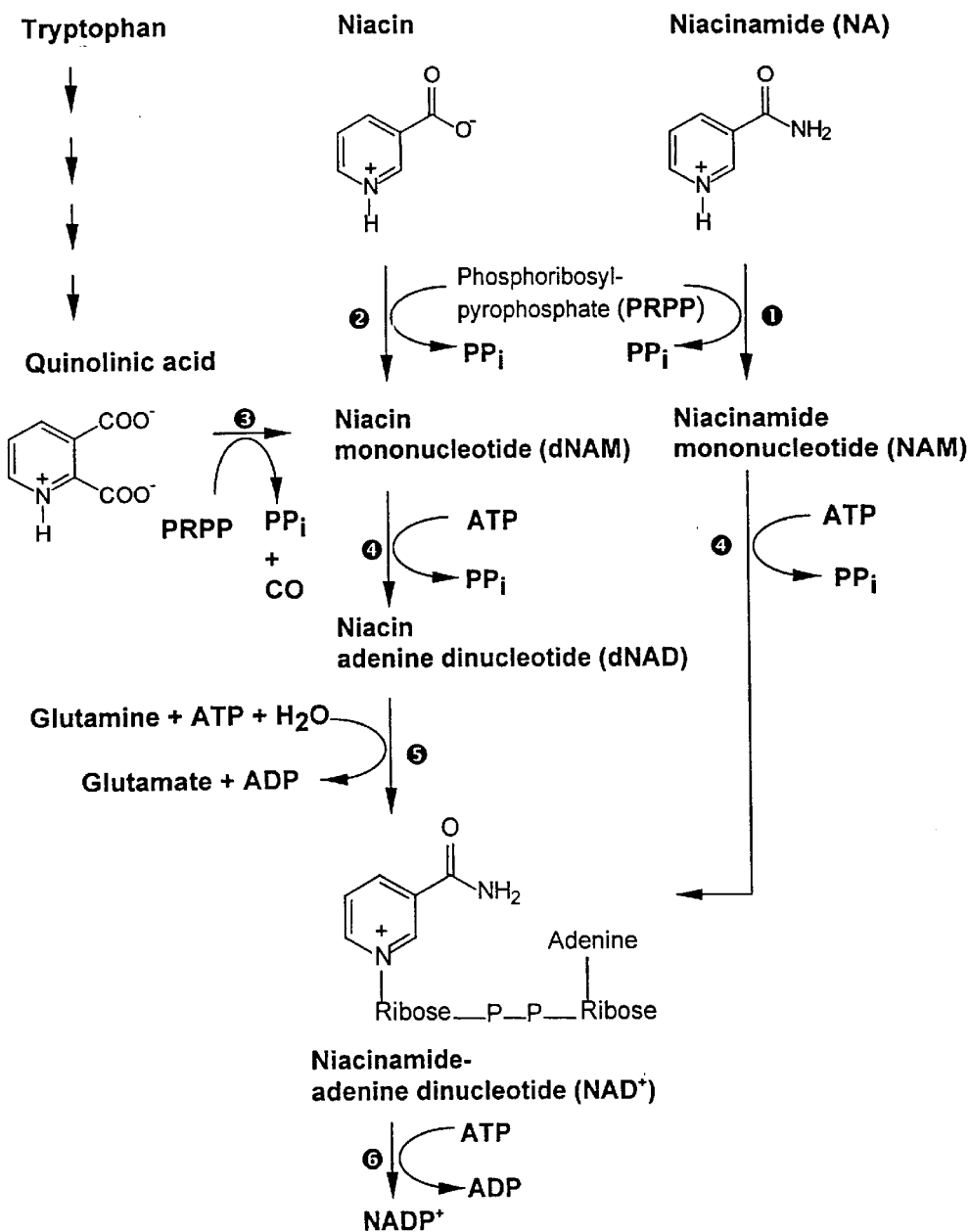
FIG. 1: Biochemical Pathways of $NAD(P)^+$ Biosynthesis
Figure 2:
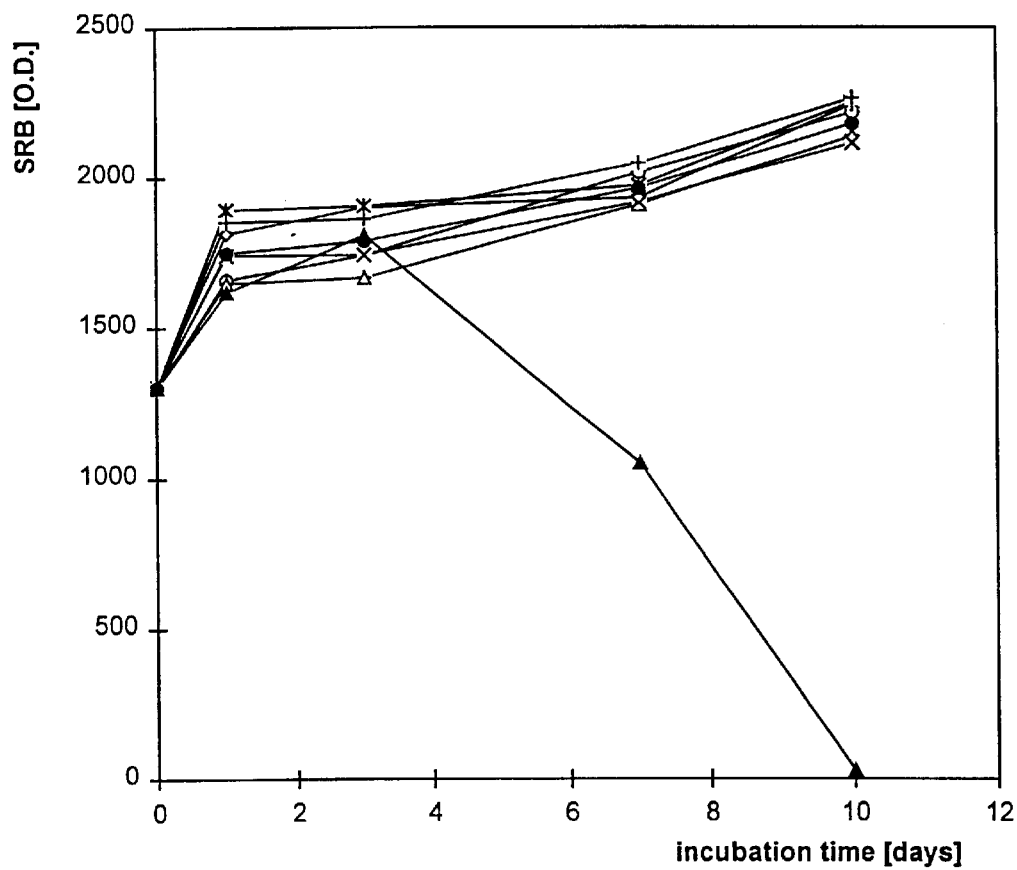
FIG. 2: Time curve of the action of 6-Amino-nicotinamide in different concentrations on the HepG2 cell growth in comparison to a control and an internal standard determined by the SRB assay.
Figure 3:
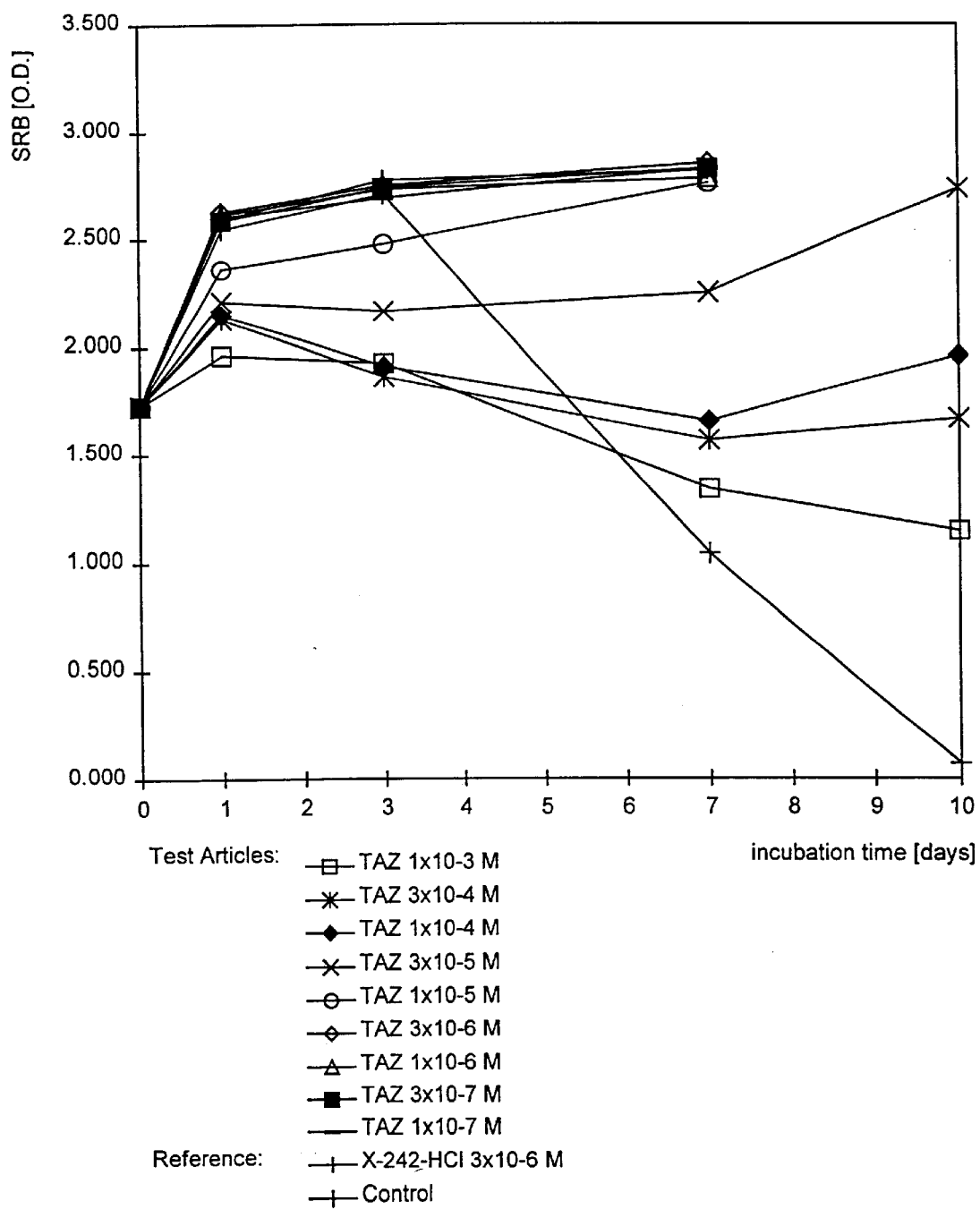
FIG. 3: Time curve of the action of Tiazofurin in different concentrations on the HepG2 cell growth in comparison to a control and an internal standard determined by the SRB assay.
Figure 4:
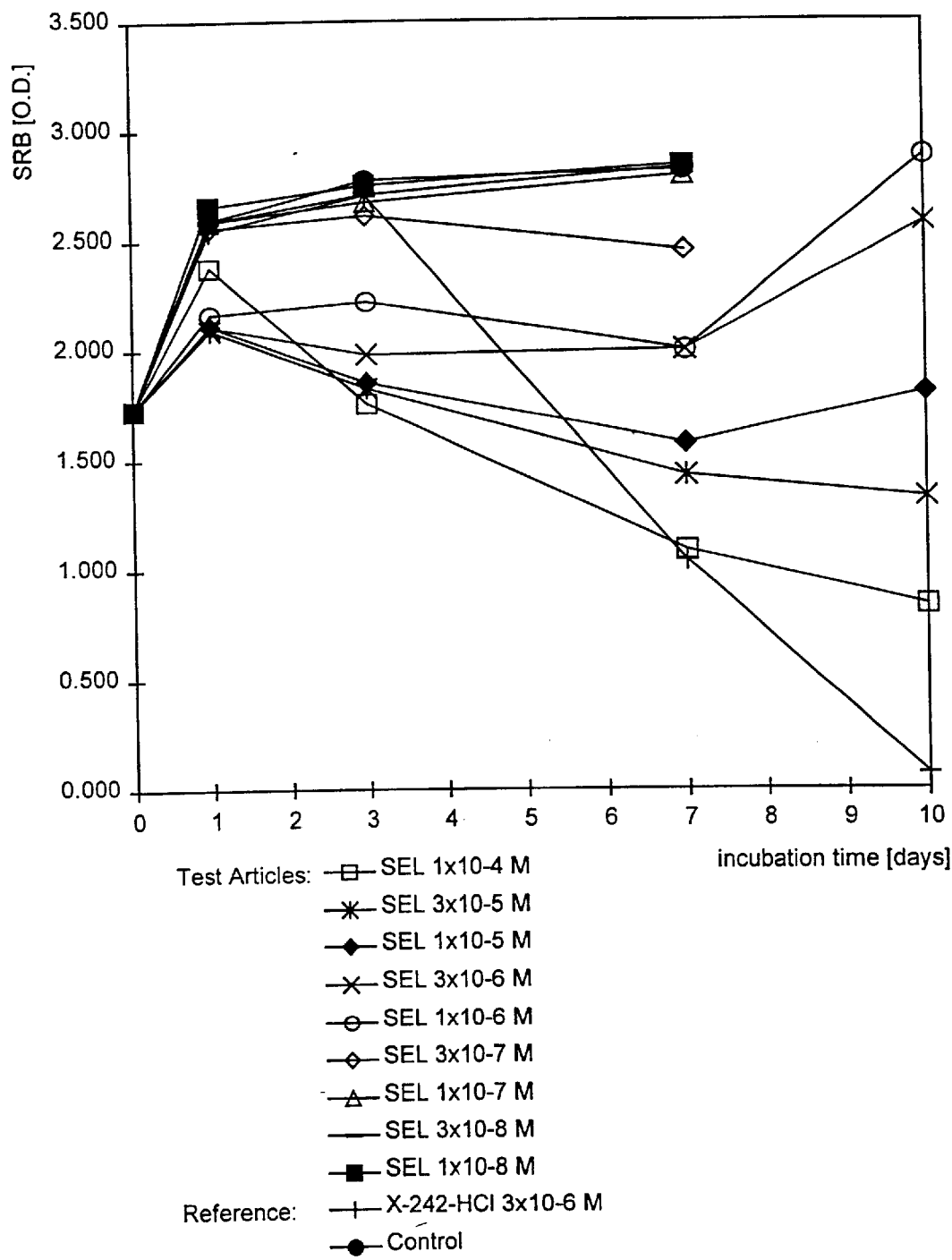
FIG. 4: Time curve of the action of Selenazofurin in different concentrations on the HepG2 cell growth in comparison to a control and an internal standard determined by the SRB assay.

With the compounds of the present invention it is possible for the first time to damage exclusively those cells which mainly use niacinamide as a precursor for NAD biosynthesis saving those cells which are additionally able to synthesize NAD from niacin or tryptophan (FIG. 1). It turned out that by using these compounds many malignant cells are affected while non-malignant cells can be saved. The same applies to certain lymphocytes which play a role in immune reactions. This behavior has not been observed before and is also completely surprising: Neither there was any indication in the prior art nor could it be expected on the basis of the known data that normal somatic cells which can typically use all three kinds of precursors lose their ability to accommodate tryptophan and niacin, or at least they lose the ability to an extent sufficient for cell survival, and become dependent on niacinamide when turning malignant.

Thus, biologically active compounds which selectively block the niacinamide branch of the NAD biosynthesis, i.e. inhibit the formation of niacinamide mononucleotide on the cellular level, would offer a new approach for selective tumor therapy: Malignant cells dependent on niacinamide as a main or sole precursor would suffer from such damage and finally be destroyed due to the inhibition of niacinamide mononucleotide formation and the subsequent NAD(P) depletion. On the other hand, normal somatic cells can compensate for the inhibited niacinamide branch by still utilizing niacin and/or tryptophan as precursors thereby providing sufficient NAD levels to guarantee survival of the cells.

The compounds of this invention are the first which primarily and specifically inhibit the biosynthesis of NAD from niacinamide. Therefore, these compounds can be used as a tool for investigation on the effect of this primary event on the survival of tumor cells and other cells of the body.

Moreover, it was completely surprising that the new specific inhibitors of NAD synthesis via niacinamide which deplete NAD in tumor cells within hours did not quickly kill the cells as shown with the known NAD synthesis "inhibitors" (see Table 1) but rather produced a characteristic "delayed cell death" (DCD) phenomenon in these cells when provided above a certain level, the DCD-level: continued growth for up to 3 days was observed in presence of the new compounds before practically all cells underwent apoptotic cell death. It was additionally surprising that many non-malignant cells are very resistant to the apoptosis-inducing effect of the new specific inhibitors of NAD biosynthesis. For instance a 10000-fold higher concentration is necessary to kill human bone marrow cells compared to most tested human cancer cell lines. Thus, the "delayed cell death" characteristic can be used in an assay to screen for compounds according to the present invention.

The ability of the compounds of the invention to inhibit the NAD biosynthesis from niacinamide can be shown with an easily reproducible test system which measures the incorporation of radioactive niacinamide into NAD and NADP. This assay provides a further screening system to examine any chemical compound for its ability to selectively inhibit the cellular niacinamide mononucleotide formation. The assay allows to screen for and select the inhibitory compounds of the present invention without being bound to a particular structural characterization. Accordingly, there is no limitation on the chemical structure of these compounds as long as they exhibit said specific inhibitory activity, and any known preparation methods can be used.

The fact that the death of tumor cells initiated by these compounds is indeed due solely to the inhibition of the NAD biosynthesis from niacinamide and not due to any other effect could be unequivocally verified: Addition of excess niacinamide to the extracellular medium in which the cells are grown in vitro completely reverses the apoptosis inducing effect of the new compounds.

The effects of the compounds according to the invention on cell growth under high-density conditions have been investigated in order to closely simulate the in vivo situation of solid tumors. For this purpose, the inventors seeded high cell numbers and carried out high density cell culture experiments with the compounds shown in Table 2 below. Cell growth was monitored at various times up to 10 days as described in the experimental part below. Human hepatocarcinoma cells (HepG2) were used, for example.

Figure 5:
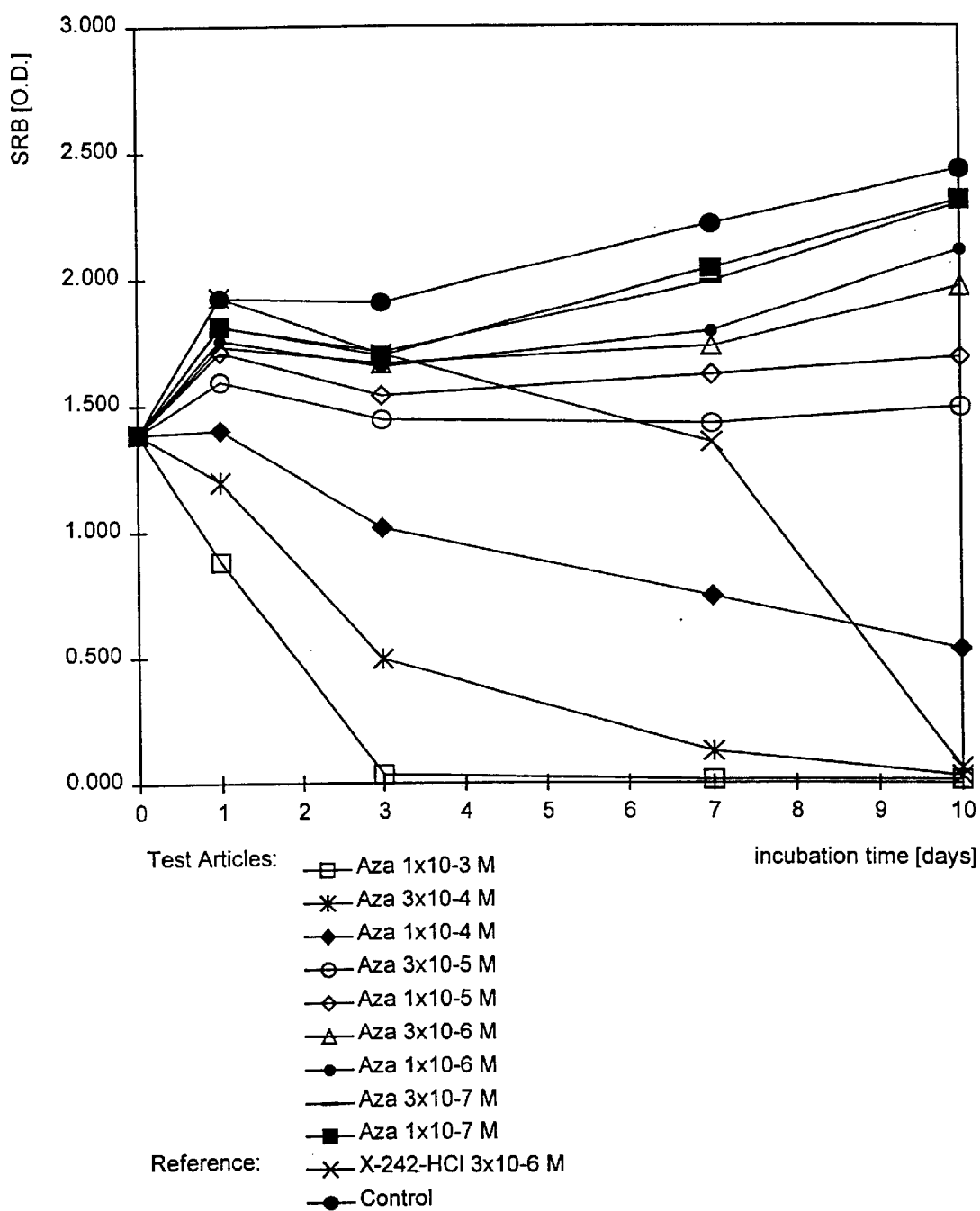
FIG. 5: Time curve of the action of Azaserine in different concentrations on the HepG2 cell growth in comparison to a control and an internal standard determined by the SRB assay.
Figure 6:
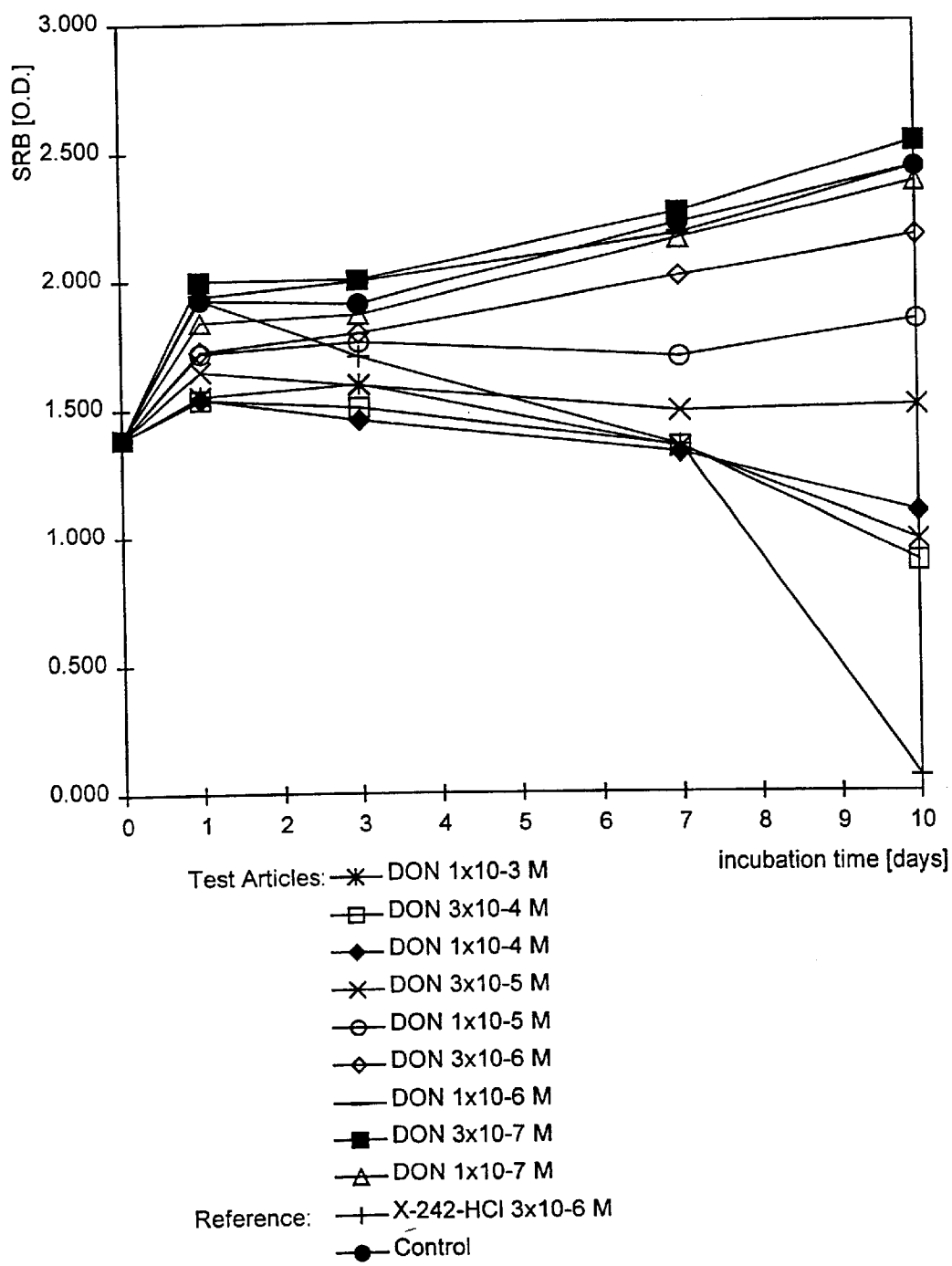
FIG. 6: Time curve of the action of 6-Diazo-5-oxo-L-norleucine in different concentrations on the HepG2 cell growth in comparison to a control and an internal standard determined by the SRB assay.
Figure 7:
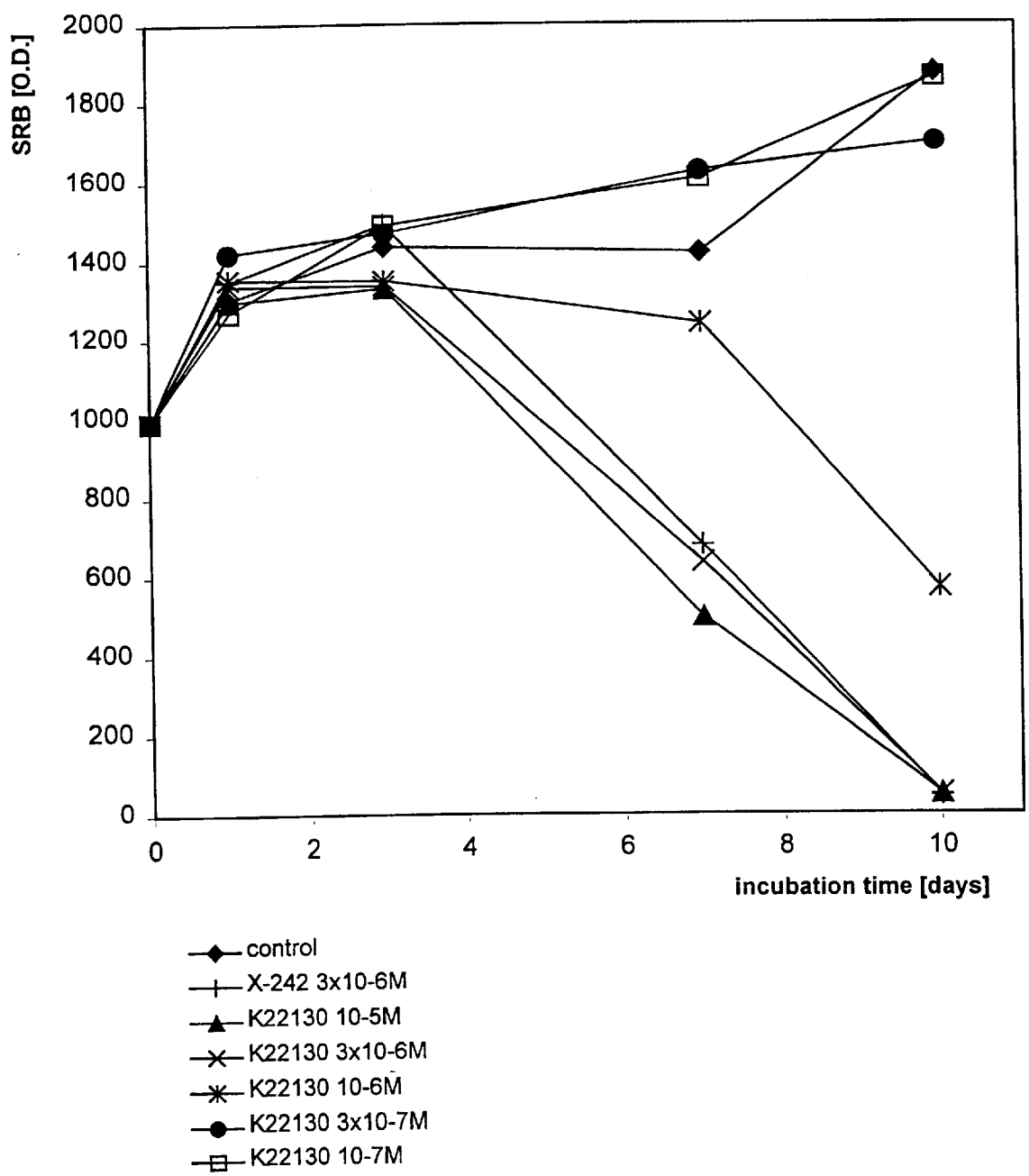
FIG. 7: Time curve of the action of K22130 in different concentrations on the HepG2 cell growth in comparison to a control and an internal standard determined by the SRB assay.
Figure 8:
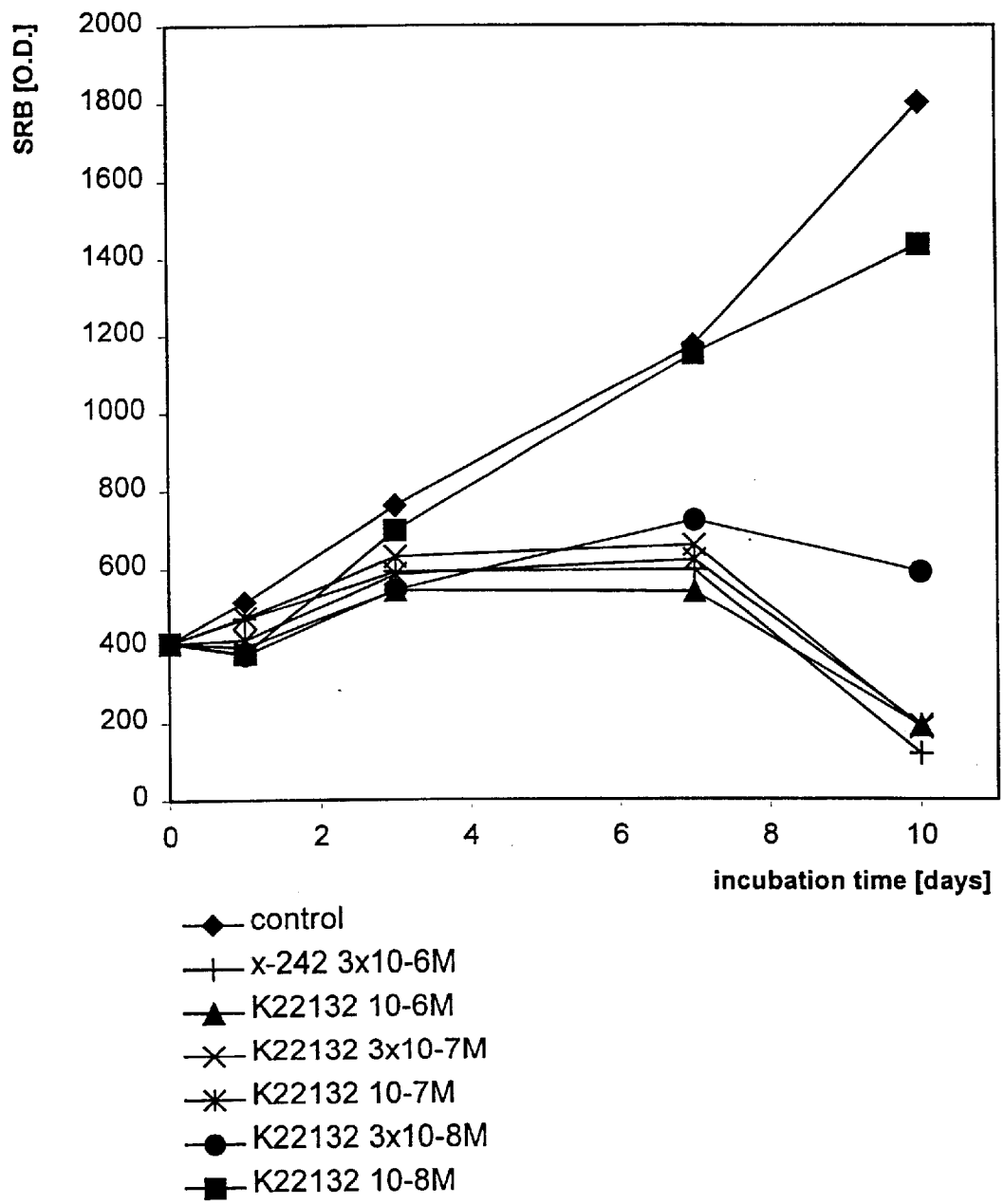
FIG. 8: Time curve of the action of K22132 in different concentrations on the HepG2 cell growth in comparison to a control and an internal standard determined by the SRB assay.
Figure 9:
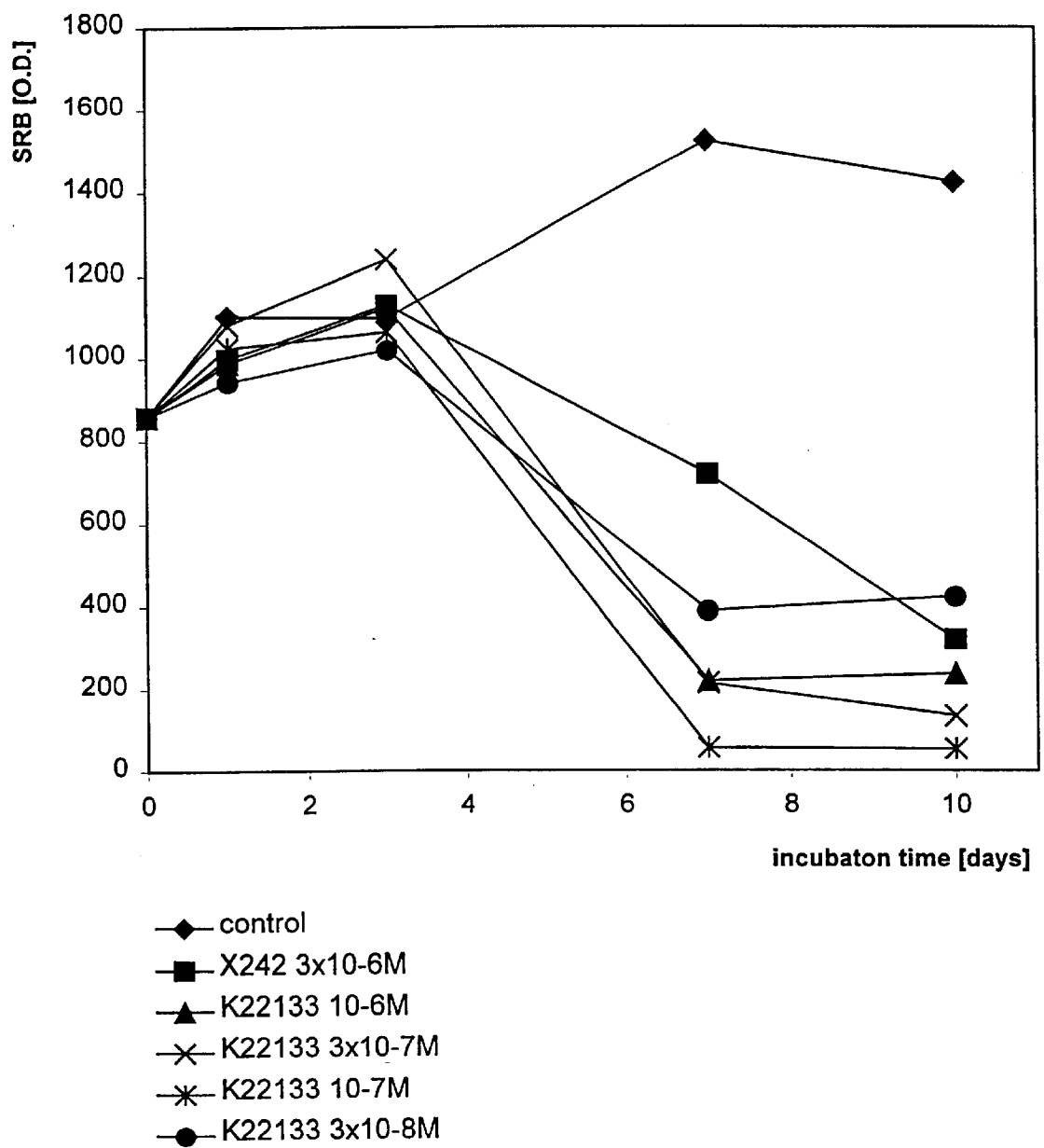
FIG. 9: Time curve of the action of K22133 in different concentrations on the HepG2 cell growth in comparison to a control and an internal standard determined by the SRB assay.
Figure 10:
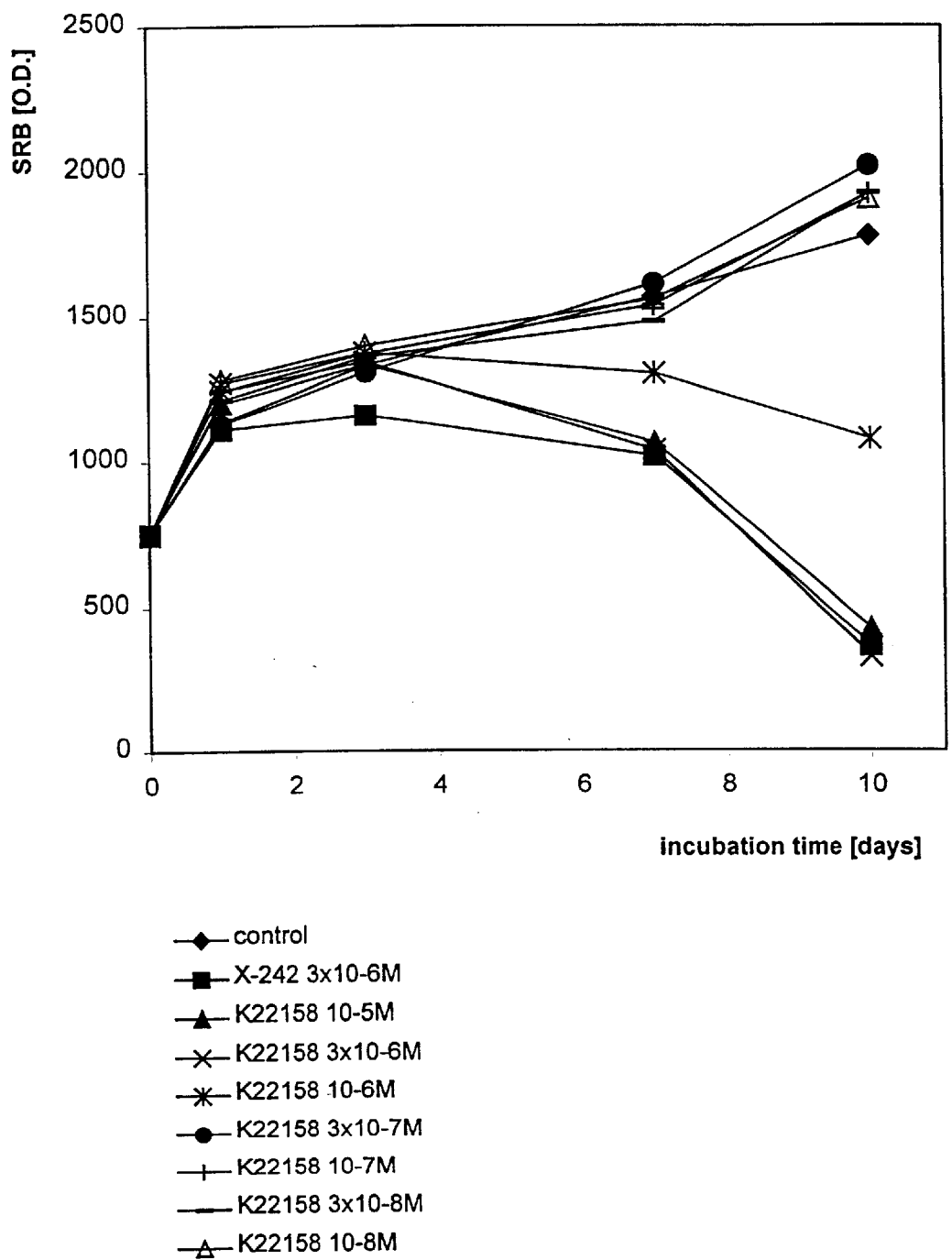
FIG. 10: Time curve of the action of K 22158 in different concentrations on the HepG2 cell growth in comparison to a control and an internal standard determined by the SRB assay.
Figure 11:
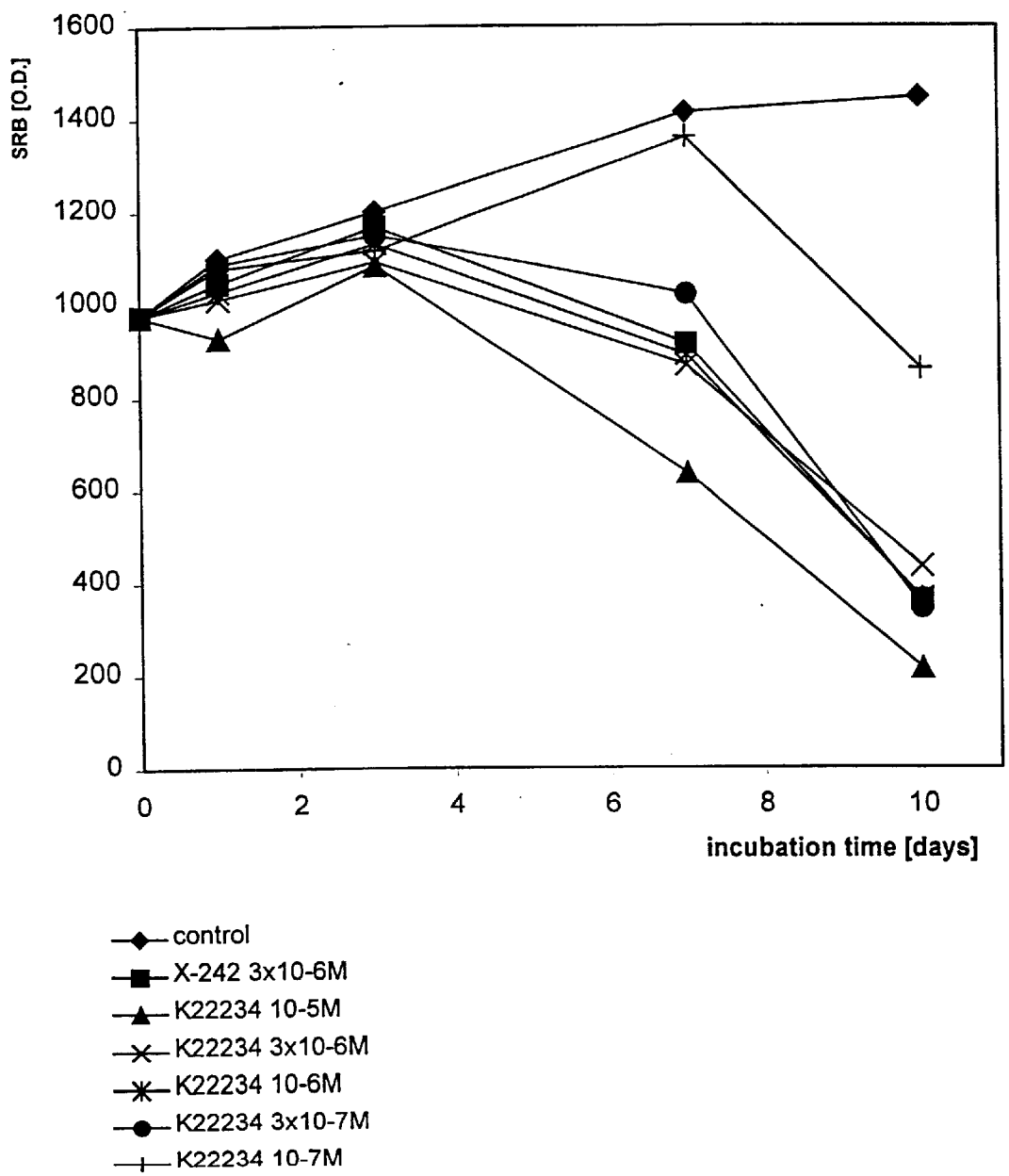
FIG. 11: Time curve of the action of K 22234 in different concentrations on the HepG2 cell growth in comparison to a control and an internal standard determined by the SRB assay.
Figure 12:
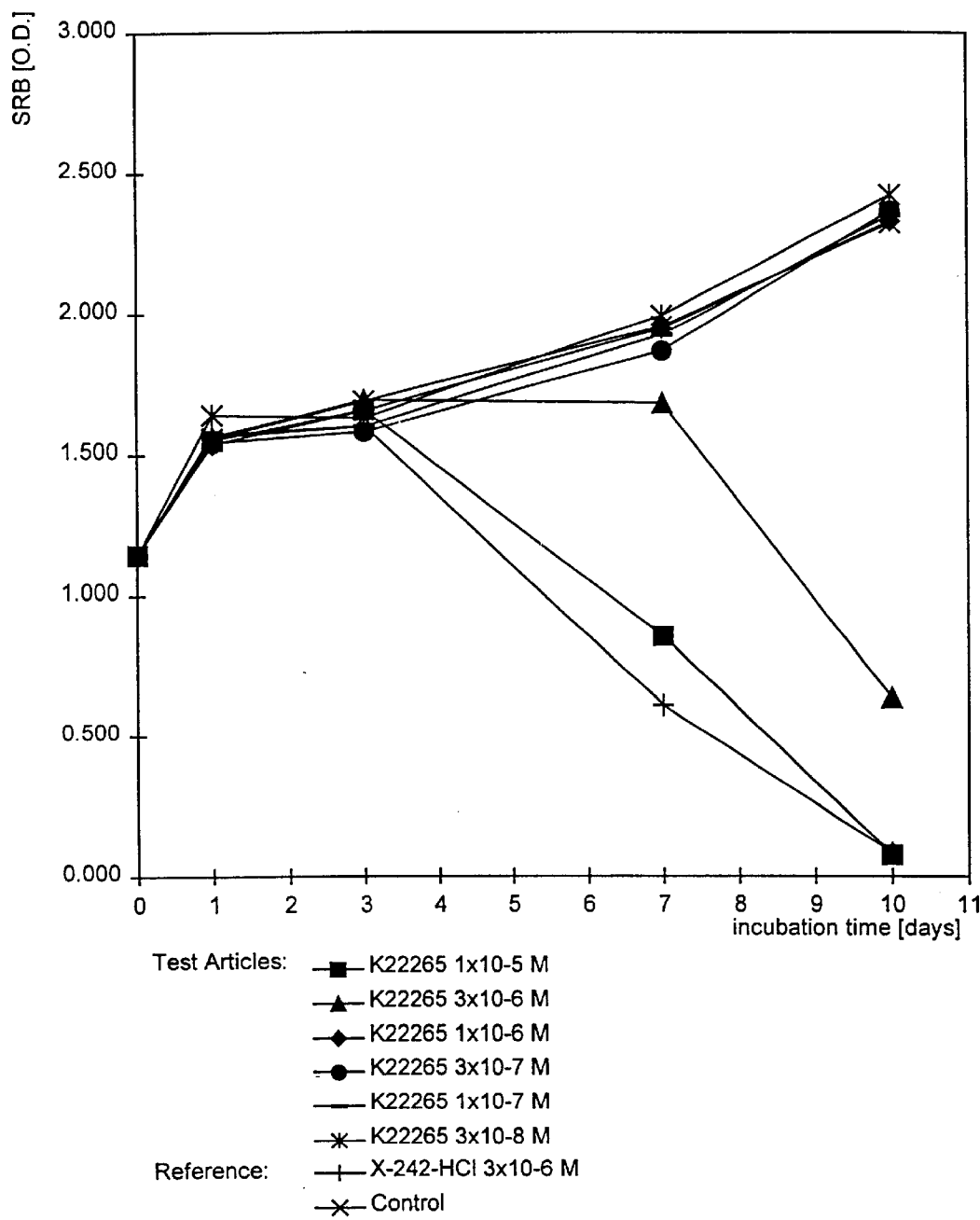
FIG. 12: Time curve of the action of K 22265 in different concentrations on the HepG2 cell growth in comparison to a control and an internal standard determined by the SRB assay.
Figure 13:
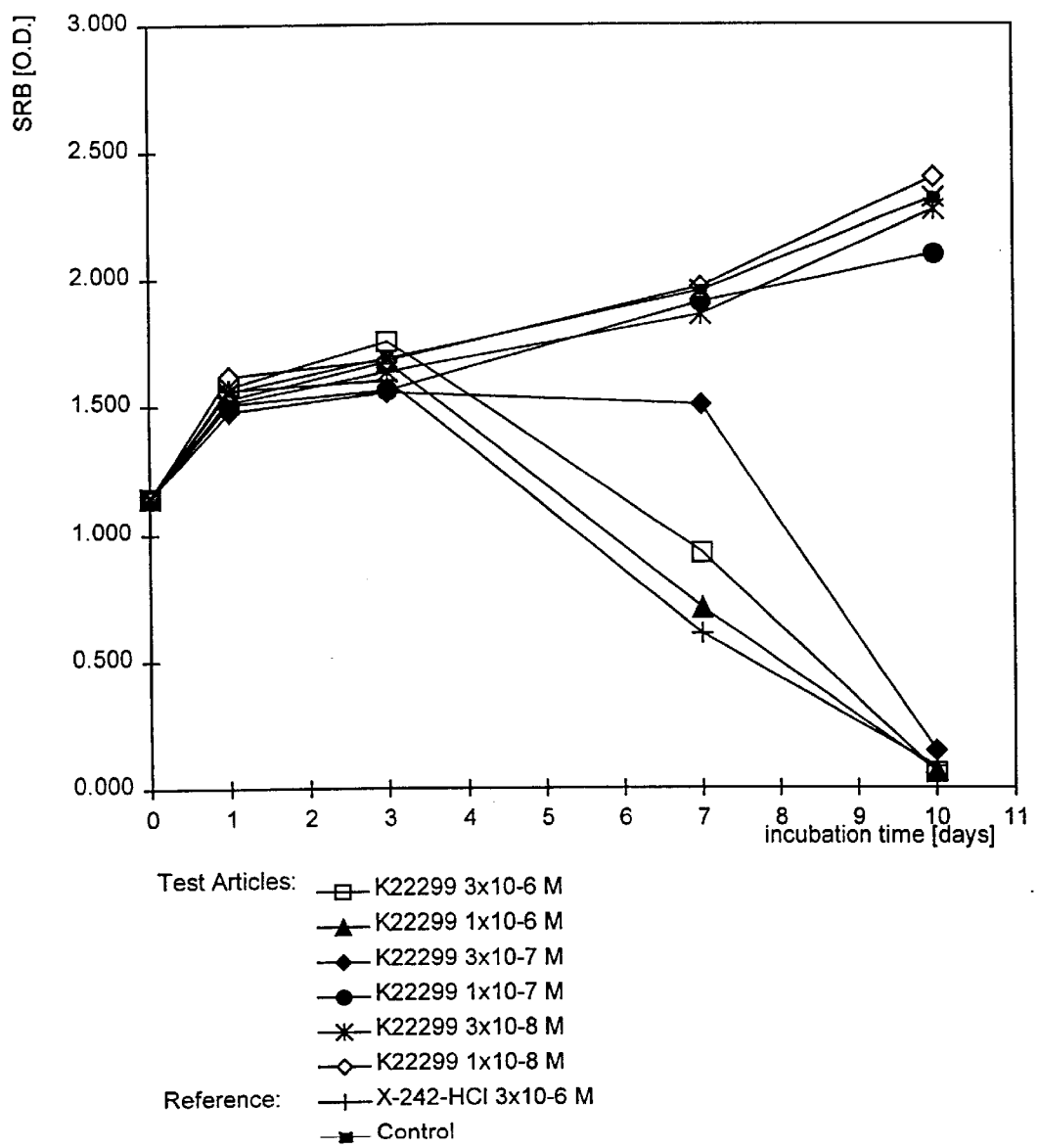
FIG. 13: Time curve of the action of K 22299 in different concentrations on the HepG2 cell growth in comparison to a control and an internal standard determined by the SRB assay.
Figure 14:
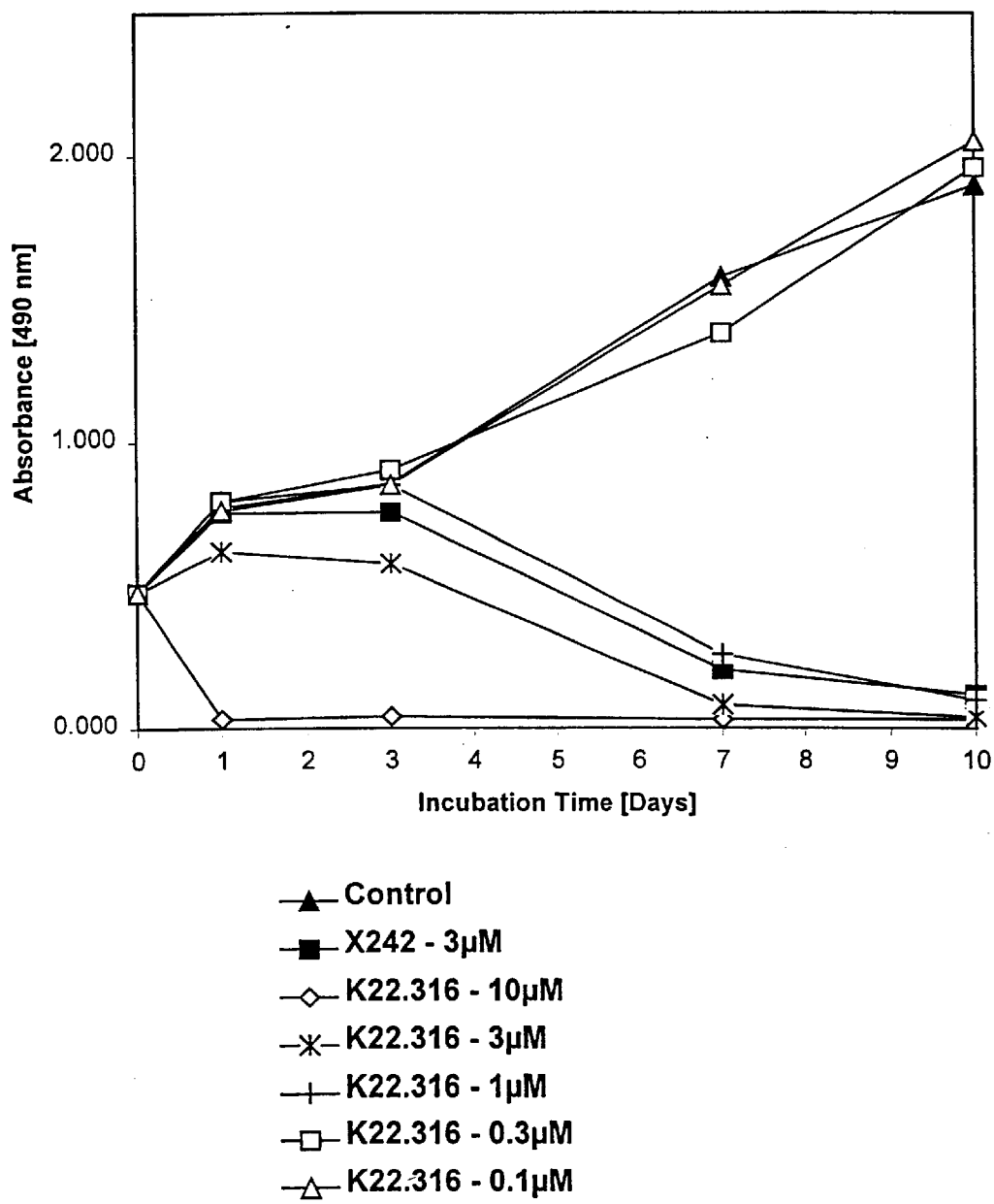
FIG. 14: Time curve of the action of K 22316 in different concentrations on the HepG2 cell growth in comparison to a control and an internal standard determined by the SRB assay.
Figure 15:
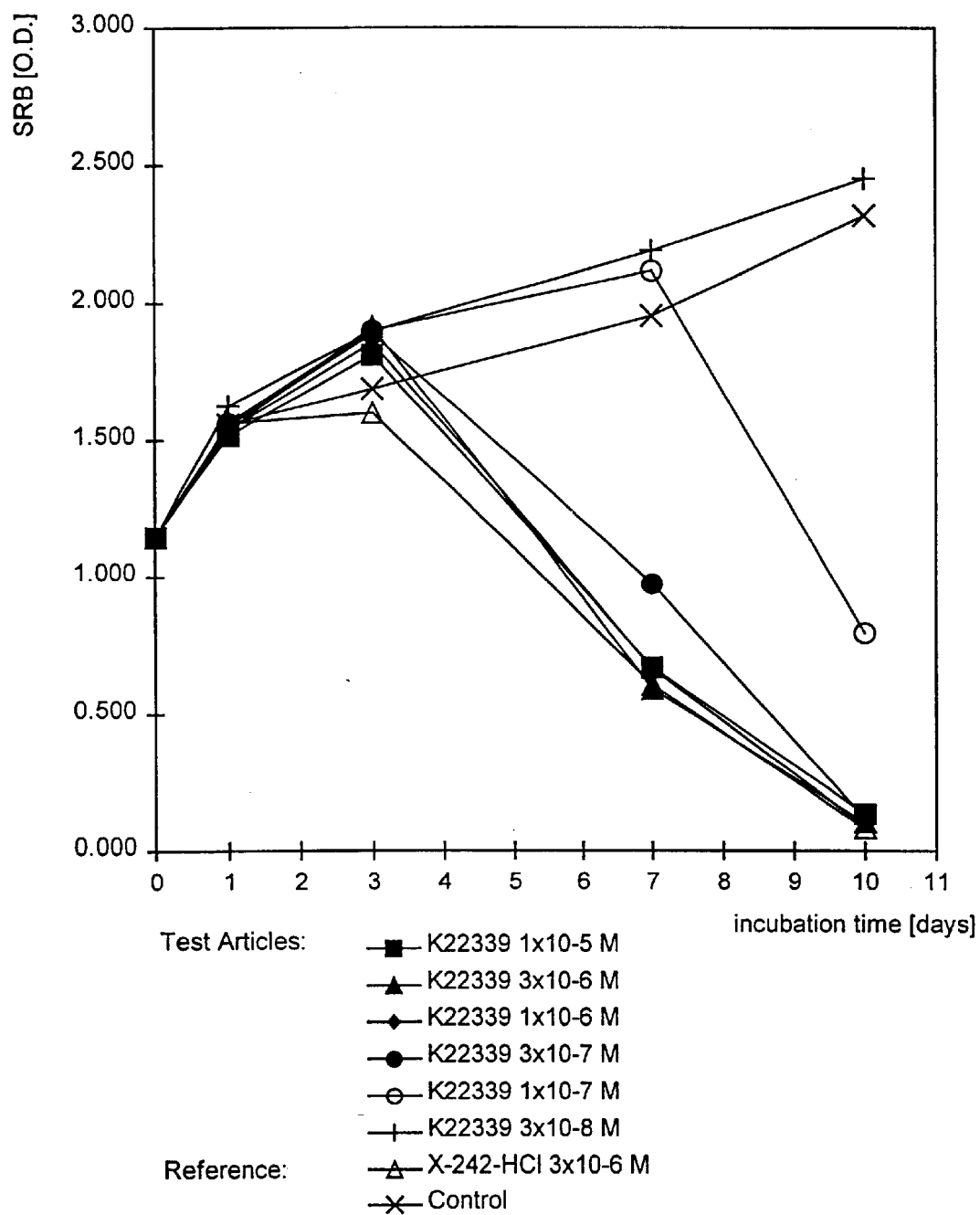
FIG. 15: Time curve of the action of K 22339 in different concentrations on the HepG2 cell growth in comparison to a control and an internal standard determined by the SRB assay.
Figure 16:
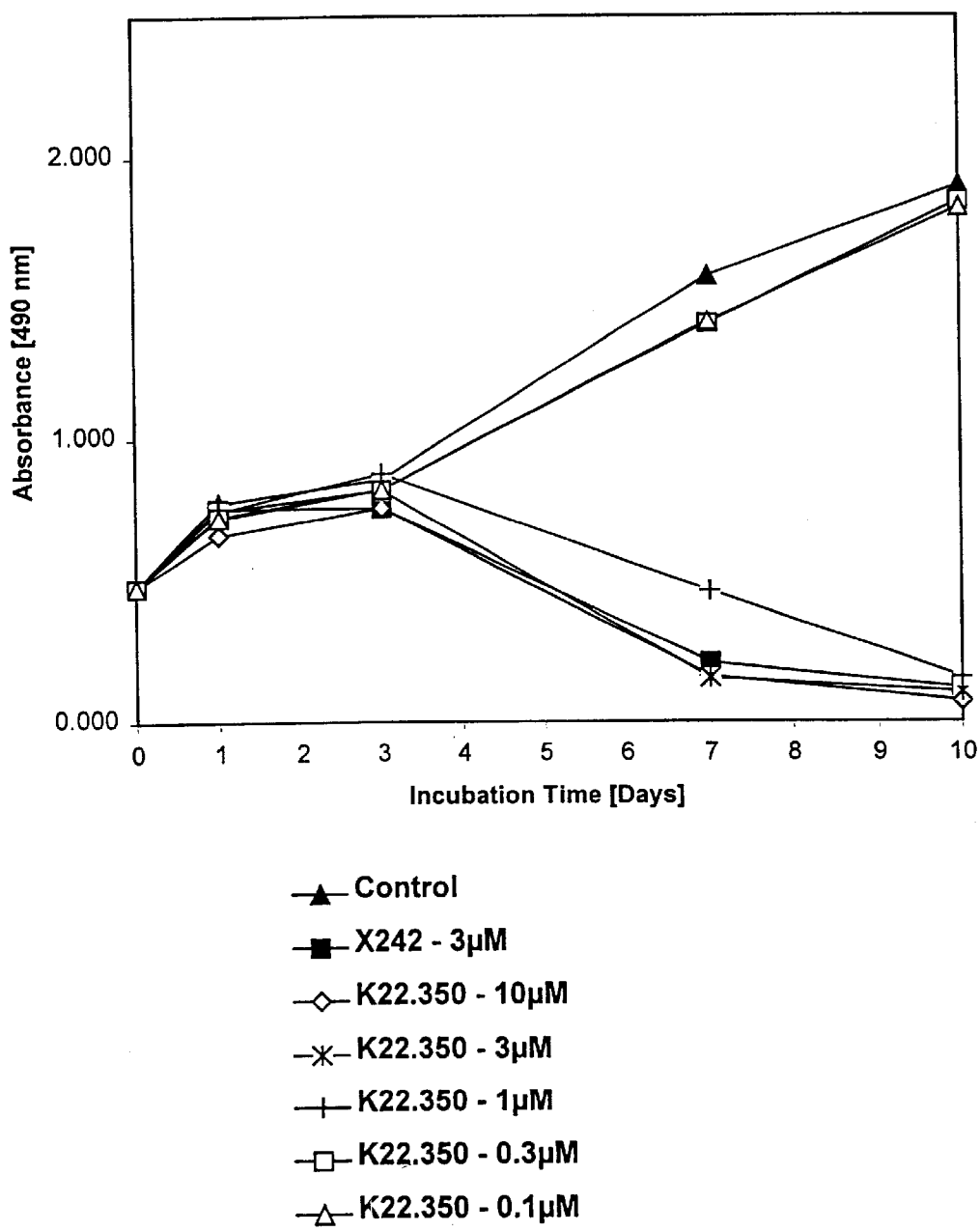
FIG. 16: Time curve of the action of K 22350 in different concentrations on the HepG2 cell growth in comparison to a control and an internal standard determined by the SRB assay.
Figure 17:
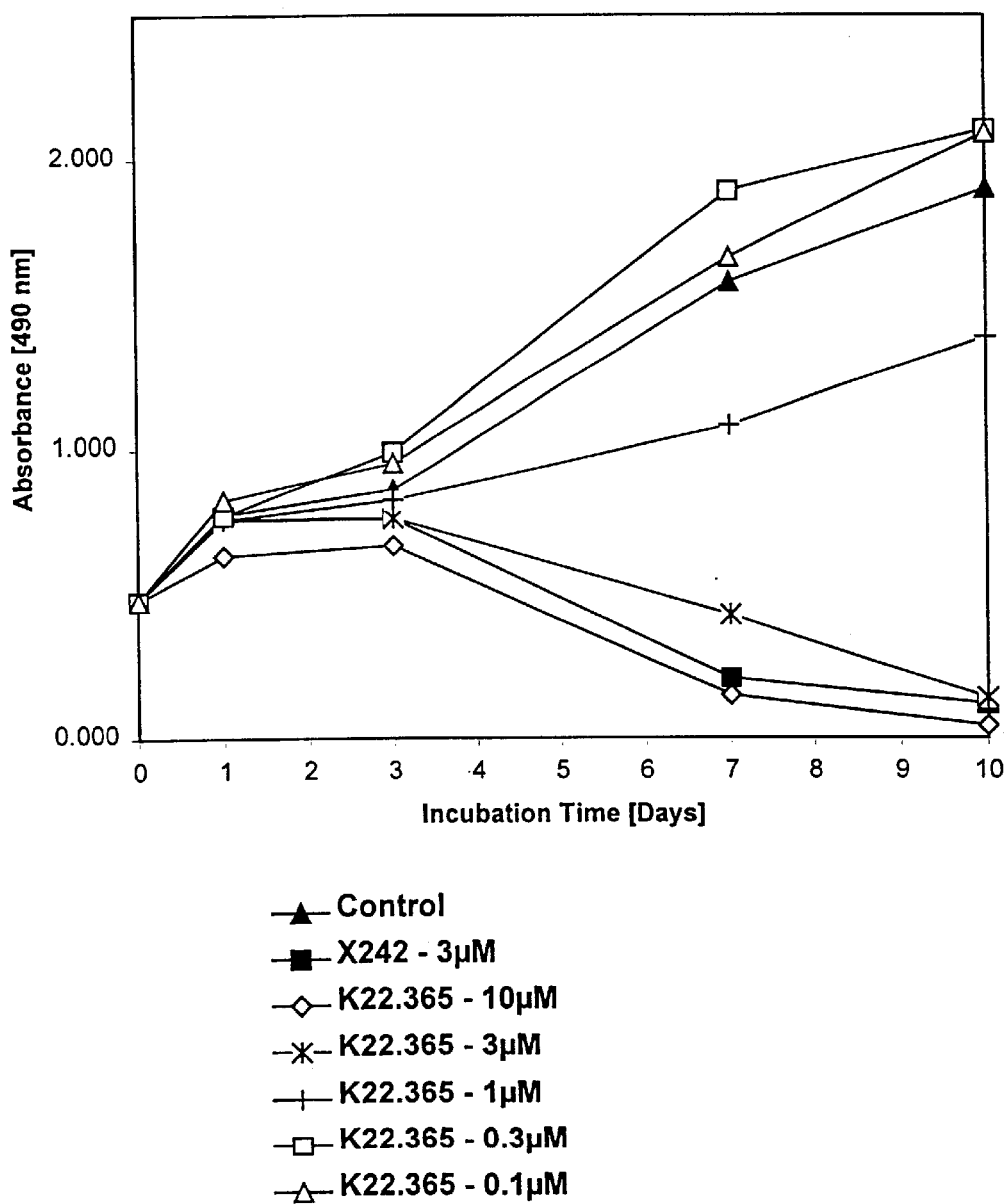
FIG. 17: Time curve of the action of K 22365 in different concentrations on the HepG2 cell growth in comparison to a control and an internal standard determined by the SRB assay.
Figure 18:
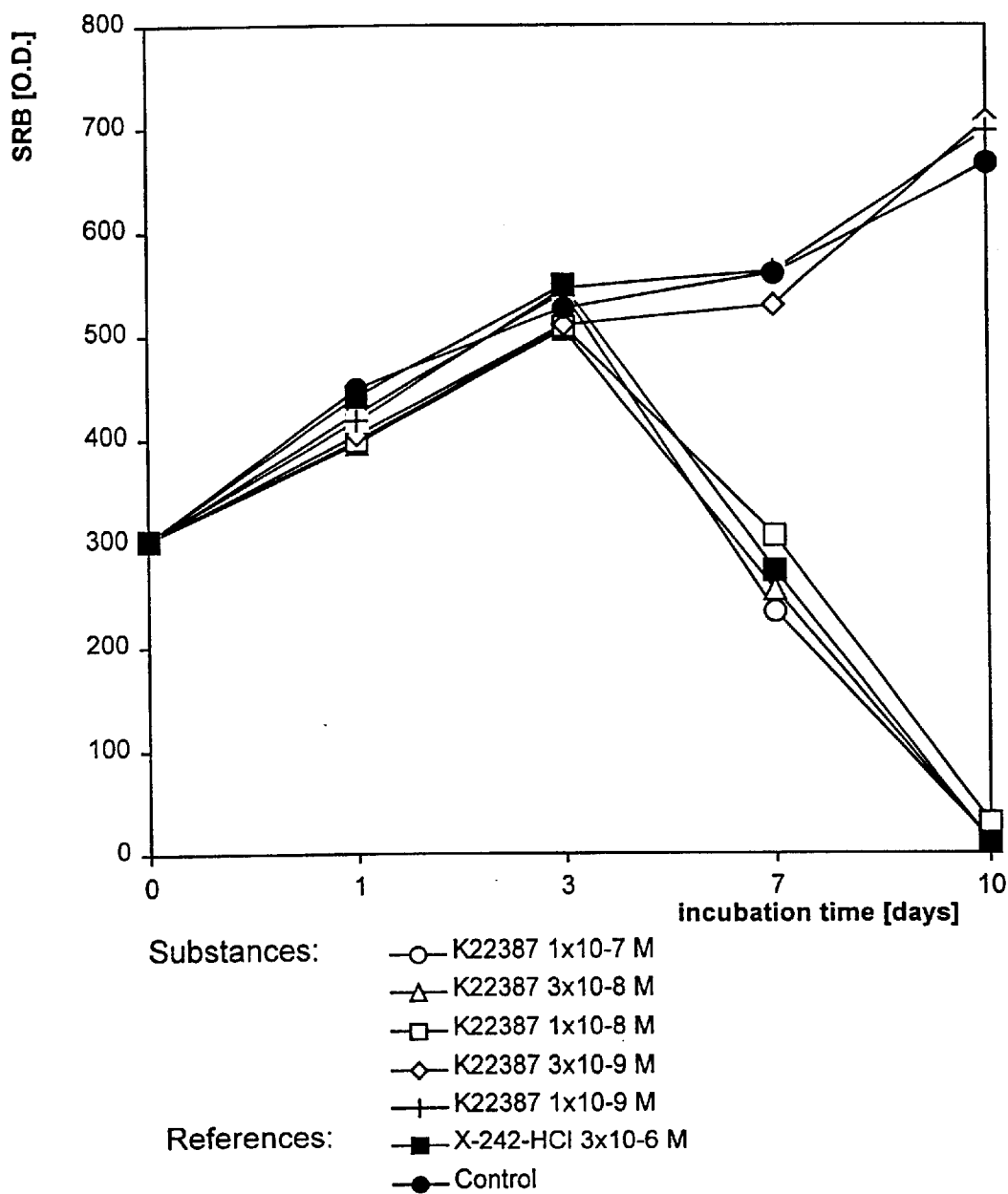
FIG. 18: Time curve of the action of K 22387 in different concentrations on the HepG2 cell growth in comparison to a control and an internal standard determined by the SRB assay.
Figure 19:
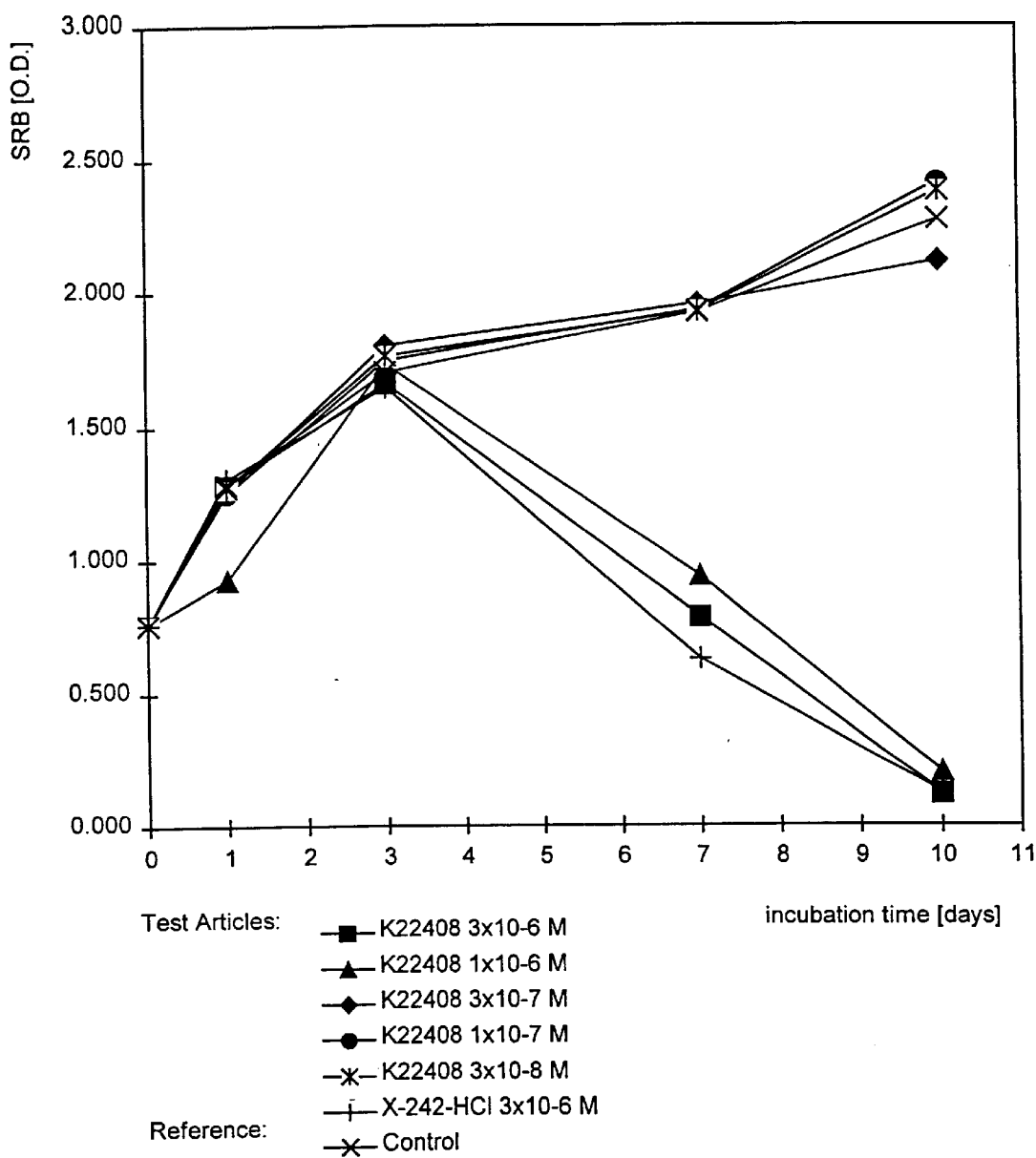
FIG. 19: Time curve of the action of K 22408 in different concentrations on the HepG2 cell growth in comparison to a control and an internal standard determined by the SRB assay.
Figure 20:
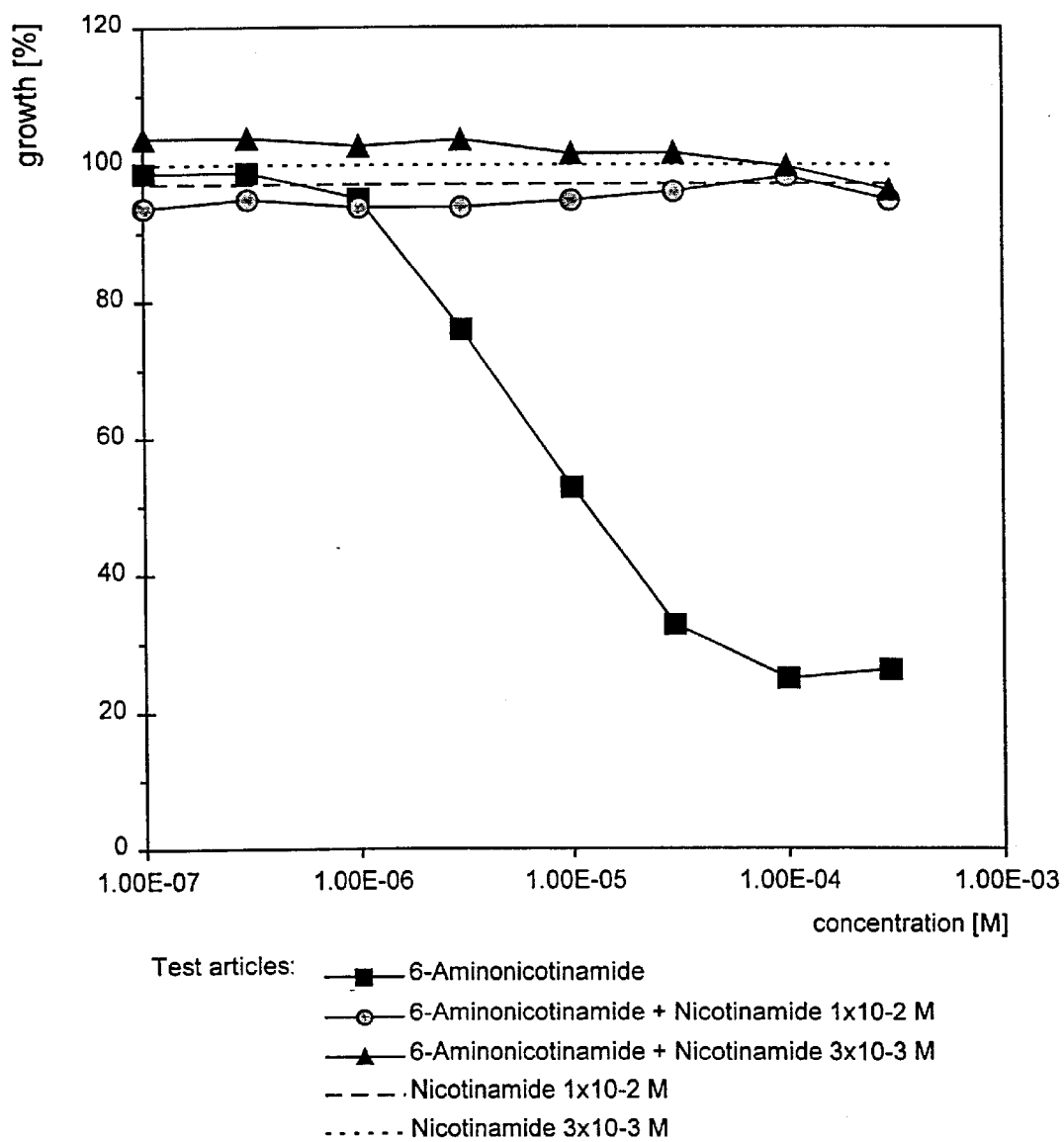
FIG. 20: Influence of nicotinamide on the cell growth inhibition of 6-Amino-nicotinamide at different concentrations.
Figure 21:
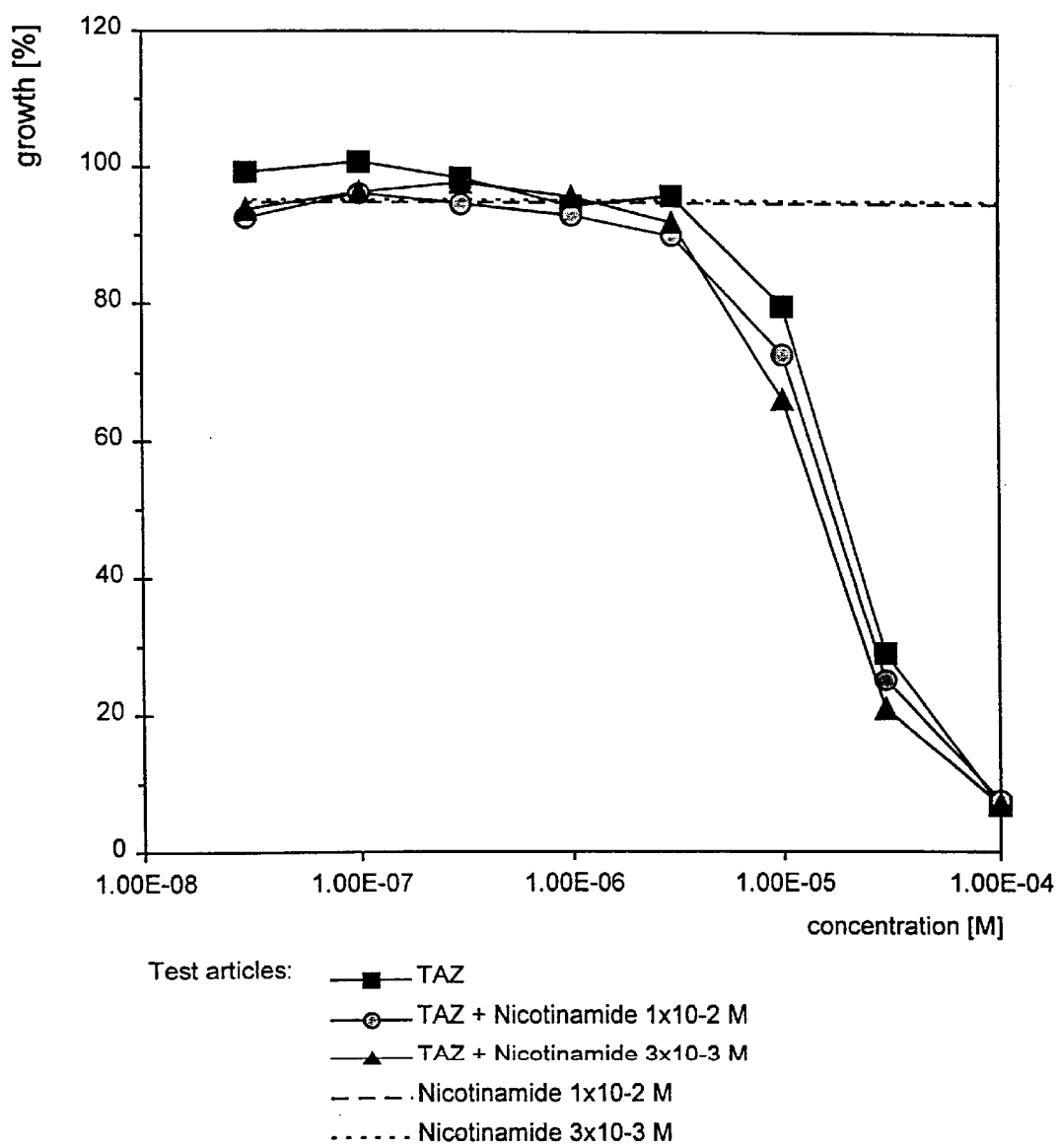
FIG. 21: Influence of nicotinamide on the cell growth inhibition of Tiazofurin at different concentrations.
Figure 22:
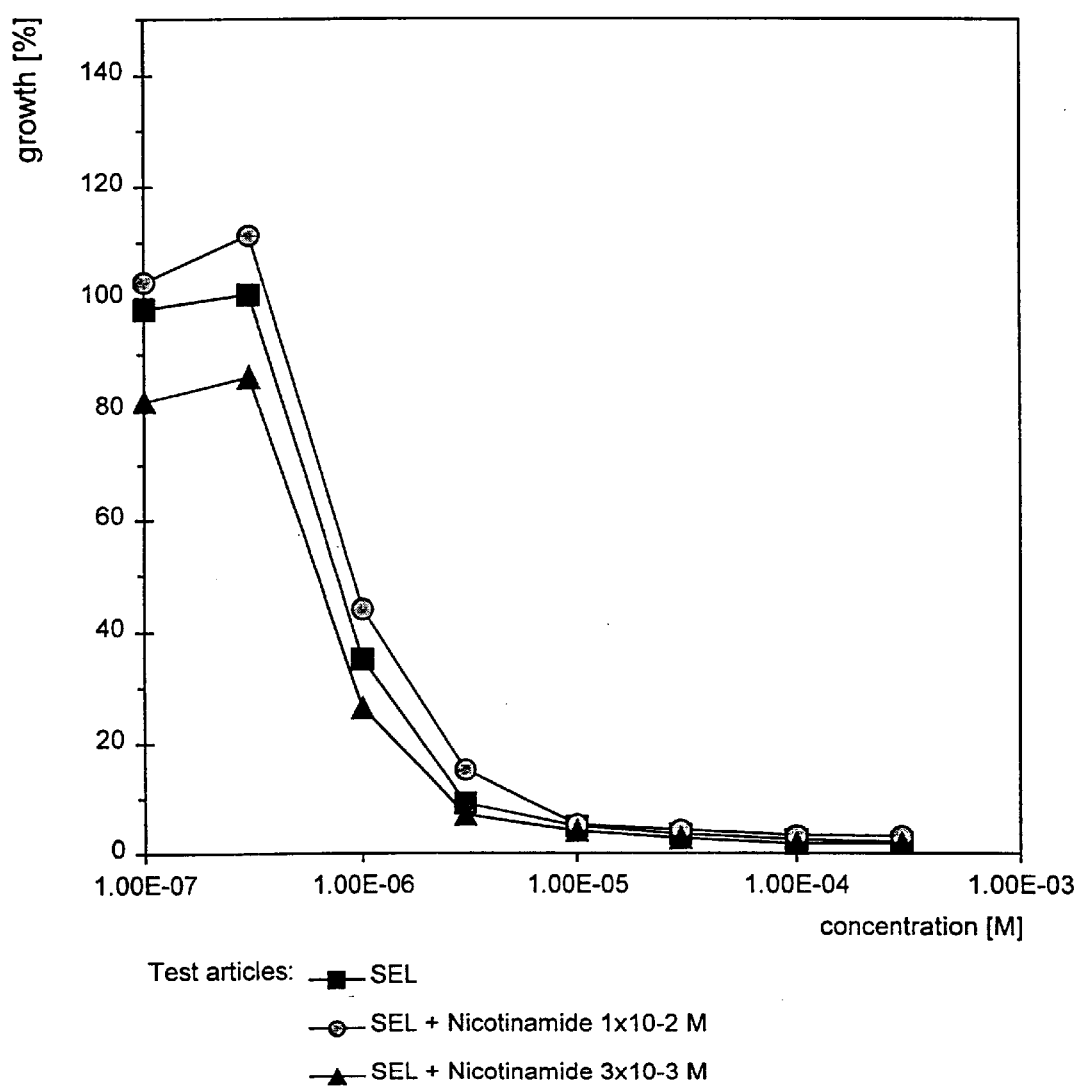
FIG. 22: Influence of nicotinamide on the cell growth inhibition of Selenazofurin at different concentrations.
Figure 23:
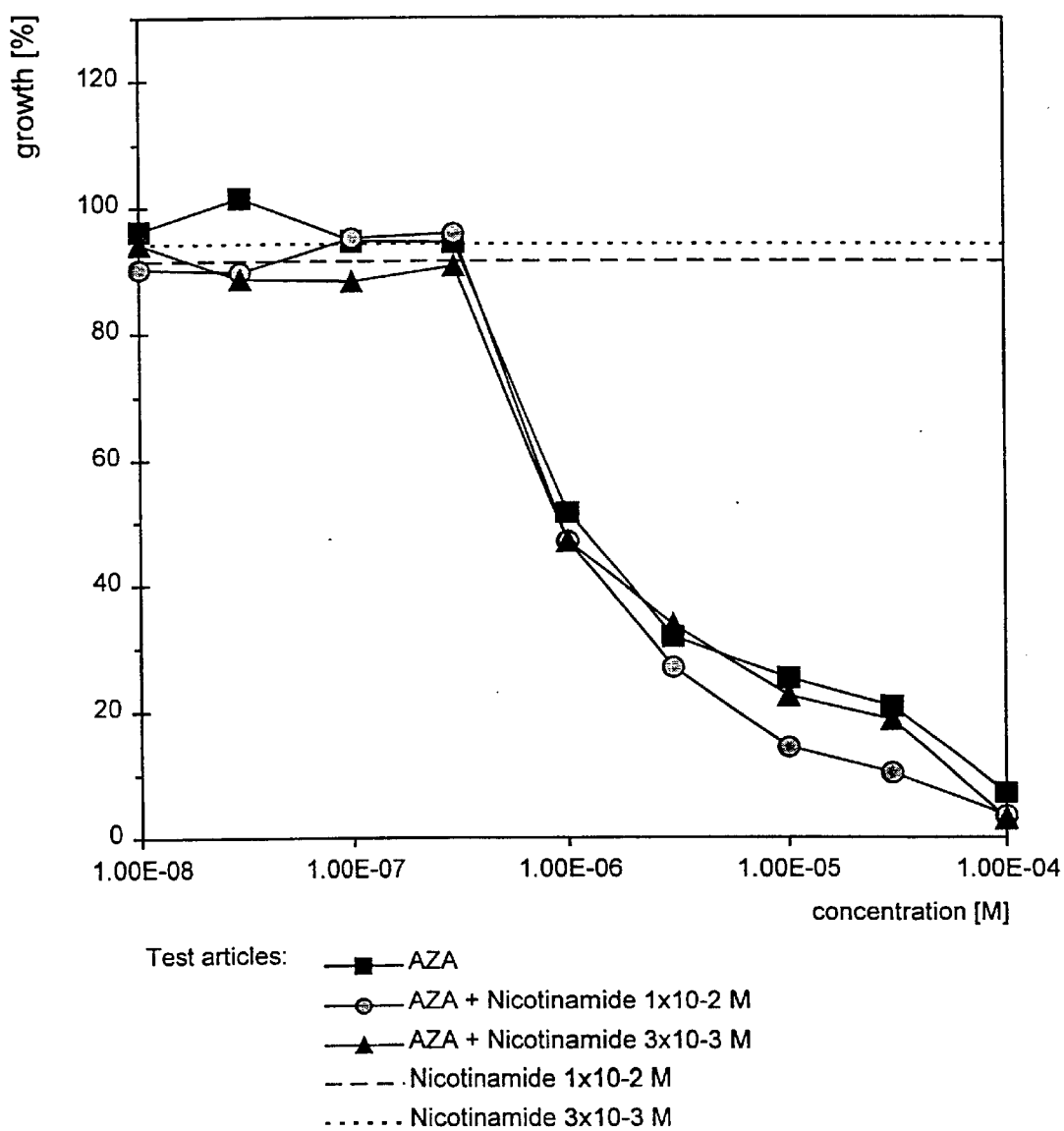
FIG. 23: Influence of nicotinamide on the cell growth inhibition of Azaserin at different concentrations.
Figure 24:
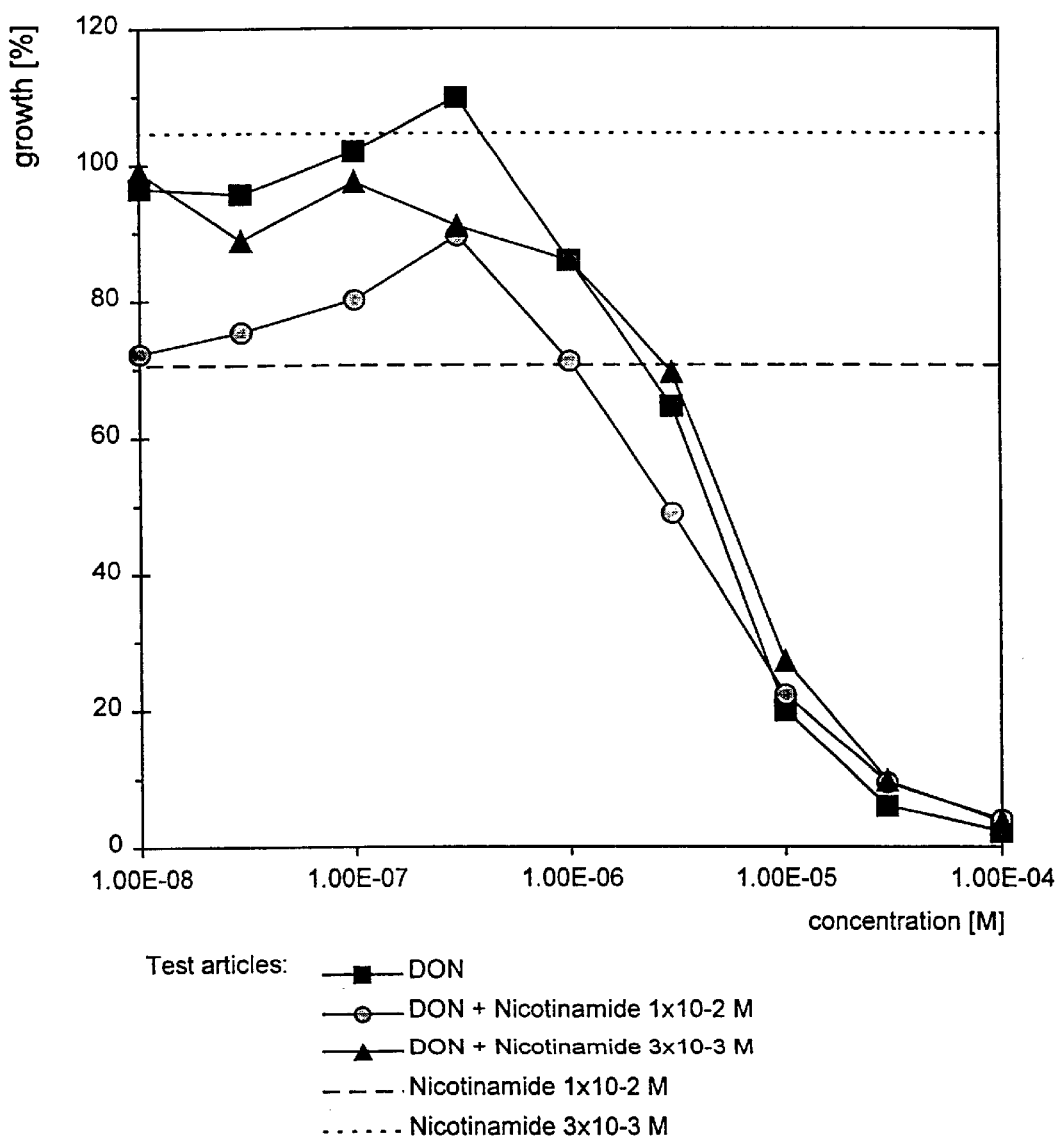
FIG. 24: Influence of nicotinamide on the cell growth inhibition of 6-Diazo-5-oxo-L-norleucine at different concentrations.
Figure 25:
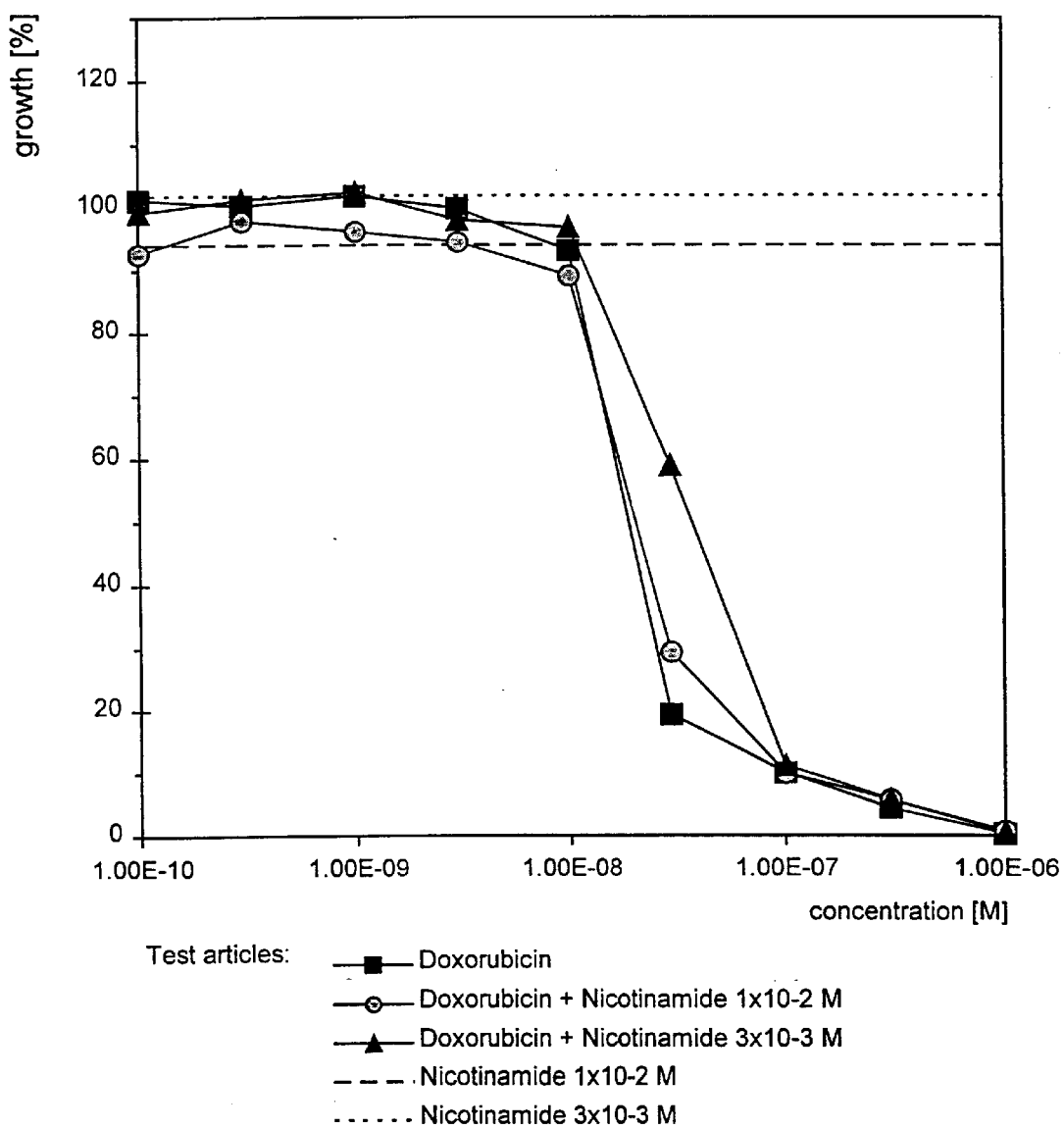
FIG. 25: Influence of nicotinamide on the cell growth inhibition of Doxorubicin at different concentrations.
Figure 26:
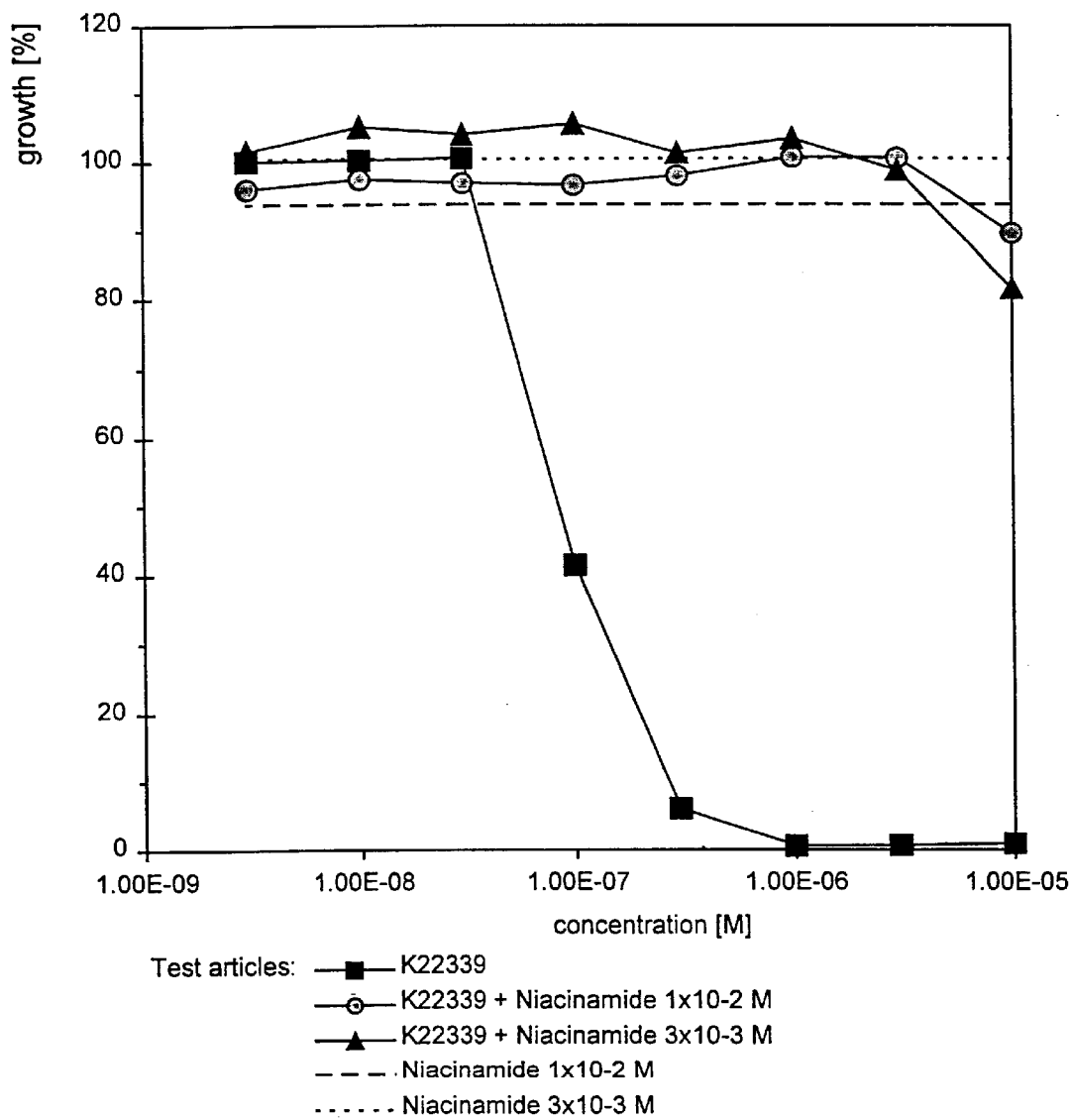
FIG. 26: Influence of nicotinamide on the cell growth inhibition of K 22339 at different concentrations.
Figure 27:
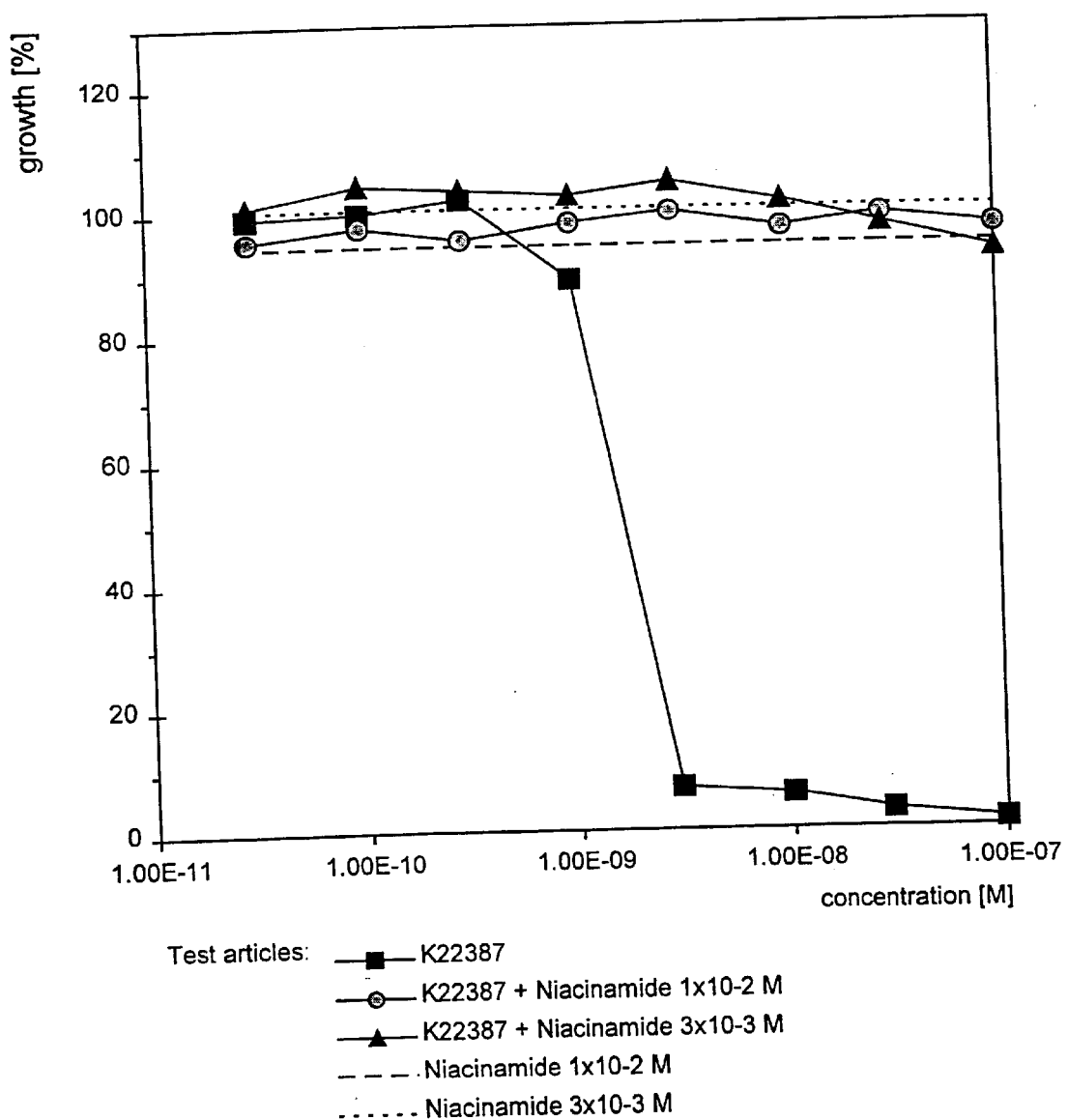
FIG. 27: Influence of nicotinamide on the cell growth inhibition of K 22387 at different concentrations.

The time curve of the action of the compounds is characterized by the induction of "delayed cell death" which is clearly distinguished from a rapid decline of cell numbers occurring after the application of toxic compounds. The "delayed cell death" phenomenon is described using for example the results obtained with K22339. FIG. 16 demonstrates the characteristic time curve of growth inhibition by compound K22339. During incubation with K22339 at concentrations of at least 0.3 μM the number of HepG2 cells increased up to three days, after which the culture was no longer able to grow and cell numbers declined from day 7 to day 10. Cell death occurred on day 4, and the cells gradually detached until day 10. In contrast, toxic compounds are less active in high density cultures and effective concentrations induced a rapid decrease in cell numbers compared to control observed as soon as one to three days of incubation, see e.g. FIG. 5, where for Azaserine the effective (toxic) concentration is 100 μM. Using K22339, however, a concentration of 0.3 μM was sufficient to bring about the full-blown effect. A still ten times higher concentration did neither show acute cytotoxicity, nor was it able to accelerate the time until the cell number gradually decreased. This characteristic action was referred to as delayed cell death. Time curves of the action on the HepG2 cell growth in comparison to a control and an internal standard are provided as FIGS. 2–7 and as FIGS. 8–19 for the toxic compounds and for examples of the specific highly effective compounds according to the invention, respectively.

TABLE 2

| K-No. | Structure | DCD [μM] |
|---|---|---|
| K22130 | 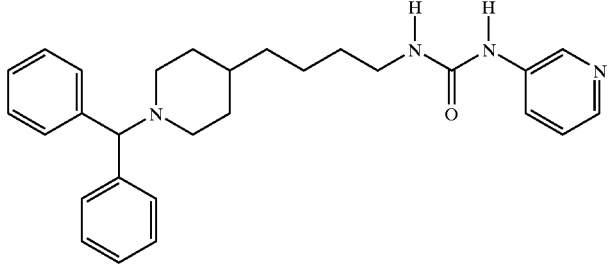<br>1-[4-(1-benzhydryl-piperidine-4-yl)-butyl]-3-pyridine-3-yl-urea | 1 |
| K22132 | 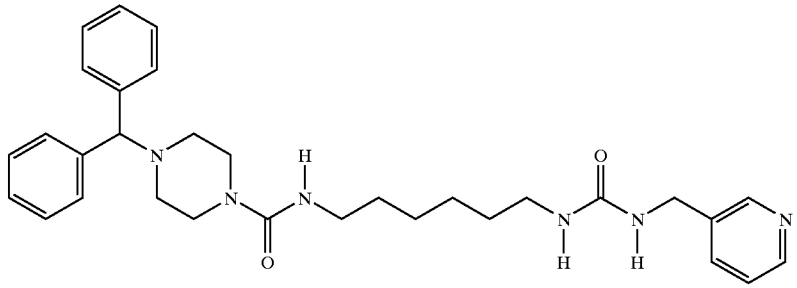<br>4-benzhydryl-piperazine-1-carboxylic acid-[6-(3-pyridine-3-yl-methylureido)-hexyl]-amide | 0.1 |
| K22133 | 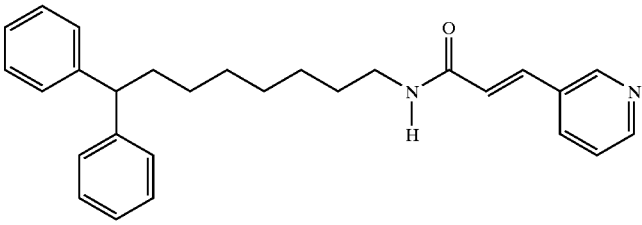<br>N-(8,8-diphenyl-octyl)-3-pyrid-3-yl-acrylamide | 0.03 |
| K22158 | 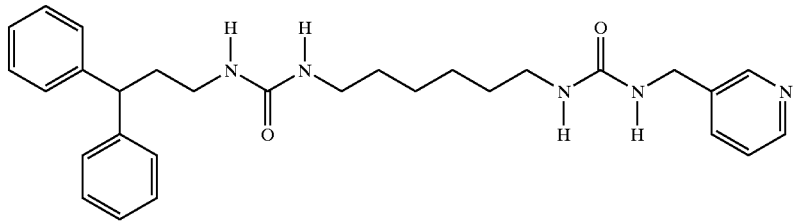<br>1-(3,3-diphenylpropyl)-3-[6-(3-pyridine-3-yl-methylureido)-hexyl]-urea | 1 |

TABLE 2-continued

| K-No. | Structure | DCD [μM] |
|---|---|---|
| K22234 | 1-[5-(1-benzhydryl-piperidine-4-yl)-pentyl]-3-pyridine-3-yl-thiourea | 0.3 |
| K22265 | 6-(4-benzhydryl-piperazine-1-yl)-hexanoic acid-(2-pyridine-3-yl-ethyl)-amide | 3 |
| K22299 | 1-(6,6-diphenyl-5-hexenyl)-3-(pyridine-3-yl-methylene-amino)-thiourea | 0.3 |
| K22316 | N-(4-{1-[4-(1-benzhydryl-piperidine-4-yl)-butyl]-piperidine-4-yl}-butyl)-3-pyridine-3-yl-propanoic acid amide | 1 |

TABLE 2-continued
| K-No. | Structure | DCD [μM] |
|---|---|---|
| K22339 | 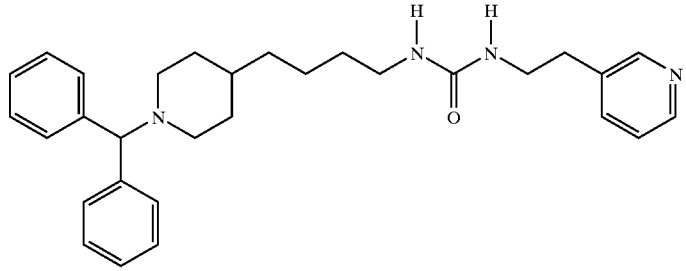<br>1-[4-(1-benzhydryl-piperidine-4-yl)-butyl]-3-<br>(2-pyridine-3-yl-ethyl)-urea | 0.3 |
| K22350 | 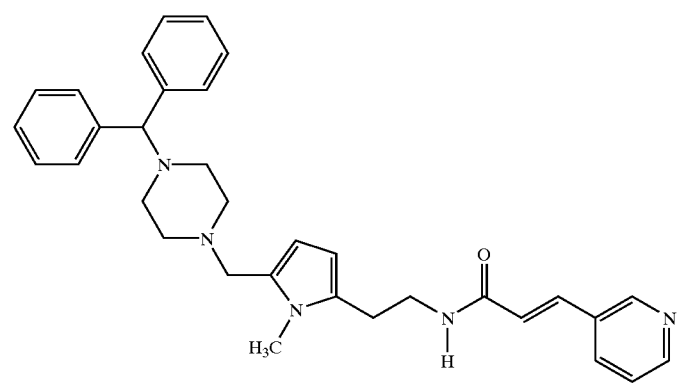<br>N-{2-[5-(4-benzhydryl-piperazine-1-yl-methyl)-1-methyl-<br>1H-pyrrole-2-yl]-ethyl}-3-pyridine-3-yl-acrylamide | 1 |
| K22365 | 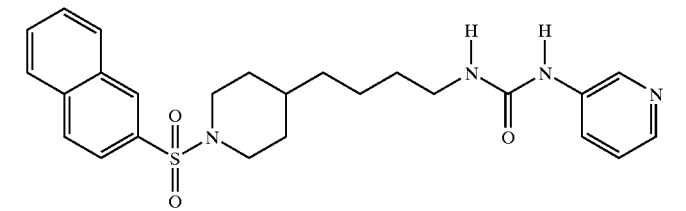<br>1-{4-[1-(naphthalene-2-sulfonyl)-piperidine-4-yl]-butyl}-<br>3-pyridine-3-yl-urea | 3 |
| K22387 | 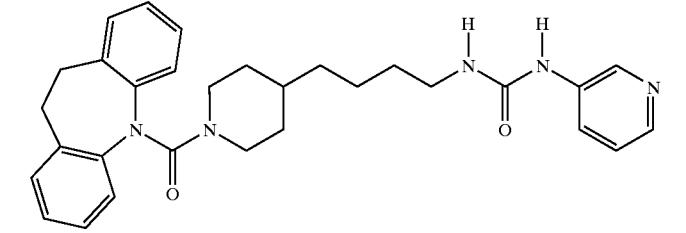<br>1-{4-[1-(10,11-dihydro-dibenzene[b,f]azepine-5-carbonyl)-<br>piperidine-4-yl]-butyl}-3-pyridine-3-yl-urea | 0.01 |

TABLE 2-continued

| K-No. | Structure | DCD [μM] |
|---|---|---|
| K22408 | 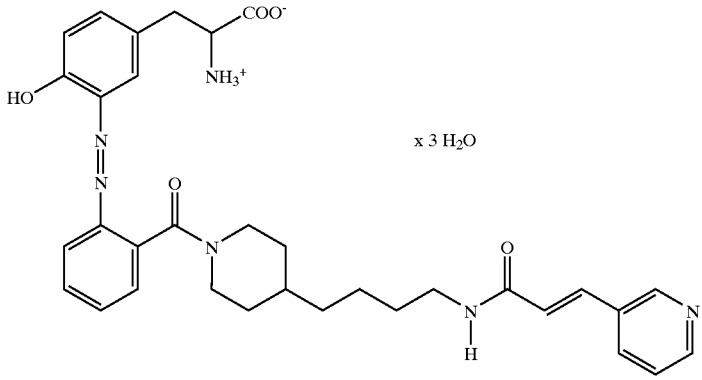<br>2-amino-3-[4-hydroxy-3-(2-{4-[4-(3-pyridine-3-yl-acryloyl-amino)-butyl]-piperidine-1-carbonyl}-phenylazo)-phenyl]-propanoic acid trihydrate | 1 |

The DCD-value was defined as the minimum concentration of the respective compound, which—despite initial growth of the culture—induced cell death below the number of initially seeded cells. All compounds were active on high density cultures of HepG2 cells at concentrations of 3 μM or lower. It is therefore preferred that the compounds of the present invention are active in the "delayed cell death" test at a concentration of 3 μM or lower, particularly preferred at a concentration of 1 μM or lower. The compounds listed in Table 2 were prepared according to standard methods known in the art. The effective (toxic) concentrations of the toxic compounds are listed in Table 5.

In a preferred embodiment the compounds according to the present invention comprise the structural feature corresponding to a pyridyl group substituted in the ring 3-position. In other words, the biologically active compound according to the invention is represented by the general formula (A):

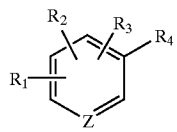

wherein
Z is CH or N,
$R_1$, $R_2$, $R_3$ and $R_4$ are selected independently from each other from carbohydrate groups optionally containing one or more of the elements selected from N, O, P, F, Cl, Br and I; and pharmaceutically acceptable salts thereof. In a preferred embodiment, $R_4$ is represented by formula (B)

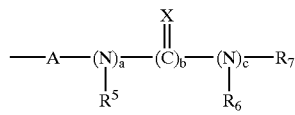

wherein
A is a bond or a bivalent carbohydrate group optionally containing one or more of the elements selected from N, O, P, F, Cl, Br and I;

X is O, S or $NR_8$;
$R_5$, $R_6$, $R_7$ and $R_8$ have the same meaning as $R_1$ in formula (A);
each of a, b and c are independently 0 or 1, with the proviso that if each of a and c is 1 then b is also 1.

The time course of the effect of the compounds suggested that there was no acute unspecific toxicity on the tumor cells. This time course is in sharp contrast to the results described in JP-459555. The authors wrote that a 20 min incubation period of tumor cells with the disclosed extract was sufficient to induce cell death. On the other hand, the present compounds seem to impose some physiological limitation on the cells which should leave enough time for them to sense the restriction and commit suicide before uncontrolled necrosis could take place. "Delayed cell death" induced by the compounds occurred in the form of apoptosis which is a favorable way of removing no longer viable cells, because it avoids the unregulated release of cell contents to the surrounding tissue.

In a preferred embodiment for compounds according to the invention the "delayed cell death" induced by the compounds can be antagonized by the addition of niacinamide as can be seen in FIG. 20 to 27, as for Tiazofurin, Selenazofurin, Azaserin, 6-Diazo-5-oxo-L-norleucine, and Doxorubicin no measurable influence of the addition of nicotinamide on the action of these toxic compounds on cell growth is seen, whereas the DCD triggered by for example K22339 and K22387 can be antagonized, as described in the Nicotinamide Reversibility Assay.

The effect of the compounds on the synthesis of NAD(P) starting from niacinamide was investigated using for example the tumor cell line HepG2 according to the technique described in the experimental part below. As shown in Table 3a, examples of the compounds according to the invention almost completely inhibited the de novo synthesis of NAD(P) from its precursor niacinamide. The toxic compounds listed in Table 3b showed either a small or even no influence on the de novo synthesis of NAD(P) from its precursor niacinamide, as the maximum inhibition relative to the control was always below 30%.

TABLE 3a

| Compound | NAD(P) pmol/10^6 cells | NAD(P) pmol/mg protein | % of Control |
|---|---|---|---|
| Control | 302.1 | 186.4 | 100 |
| K22132 | 4.1 | 2.5 | 1.4 |
| K22234 | 3.4 | 2.1 | 1.1 |
| K22265 | 7.3 | 4.5 | 2.4 |
| K22299 | 1.6 | 1.0 | 0.5 |
| K22339 | 2.5 | 1.6 | 0.8 |
| K22350 | 2.7 | 1.7 | 0.9 |
| k22387 | 2.6 | 1.6 | 0.9 |
| K22408 | 4.9 | 3.0 | 1.6 |

TABLE 3b

| Compound | NAD(P) pmol/10^6 cells | NAD(P) pmol/mg protein | % of Control |
|---|---|---|---|
| Control | 531 | 374.00 | 100.0 |
| 6-Amino-nicotinamide | 466.98 | 329.34 | 88.0 |
| Tiazofurin | 414.47 | 292.30 | 78.1 |
| Selenazofurin | 372.29 | 372.29 | 70.2 |
| Azaserine | 530.64 | 374.23 | 100.0 |
| 6-Diazo-5-oxo-L-norleucine | 586.39 | 413.55 | 110.5 |
| Doxorubicin | 539.74 | 380.65 | 101.7 |

The inhibition of the NAD(P) synthesis from niacinamide by these compounds was investigated in HepG2 cells as described in the section "Material and Methods". The compounds of Table 3a were used at a concentration of $10^{-5}$ M. The compounds of Table 3b were used at concentrations of at least $10^{-5}$ M, except for Doxorubicin where the concentration was $0.3 \times 10^{-5}$ M. As a control, vehicle treated or untreated cells were used.

Figure 28:
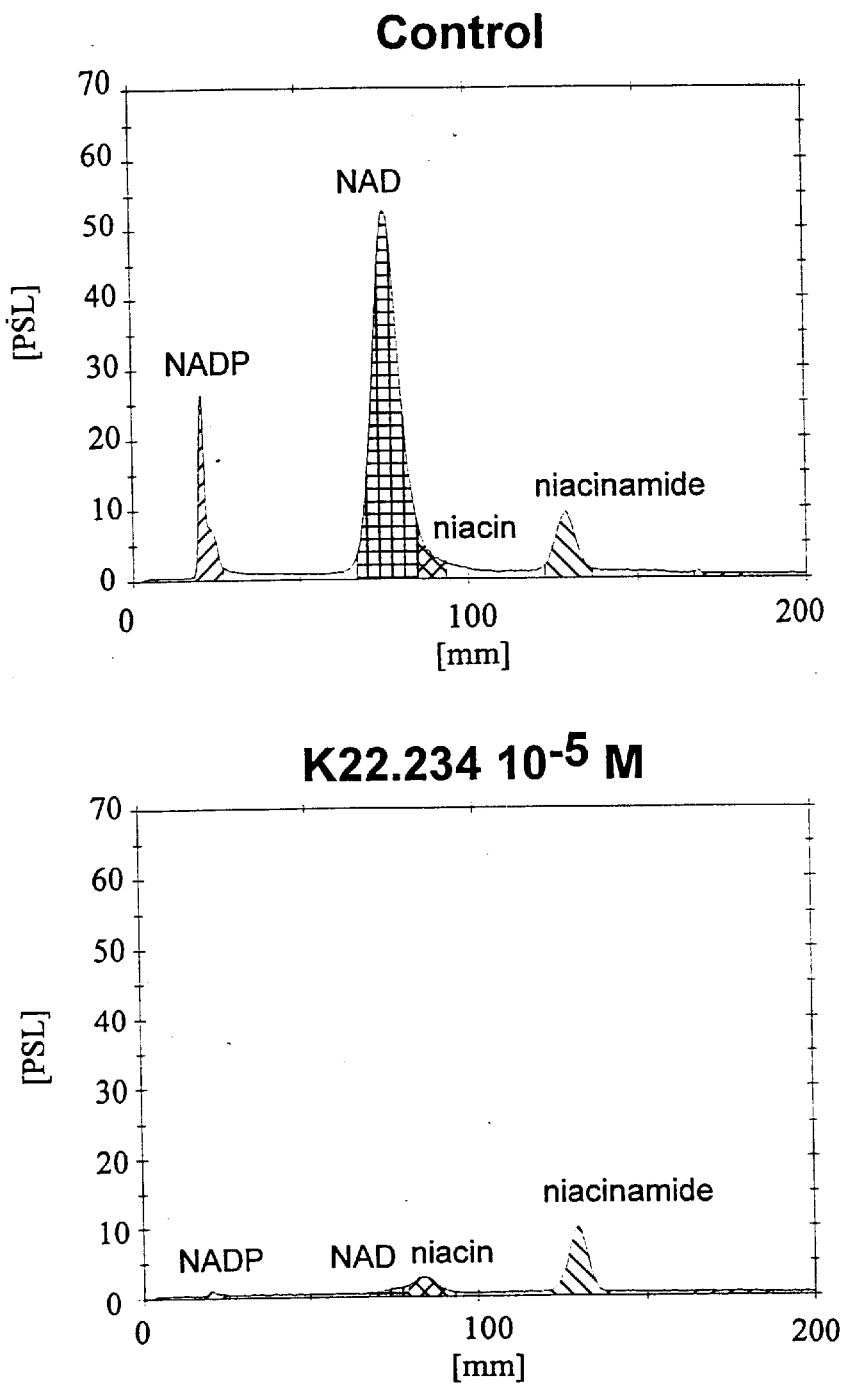
FIG. 28: Inhibitory action of K22234 on NAD(P) biosynthesis from [$^{14}$C]niacinamide in HepG2 cells. The radioactive metabolites of the cell extracts were separated on PEI cellulose using 0.05 M LiCl as solvent.

In these experiments, a pre-incubation period of 17 hrs with the compounds was used, but it turned out that the pre-incubations period could be shortened, for example to 2 hrs, or skipped completely without affecting the inhibition profile. Further analysis of the radiolabeled niacinamide metabolites revealed that the compounds exclusively blocked the formation of the niacinamide mononucleotide. FIG. 28 shows representative chromatograms of [$^{14}$C] niacinamide metabolites extracted from vehicle and K22234 treated HepG2 cells. Similar results were obtained with the other specific compounds.

By comparing the two chromatograms in FIG. 28, it is clearly evident that the compounds inhibited the synthesis of NAD(P) from its precursor niacinamide. The radiolabeled niacin seen in the extract of the vehicle and the compound treated cells resulted from the enzymatic deamidation of [$^{14}$C]niacinamide. The peaks of NAD and niacin on the chromatograms are close together, but the inventors verified the identification by the second thin-layer chromatography system, as described in the section "Materials and Methods". Since an accumulation of the intermediate niacinamide mononucleotide was not detected in the compound-treated cells, the compounds inhibit the NAD(P) biosynthesis at the step of the formation of niacinamide mononucleotide. Thus, the compounds inhibit the enzyme niacinamide pyrophosphate phosphoribosyl transferase ([EC 2.4.2.12], NAPRT; a second name of this enzyme is niacinamide mononucleotide pyrophosphorylase). Performing the same kind of experiments using [$^{14}$C]niacin instead of [$^{14}$C]niacinamide as precursor revealed that the compounds do not block the NAD(P) synthesis from the precursor niacin in cells which are able to use the niacin pathway. The observation that the niacin pathway of NAD(P) synthesis is not blocked by the compounds makes it very unlikely that pathway starting from tryptophan is suppressed by the compounds.

The effect of the compounds on the enzyme niacinamide phosphoribosyltransferase (NAPRT, EC 2.4.2.12) was investigated using for example protamine-treated cytoplasmic fraction of K-562 cells as the enzyme source according to the NAPRT assay described in the experimental part below. The investigated compounds were used in concentrations of 10 $\mu$M, except for K22387 and K22133 where the concentration was 1 $\mu$M.

The assay is based on the amount of radioactive incorporation from $^{14}$C-labelled niacinamide into niacinamide mononucleotide (NAN). NAM is subsequently separated from niacinamide (NA) by thin-layer chromatography and its quantity is determined by autoradiography. As shown in Table 4 the compounds completely inhibited the de novo synthesis of NAD(P) from its precursor niacinamide.

TABLE 4

| | [pmol/h] | | [%] | |
|---|---|---|---|---|
| Compound | NAM | NA | NAM | NA |
| K22350 | 0.0 | 468.8 | 0.00 | 100.00 |
| K22387 | 0.0 | 468.8 | 0.00 | 100.00 |
| K22408 | 0.0 | 468.8 | 0.00 | 100.00 |
| K22133 | 0.0 | 468.8 | 0.00 | 100.00 |
| K22158 | 0.0 | 468.8 | 0.00 | 100.00 |
| K22316 | 0.0 | 468.8 | 0.00 | 100.00 |
| K22365 | 0.0 | 468.8 | 0.00 | 100.00 |
| Control | 79.1 | 389.7 | 16.88 | 83.12 |
| Control | 71.8 | 397.0 | 15.32 | 84.68 |

A summary of the results of examples of the compounds according to the present invention are listed in the following Table 5 together with results obtained for the previously known toxic cytostatica. As can be clearly seen all the examples tested do fulfil the required limits.

TABLE 5

Summary of the results for the topic compounds tested together with the results for examples of the compounds according to the present invention

| | Test systems | | | | |
|---|---|---|---|---|---|
| Compounds | Cell growth inhibition IC$_{50}$-values [$\mu$M] Hep G2 | DCD [$\mu$M] | Reversal by Niacin-amide | Cellular NAD synthesis inhibition [%] | NAPRT inhibition [% of control] |
| 6-Aminonicotinamide | 4 | Tox. 10000 | yes | 12 (30 $\mu$M) | n.t. |
| Tiazofurin | 10 | Tox. 300 | no | 22 (100 $\mu$M) | n.t. |

TABLE 5-continued

Summary of the results for the topic compounds tested together with the results for examples of the compounds according to the present invention

| Compounds | Cell growth inhibition IC$_{50}$-values [μM] Hep G2 | DCD [μM] | Reversal by Niacin-amide | Cellular NAD synthesis inhibition [%] | NAPRT inhibition [% of control] |
|---|---|---|---|---|---|
| Selenazofurin | 0.7 | Tox. 30 | no | 30 (10 μM) | n.t. |
| Azaserine | 0.7 | Tox. 100 | no | 0 (10 μM) | n.t. |
| 6-Diazo-5-oxo-L-norleucine | 3 | Tox. 100 | no | 0 (10 μM) | n.t. |
| Doxorubicin | 0.02 | n.t. | no | 0 (3 μM) | n.t. |
| K22130 | 0.08 | 1 | n.t. | n.t. | 100 (1 μM) |
| K22132 | 0.02 | 0.03 | n.t. | 99 (10 μM) | 100 (1 μM) |
| K22133 | 0.02 | 0.03 | n.t. | n.t. | 100 (1 μM) |
| K22158 | 0.1 | 1 | n.t. | n.t. | 100 (10 μM) |
| K22234 | 0.2 | 0.3 | n.t. | 99 (10 μM) | 100 (10 μM) |
| K22265 | 2 | 3 | n.t. | 98 (10 μM) | 100 (10 μM) |
| K22299 | 0.1 | 0.3 | n.t. | 99 (10 μM) | 100 (10 μM) |
| K22316 | 0.9 | 1 | n.t. | n.t. | 100 (10 μM) |
| K22339 | 0.1 | 0.1 | yes | 99 (1 μM) | 100 (10 μM) |
| K22350 | 0.7 | 1 | n.t. | 99 (10 μM) | 100 (10 μM) |
| K22365 | 0.6 | 3 | n.t. | 92 (10 μM) | 100 (10 μM) |
| K22387 | 0.002 | 0.01 | yes | 99 (10 μM) | 100 (1 μM) |
| K22408 | 0.2 | 1 | n.t. | 98 (10 μM) | 100 (10 μM) |

(n.t.: not tested)

In a preferred embodiment of the invention the compounds of formula (I), disclosed in WO 97/48695 are not encompassed by the present invention:

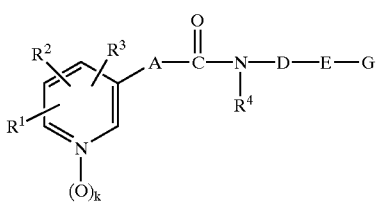

wherein
R$^1$ is
hydrogen, halogen, cyano, trifluoromethyl, hydroxy, benzyloxy, aminocarbonyl, carboxy, phenyl, phenoxy, phenylthio, pyridyloxy, pyridylthio, alkyl, especially C$_1$–C$_6$-alkyl, alkenyl, especially C$_3$–C$_6$-alkenyl, alkinyl, especially C$_3$–C$_6$-alkinyl, hydroxyalkyl, especially C$_1$–C$_6$-hydroxyalkyl, alkoxy, especially C$_1$–C$_6$-alkoxy, alkenyloxy, especially C$_3$–C$_6$-alkenyloxy, alkinyloxy, especially C$_3$–C$_6$-alkinyloxy, alkanoyloxy, especially C$_1$–C$_7$-alkanoyloxy, alkoxycarbonyloxy, especially C$_2$–C$_7$-alkoxycarbonyloxy, alkylthio, especially C$_1$–C$_6$-alkylthio, alkenylthio, especially C$_3$–C$_6$-alkenylthio, alkinylthio, especially C$_3$–C$_6$-alkinylthio, cycloalkyl, especially C$_3$–C$_8$-cycloalkyl, cycloalkyloxy, especially C$_3$–C$_8$-cycloalkyloxy, cycloalkylthio, especially C$_3$–C$_8$-cycloalkylthio, alkoxycarbonyl, especially C$_2$–C$_7$-alkoxycarbonyl, alkylaminocarbonyl, especially C$_2$–C$_7$-alkylaminocarbonyl, dialkylaminocarbonyl, especially C$_3$–C$_{13}$-dialkylaminocarbonyl, or
NR$^5$R$^6$, wherein
R$^5$ and
R$^6$ are selected independently of each other from hydrogen, alkyl, especially C$_1$–C$_6$-alkyl, alkenyl, especially C$_3$–C$_6$-alkenyl and alkinyl, especially C$_3$–C$_6$-alkinyl,
R$^2$ is
hydrogen, halogen, cyano, hydroxy, trifluoromethyl, benzyloxy, alkyl, especially C$_1$–C$_6$-alkyl, alkoxy, especially C$_1$–C$_6$-alkoxy or alkanoyloxy, especially C$_1$–C$_7$-alkanoyloxy,
wherein R$^1$ and R$^2$, if they are adjacent, optionally form a bridge which is selected from —(CH$_2$)$_4$—, —(CH═CH)$_2$— and —CH$_2$O—CR$^7$R$^8$—O—, wherein
R$^7$ and
R$^8$ are, independently of each other, hydrogen or alkyl, especially C$_1$–C$_6$-alkyl,
R$^3$ is hydrogen, halogen, alkyl, especially C$_1$–C$_6$-alkyl, trifluoromethyl or hydroxyalkyl, especially C$_1$–C$_6$-hdroxyalkyl and
R$^4$ is hydrogen, hydroxy, benzyloxy, alkyl, especially C$_1$–C$_6$-alkyl, alkenyl, especially C$_3$–C$_6$-alkenyl, alkinyl, especially C$_3$–C$_6$-alkinyl, cycloalkyl, especially C$_3$–C$_6$-cycloalkyl or alkoxy, especially C$_1$–C$_6$-alkoxy,
k is 0 or 1,
A is
alkylene, especially C$_1$–C$_6$-alkylene, which is optionally substituted once to three-fold by alkyl, especially C$_1$–C$_3$-alkyl, hydroxy, alkoxy, especially C$_1$–C$_3$-alkoxy, fluorine or phenyl, or
1,2-cyclopropylene or
alkylene with at least two C-atoms, especially C$_2$–C$_6$-alkylene in which a methylene unit can be isosterically replaced by O, S, NR$^9$, CO, SO or SO$_2$, wherein the substitution, with the exception of ═CO, cannot be adjacent to the amide group and wherein
R$^9$ is selected from hydrogen, alkyl, especially C$_1$–C$_6$-alkyl, alkenyl, especially C$_3$–C$_6$-alkenyl, alkinyl, especially C$_3$–C$_6$-alkinyl, acyl, especially C$_1$–C$_6$-acyl or alkylsulfonyl, especially C$_1$–C$_6$-alkylsulfonyl, D is
- selected from alkylene, especially $C_1$–$C_{10}$-alkylene, optionally substituted once or twice by alkyl, especially $C_1$–$C_6$-alkyl, hydroxy, or alkoxy, especially $C_1$–$C_6$-alkoxy,
- alkenylene with at least two C-atoms, especially $C_2$–$C_{10}$-alkenylene, which is optionally substituted once or twice by alkyl, especially $C_1$–$C_6$-alkyl, hydroxy, or alkoxy, especially $C_1$–$C_6$-alkoxy, wherein the double bond can also be to ring E,
- alkinylene with at least three C-atoms, especially $C_3$–$C_{10}$-alkinylene, optionally substituted once or twice by alkyl, especially $C_1$–$C_6$-alkyl, hydroxy or alkoxy, especially $C_1$–$C_6$-alkoxy, and
- alkylene, especially $C_1$–$C_{10}$-alkylene, alkenylene with at least two C-atoms, especially $C_2$–$C_{10}$-alkenylene or alkinylene with at least three C-atoms, especially $C_3$–$C_{10}$-alkinylene, whereby one to three methylene units are each isosterically replaced by O, S, $NR^{10}$, CO, SO or $SO_2$ wherein
  - $R^{10}$ has the same meaning as $R^9$ but is selected independently thereof, E is selected from

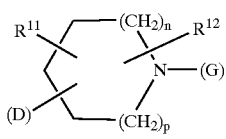 (E1)

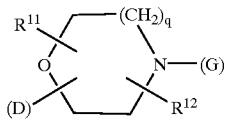 (E2)

wherein the heterocyclic ring can also optionally have a double bond and n and p can be, independently of one another 0, 1, 2 or 3, with the proviso that n+p≦4 and q is 2 or 3, $R^{11}$ is hydrogen, alkyl, especially $C_1$–$C_6$-alkyl, hydroxy, hydroxymethyl, carboxy or alkoxycarbonyl with at least two C-atoms, especially $C_2$–$C_7$-alkoxycarbonyl and $R^{12}$ is hydrogen, alkyl, especially $C_1$–$C_6$-alkyl or or an oxo group adjacent to the nitrogen atom, wherein $R^{11}$ and $R^{12}$ optionally together, form an alkylene bridge with 1, 2, 3, 4 or 5 C-atoms, especially a $C_1$–$C_3$-alkylene bridge under formation of a bicyclic ring system, G is selected from hydrogen, G1, G2, G3, G4 and G5, wherein G1 represents the residue

 (G1)

wherein
r is an integer from 1 to 3 or 0 and
s is 0 or 1,
$R^{13}$ is
selected from hydrogen, alkyl, especially $C_1$–$C_6$-alkyl, alkenyl with at least three C-atoms, especially $C_3$–$C_6$-alkenyl, alkinyl with at least three C-atoms, especially $C_3$–$C_6$-alkinyl, cycloalkyl with at least three C-atoms, especially $C_3$–$C_8$-cycloalkyl,
saturated, five to seven membered heterocycles, which can contain one or two hetero-atoms from the group N and/or S and/or O,
benzyl or phenyl,
monocyclic aromatic five or six-membered heterocycles, which can contain one to three hetero-atoms from the group N and/or S and/or O and are either bound directly or over a methylene group,
anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group,
$R^{14}$ has the same meaning as $R^{13}$, but is selected independently thereof,
$R^{15}$ is
selected from hydrogen, hydroxy, methyl, benzyl, phenyl,
monocyclic aromatic five- or six-membered heterocycles, which can contain one to three hetero-atoms selected from the group N and/or S and/or O and are either bound directly or over a methylene group,
anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, G2 is the residue

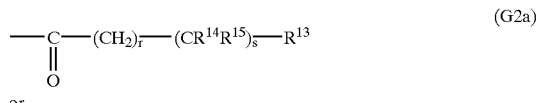 (G2a)

or

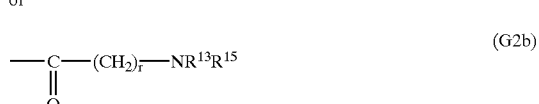 (G2b)

wherein the substituents $R^{13}$ and $R^{15}$ can have the above meaning or the grouping

—$NR^{13}R^{15}$ can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from the group N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue $$—SO_2—(CH_2)_r R^{13} \qquad (G3)$$

and
G4 is the residue

(G4)

wherein
$Ar^1$ and $Ar^2$ are selected independently from one another from phenyl, pyridyl or naphthyl and G5 is the residue $$—COR^{16} \qquad (G5)$$

wherein
$R^{16}$ is selected from trifluoromethyl, alkoxy, especially $C_1$–$C_6$-alkoxy, alkenyloxy, especially $C_3$–$C_6$-alkenyloxy, or benzyloxy, wherein any aryl residues and/or aromatic ring systems in the substituents $R^1$, $R^2$, $R^4$, $R^{13}$, $R^{14}$, $R^{15}$, $R^{16}$, $Ar^1$ and $Ar^2$ and/or in the ring system —$NR^{13}R^{15}$ can be substituted independently from each other by one to three of the same or different residues which are selected from halogen, cyano, alkyl, especially $C_1$–$C_6$-alkyl, trifluoromethyl, cycloalkyl, especially $C_3$–$C_8$-cycloalkyl, phenyl, benzyl, hydroxy, alkoxy, especially $C_1$–$C_6$-alkoxy, alkoxy, substituted entirely or partially by fluorine, substituted alkoxy, especially $C_1$–$C_6$-alkoxy, benzyloxy, phenoxy, mercapto, alkylthio, especially $C_1$–$C_6$-alkylthio, carboxy, alkoxycarbonyl, especially $C_1$–$C_6$-alkoxycarbonyl, benzyloxycarbonyl, nitro, amino, monoalkylamino, especially mono-$C_1$–$C_6$-alkylamino, dialkylamino, especially di-($C_1$–$C_6$-alkyl)-amino and methylenedioxy for two adjacent groups on the aromatic ring or ring system, wherein each of the residues alkyl, alkenyl, alkinyl, hydroxyalkyl, alkoxy, alkenyloxy, alkinyloxy, alkanoyloxy, alkoxycarbonyl, alkoxycarbonyloxy, alkylthio, alkenylthio, alkinylthio, alkylene, acyl, alkylsulfonyl, alkenylene, alkinylene, cycloalkyl, cycloalkyloxy, alkoxycarbonyl, alkylaminocarbonyl or dialkylaminocarbonyl of the substituents $R^1$ to $R^{14}$ can have 1 to 2 or 4, 6, 8, 10 or 12 C-atoms and/or 2 or 3 to 5, 7, 9, 11 or 13 and/or 15 C-atoms or 4, 5, 6, 7, 8, 9, 10, 11, 12, 13, 14 or 15 C-atoms depending on the structure, as well as stereoisomers and/or mixtures thereof and pharmacologically acceptable acid addition salts.

In another preferred embodiment of the invention the compounds of formula (II), disclosed in WO 97/48696 are not encompassed by the present invention:

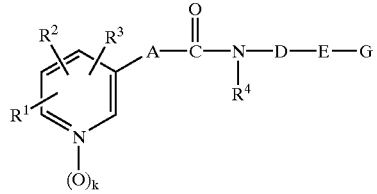

(II)

wherein
$R^1$ is
hydrogen, halogen, cyano, trifluoromethyl, hydroxy, benzyloxy, aminocarbonyl, carboxy, phenyl, phenoxy, phenylthio, pyridyloxy, pyridylthio, alkyl, especially $C_1$–$C_6$-alkyl, alkenyl, especially $C_3$–$C_6$-alkenyl, alkinyl, especially $C_3$–$C_6$-alkinyl, hydroxyalkyl, especially $C_1$–$C_6$-hydroxyalkyl, alkoxy, especially $C_1$–$C_6$-alkoxy, alkenyloxy, especially $C_3$–$C_6$-alkenyloxy, alkinyloxy, especially $C_3$–$C_6$-alkinyloxy, alkanoyloxy, especially $C_1$–$C_7$-alkanoyloxy, alkoxycarbonyloxy, especially $C_2$–$C_7$-alkoxycarbonyloxy, alkylthio, especially $C_1$–$C_6$-alkylthio, alkenylthio, especially $C_3$–$C_6$-alkenylthio, alkinylthio, especially $C_3$–$C_6$-alkinylthio, cycloalkyl, especially $C_3$–$C_8$-cycloalkyl, cycloalkyloxy, especially $C_3$–$C_8$-cycloalkyloxy, cycloalkylthio, especially $C_3$–$C_8$-cycloalkylthio, alkoxycarbonyl, especially $C_2$–$C_7$-alkoxycarbonyl, alkylaminocarbonyl, especially $C_2$–$C_7$-alkylaminocarbonyl, dialkylaminocarbonyl, especially $C_3$–$C_{13}$-dialkylaminocarbonyl, or
$NR^5R^6$, wherein
$R^5$ and
$R^6$ are selected independently of each other from hydrogen, alkyl, especially $C_1$–$C_6$-alkyl, alkenyl, especially $C_3$–$C_6$-alkenyl and alkinyl, especially $C_3$–$C_6$-alkinyl, $R^2$ is
hydrogen, halogen, cyano, hydroxy, trifluoromethyl, benzyloxy, alkyl, especially $C_1$–$C_6$-alkyl, alkoxy, especially $C_1$–$C_6$-alkoxy or alkanoyloxy, especially $C_1$–$C_7$-alkanoyloxy, wherein $R^1$ and $R^2$, if they are adjacent, optionally form a bridge which is selected from —$(CH_2)_4$—, —$(CH=CH)_2$— and —$CH_2O$—$CR^7R^8$—O—, wherein
$R^7$ and
$R^8$ are, independently of each other, hydrogen or alkyl, especially $C_1$–$C_6$-alkyl, $R^3$ is hydrogen, halogen, alkyl, especially $C_1$–$C_6$-alkyl, trifluoromethyl or hydroxyalkyl, especially $C_1$–$C_6$-hdroxyalkyl and $R^4$ is hydrogen, hydroxy, benzyloxy, alkyl, especially $C_1$–$C_6$-alkyl, alkenyl, especially $C_3$–$C_6$-alkenyl, alkinyl, especially $C_3$_$C_6$-alkinyl, cycloalkyl, especially $C_3$–$C_6$-cycloalkyl or alkoxy, especially $C_1$–$C_6$-alkoxy, k is 0 or 1,
A is
alkenylene with at least than two C-atoms, especially $C_2$–$C_6$-alkenylene, which is optionally substituted once to three-fold by $C_1$–$C_3$-alkyl, hydroxy, $C_1$–$C_3$-alkoxy, fluorine, cyano or phenyl, alkadienylene with at least four C-atoms, especially $C_4$–$C_6$-alkadienylene, which is optionally substituted once or twice by $C_1$–$C_3$-alkyl, fluorine, cyano or phenyl, 1,3,5-hexatrienylene, which is optionally substutited by $C_1$–$C_3$-alkyl, fluorine, cyano, or phenyl, ethinylene D is
- selected from alkylene, especially $C_1$–$C_{10}$-alkylene, optionally substituted once or twice by alkyl, especially $C_1$–$C_6$-alkyl, hydroxy, or alkoxy, especially $C_1$–$C_6$-alkoxy,
- alkenylene with at least two C-atoms, especially $C_2$–$C_{10}$-alkenylene, which is optionally substituted once or twice by alkyl, especially $C_1$–$C_6$-alkyl, hydroxy, or alkoxy, especially $C_1$–$C_6$-alkoxy, wherein the double bond can also be to ring E,
- alkinylene with at least three C-atoms, especially $C_3$–$C_{10}$-alkinylene, optionally substituted once or twice by alkyl, especially $C_1$–$C_6$-alkyl, hydroxy or alkoxy, especially $C_1$–$C_6$-alkoxy, and
- alkylene, especially $C_1$–$C_{10}$-alkylene, alkenylene with at least two C-atoms, especially $C_2$–$C_{10}$-alkenylene or alkinylene with at least three C-atoms, especially $C_3$–$C_{10}$-alkinylene, whereby one to three methylene units are each isosterically replaced by O, S, $NR^9$, CO, SO or $SO_2$ wherein
  - $R^9$ is selected from hydrogen, alkyl, especially $C_1$–$C_6$-alkyl, alkenyl, especially $C_3$–$C_6$-alkenyl, alkinyl, especially $C_3$–$C_6$-alkinyl, acyl, especially $C_1$–$C_6$-acyl or alkylsulfonyl, especially $C_1$–$C_6$-alkylsulfonyl,has the same meaning as E is selected from

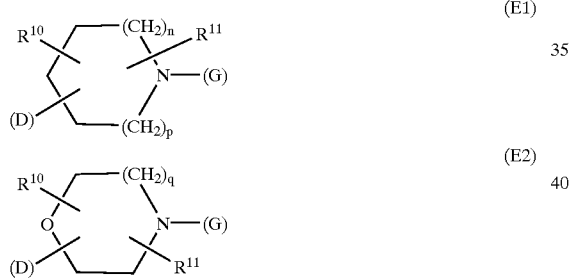

(E1)

(E2)

wherein the heterocyclic ring can also optionally have a double bond and n and p can be, independently of one another 0, 1, 2 or 3, with the proviso that n+p≦4 and q is 2 or 3, $R^{10}$ is hydrogen, alkyl, especially $C_1$–$C_6$-alkyl, hydroxy, hydroxymethyl, carboxy or alkoxycarbonyl with at least two C-atoms, especially $C_2$–$C_7$-alkoxycarbonyl and $R^{11}$ is hydrogen, alkyl, especially $C_1$–$C_6$-alkyl or or an oxo group adjacent to the nitrogen atom, wherein $R^{10}$ and $R^{11}$ optionally together, form an alkylene bridge with 1, 2, 3, 4 or 5 C-atoms, especially a $C_1$–$C_3$-alkylene bridge under formation of a bicyclic ring system, G is selected from hydrogen, G1, G2, G3, G4 and G5, wherein G1 represents the residue —(CH$_2$)$_r$—(CR$^{13}$R$^{14}$)$_s$—R$^{12}$ (G1)

wherein r is an integer from 1 to 3 or 0 and s is 0 or 1, $R^{12}$ is
- selected from hydrogen, alkyl, especially $C_1$–$C_6$-alkyl, alkenyl with at least three C-atoms, especially $C_3$–$C_6$-alkenyl, alkinyl with at least three C-atoms, especially $C_3$–$C_6$-alkinyl, cycloalkyl with at least three C-atoms, especially $C_3$–$C_8$-cycloalkyl,
- saturated, five to seven membered heterocycles, which can contain one or two hetero-atoms from the group N and/or S and/or O,
- benzyl or phenyl,
- monocyclic aromatic five or six-membered heterocycles, which can contain one to three hetero-atoms from the group N and/or S and/or O and are either bound directly or over a methylene group.
- anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
- anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, $R^{13}$ has the same meaning as $R^{12}$, but is selected independently thereof, $R^{14}$ is
- selected from hydrogen, hydroxy, methyl, benzyl, phenyl,
- monocyclic aromatic five- or six-membered heterocycles, which can contain one to three hetero-atoms selected from the group N and/or S and/or O and are either bound directly or over a methylene group,
- anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
- anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, G2 is the residue

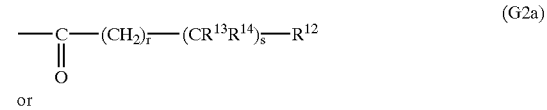

(G2a)

or

-continued

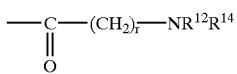  (G2b)

wherein the substituents $R^{12}$ and $R^{14}$ can have the above meaning or the grouping

—$NR^{12}R^{14}$ can also be a nitrogen heterocycle bound over the nitrogen atom, selected from
saturated or unsaturated monocyclic, four- to eight-membered heterocycles, which, aside from the essential nitrogen atom, can optionally contain one or two further hetero-atoms selected from the group N and/or S and/or O, or
saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue —$SO_2$—$(CH_2)_t$$R^{12}$  (G3)

and
G4 is the residue

  (G4)

wherein
$Ar^1$ and $Ar^2$ are selected independently from one another from phenyl, pyridyl or naphthyl and
G5 is the residue

—$COR^{15}$  (G5)

wherein
$R^{15}$ is
selected from trifluoromethyl, alkoxy, especially $C_1$–$C_6$-alkoxy, alkenyloxy, especially $C_3$–$C_6$-alkenyloxy, or benzyloxy,
wherein any aryl residues and/or aromatic ring systems in the substituents $R^1$, $R^2$, $R^4$, $R^{12}$, $R^{13}$, $R^{14}$, $R^{15}$, $Ar^1$ and $Ar^2$ and/or in the ring system —$NR^{12}R^{14}$ can be substituted independently from each other by one to three of the same or different residues which are selected from halogen, cyano, alkyl, especially $C_1$–$C_6$-alkyl, trifluoromethyl, cycloalkyl, especially $C_3$–$C_8$-cycloalkyl, phenyl, benzyl, hydroxy, alkoxy, especially $C_1$–$C_6$-alkoxy, alkoxy, substituted entirely or partially by fluorine, substituted alkoxy especially $C_1$–$C_6$-alkoxy, benzyloxy, phenoxy, mercapto, alkylthio, especially $C_1$–$C_6$-alkylthio, carboxy, alkoxycarbonyl, especially $C_1$–$C_6$-alkoxycarbonyl, benzyloxycarbonyl, nitro, amino, monoalkylamino, especially mono-$C_1$–$C_6$-alkylamino, dialkylamino, especially di-($C_1$–$C_6$-alkyl)-amino and methylenedioxy for two adjacent groups on the aromatic ring or ring system,
wherein each of the residues alkyl, alkenyl, alkinyl, hydroxyalkyl, alkoxy, alkenyloxy, alkinyloxy, alkanoyloxy, alkoxycarbonyl, alkoxycarbonyloxy, alkylthio, alkenylthio, alkinylthio, alkylene, acyl, alkylsulfonyl, alkenylene, alkinylene, cycloalkyl, cycloalkyloxy, alkoxycarbonyl, alkylaminocarbonyl or dialkylaminocarbonyl of the substituents $R^1$ to $R^{15}$ can have 1 to 2 or 4, 6, 8, 10 or 12 C-atoms and/or 2 or 3 to 5, 7, 9, 11 or 13 and/or 15 C-atoms or 4, 5, 6, 7, 8, 9, 10, 11, 12, 13, 14 or 15 C-atoms depending on the structure, as well as
stereoisomers and/or mixtures thereof and pharmacologically acceptable acid addition salts
with the exception of (E)-3-(3-piridyl)-N-[2-(1-benzylpiperidin-4-yl)ethyl]-2-propenamide hydrochloride.

In a further preferred embodiment of the invention the compounds of formula (III), disclosed in WO 97/48397 are not encompassed by the present invention:

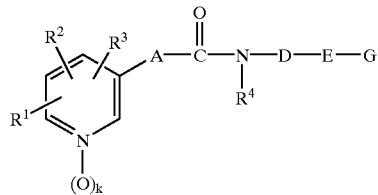  (III)

wherein
$R^1$ is
hydrogen, halogen, cyano, trifluoromethyl, hydroxy, benzyloxy, aminocarbonyl, carboxy, phenyl, phenoxy, phenylthio, pyridyloxy, pyridylthio, alkyl, especially $C_1$–$C_6$-alkyl, alkenyl, especially $C_3$–$C_6$-alkenyl, alkinyl, especially $C_3$–$C_6$-alkinyl, hydroxyalkyl, especially $C_1$–$C_6$-hydroxyalkyl, alkoxy, especially $C_1$–$C_6$-alkoxy, alkenyloxy, especially $C_3$–$C_6$-alkenyloxy, alkinyloxy, especially $C_3$–$C_6$-alkinyloxy, alkanoyloxy, especially $C_1$–$C_7$-alkanoyloxy, alkoxycarbonyloxy, especially $C_2$–$C_7$-alkoxycarbonyloxy, alkylthio, especially $C_1$–$C_6$-alkylthio, alkenylthio, especially $C_3$–$C_6$-alkenylthio, alkinylthio, especially $C_3$–$C_6$-alkinylthio, cycloalkyl, especially $C_3$–$C_8$-cycloalkyl, cycloalkyloxy, especially $C_3$–$C_8$-cycloalkyloxy, cycloalkylthio, especially $C_3$–$C_8$-cycloalkylthio, alkoxycarbonyl, especially $C_2$–$C_7$-alkoxycarbonyl, alkylaminocarbonyl, especially $C_2$–$C_7$-alkylaminocarbonyl, dialkylaminocarbonyl, especially $C_3$–$C_{13}$-dialkylaminocarbonyl, or
$NR^5R^6$, wherein
$R^5$ and
$R^6$ are selected independently of each other from hydrogen, alkyl, especially $C_1$–$C_6$-alkyl, alkenyl, especially $C_3$–$C_6$-alkenyl and alkinyl, especially $C_3$–$C_6$-alkinyl,
$R^2$ is
hydrogen, halogen, cyano, hydroxy, trifluoromethyl, benzyloxy, alkyl, especially $C_1$–$C_6$-alkyl, alkoxy, especially $C_1$–$C_6$-alkoxy or alkanoyloxy, especially $C_1$–$C_7$-alkanoyloxy,
wherein $R^1$ and $R^2$, if they are adjacent, optionally form a bridge which is selected from —$(CH_2)_4$—, —$(CH=CH)_2$— and —$CH_2O$—$CR^7R^8$—$O$—, wherein
$R^7$ and
$R^8$ are, independently of each other, hydrogen or alkyl, especially $C_1$–$C_6$-alkyl,
$R^3$ is hydrogen, halogen, alkyl, especially $C_1$–$C_6$-alkyl, trifluoromethyl or hydroxyalkyl, especially $C_1$–$C_6$-hdroxyalkyl and R⁴ is hydrogen, hydroxy, benzyloxy, alkyl, especially $C_1$–$C_6$-alkyl, alkenyl, especially $C_3$–$C_6$-alkenyl, alkinyl, especially $C_3$–$C_6$-alkinyl, cycloalkyl, especially $C_3$–$C_6$-cycloalkyl or alkoxy, especially $C_1$–$C_6$-alkoxy, k is 0 or 1, A is
- alkylene, especially $C_1$–$C_6$-alkylene, which is optionally substituted once to three-fold by alkyl, especially $C_1$–$C_3$-alkyl, hydroxy, alkoxy, especially $C_1$–$C_3$-alkoxy, fluorine or phenyl, or
- 1,2-cyclopropylene or
- alkenylene with at least than two C-atoms, especially $C_2$–$C_6$-alkenylene, which is optionally substituted once to three-fold by $C_1$–$C_3$-alkyl, hydroxy, $C_1$–$C_3$-alkoxy, fluorine, cyano or phenyl,
- alkadienylene with at least four C-atoms, especially $C_4$–$C_6$-alkadienylene, which is optionally substituted once or twice by $C_1$–$C_3$-alkyl, fluorine, cyano or phenyl,
- 1,3,5-hexatrienylene, which is optionally substutited by $C_1$–$C_3$-alkyl, fluorine, cyano, or phenyl,
- ethinylene or
- alkylene with at least two C-atoms, especially $C_2$–$C_6$-alkylene in which a methylene unit can be isosterically replaced by O, S, $NR^9$, CO, SO or $SO_2$, wherein the substitution, with the exception of =CO, cannot be adjacent to the amide group and wherein
   $R^9$ is selected from hydrogen, alkyl, especially $C_1$–$C_6$-alkyl, alkenyl, especially $C_3$–$C_6$-alkenyl, alkinyl, especially $C_3$–$C_6$-alkinyl, acyl, especially $C_1$–$C_6$-acyl or alkylsulfonyl, especially $C_1$–$C_6$-alkylsulfonyl, D is
- selected from alkylene, especially $C_1$–$C_{10}$-alkylene, optionally substituted once or twice by alkyl, especially $C_1$–$C_6$-alkyl, hydroxy, or alkoxy, especially $C_1$–$C_6$-alkoxy,
- alkenylene with at least two C-atoms, especially $C_2$–$C_{10}$-alkenylene, which is optionally substituted once or twice by alkyl, especially $C_1$–$C_6$-alkyl, hydroxy, or alkoxy, especially $C_1$–$C_6$-alkoxy, wherein the double bond can also be to ring E,
- alkinylene with at least three C-atoms, especially $C_3$–$C_{10}$-alkinylene, optionally substituted once or twice by alkyl, especially $C_1$–$C_6$-alkyl, hydroxy or alkoxy, especially $C_1$–$C_6$-alkoxy, and
- alkylene, especially $C_1$–$C_{10}$-alkylene, alkenylene with at least two C-atoms, especially $C_2$–$C_{10}$-alkenylene or alkinylene with at least three C-atoms, especially $C_3$–$C_{10}$-alkinylene, whereby one to three methylene units are each isosterically replaced by O, S, $NR^{10}$, CO, SO or $SO_2$ wherein
   $R^{10}$ has the same meaning as $R^9$ but is selected independently thereof, E is selected from

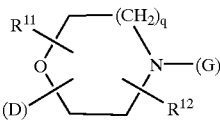 (E1)

or

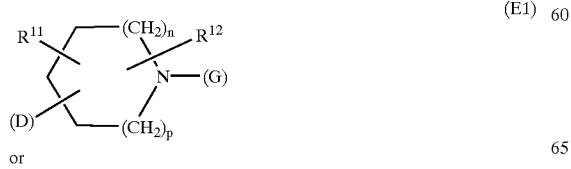 (E2)

wherein the heterocyclic ring can also optionally have a double bond and n and p can be, independently of one another 0, 1, 2 or 3, with the proviso that $n+p \leq 4$ and q is 2 or 3, $R^{11}$ is hydrogen, alkyl, especially $C_1$–$C_6$-alkyl, hydroxy, hydroxymethyl, carboxy or alkoxycarbonyl with at least two C-atoms, especially $C_2$–$C_7$-alkoxycarbonyl and $R^{12}$ is hydrogen, alkyl, especially $C_1$–$C_6$-alkyl or or an oxo group adjacent to the nitrogen atom, wherein $R^{11}$ and $R^{12}$ optionally together, form an alkylene bridge with 1, 2, 3, 4 or 5 C-atoms, especially a $C_1$–$C_3$-alkylene bridge under formation of a bicyclic ring system, G is selected from hydrogen, G1, G2, G3, G4 and G5, wherein G1 represents the residue $$—(CH_2)_r—(CR^{14}R^{15})_s—R^{13} \qquad (G1)$$

wherein r is an integer from 1 to 3 or 0 and s is 0 or 1, $R^{13}$ is
- selected from hydrogen, alkyl, especially $C_1$–$C_6$-alkyl, alkenyl with at least three C-atoms, especially $C_3$–$C_6$-alkenyl, alkinyl with at least three C-atoms, especially $C_3$–$C_6$-alkinyl, cycloalkyl with at least three C-atoms, especially $C_3$–$C_8$-cycloalkyl,
- saturated, five to seven membered heterocycles, which can contain one or two hetero-atoms from the group N and/or S and/or O,
- benzyl or phenyl,
- monocyclic aromatic five or six-membered heterocycles, which can contain one to three hetero-atoms from the group N and/or S and/or O and are either bound directly or over a methylene group,
- anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
- anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, $R^{14}$ has the same meaning as $R^{13}$, but is selected independently thereof, $R^{15}$ is selected from hydrogen, hydroxy, methyl, benzyl, phenyl, monocyclic aromatic five- or six-membered heterocycles, which can contain one to three hetero-atoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, G2 is the residue

  (G2a)

or

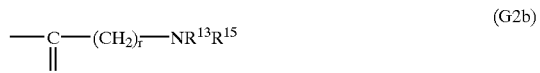  (G2b)

wherein the substituents $R^{13}$ and $R^{15}$ can have the above meaning or the grouping

can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from the group N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue

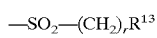  (G3)

and
G4 is the residue

  (G4)

wherein
Ar¹ and Ar² are selected independently from one another from phenyl, pyridyl or naphthyl and G5 is the residue

  (G5)

wherein
$R^{16}$ is selected from trifluoromethyl, alkoxy, especially $C_1$–$C_6$-alkoxy, alkenyloxy, especially $C_3$–$C_6$-alkenyloxy, or benzyloxy, wherein any aryl residues and/or aromatic ring systems in the substituents $R^1$, $R^2$, $R^4$, $R^{13}$, $R^{14}$, $R^{15}$, $R^{16}$, Ar¹ and Ar² and/or in the ring system —$NR^{13}R^{15}$ can be substituted independently from each other by one to three of the same or different residues which are selected from halogen, cyano, alkyl, especially $C_1$–$C_6$-alkyl, trifluoromethyl, cycloalkyl, especially $C_3$–$C_8$-cycloalkyl, phenyl, benzyl, hydroxy, alkoxy, especially $C_1$–$C_6$-alkoxy, alkoxy, substituted entirely or partially by fluorine, substituted alkoxy, especially $C_1$–$C_6$-alkoxy, benzyloxy, phenoxy, mercapto, alkylthio, especially $C_1$–$C_6$-alkylthio, carboxy, alkoxycarbonyl, especially $C_1$–$C_6$-alkoxycarbonyl, benzyloxycarbonyl, nitro, amino, monoalkylamino, especially mono-$C_1$–$C_6$-alkylamino, dialkylamino, especially di-($C_1$–$C_6$-alkyl)-amino and methylenedioxy for two adjacent groups on the aromatic ring or ring system, wherein each of the residues alkyl, alkenyl, alkinyl, hydroxyalkyl, alkoxy, alkenyloxy, alkinyloxy, alkanoyloxy, alkoxycarbonyl, alkoxycarbonyloxy, alkylthio, alkenylthio, alkinylthio, alkylene, acyl, alkylsulfonyl, alkenylene, alkinylene, cycloalkyl, cycloalkyloxy, alkoxycarbonyl, alkylaminocarbonyl or dialkylaminocarbonyl of the substituents $R^1$ to $R^{14}$ can have 1 to 2 or 4, 6, 8, 10 or 12 C-atoms and/or 2 or 3 to 5, 7, 9, 11 or 13 and/or 15 C-atoms or 4, 5, 6, 7, 8, 9, 10, 11, 12, 13, 14 or 15 C-atoms depending on the structure, as well as stereoisomers and/or mixtures thereof and pharmacologically acceptable acid addition salts thereof.

In a further preferred embodiment of the invention the compounds of formula (IV), disclosed in WO 99/31063 are not encompassed by the present invention:

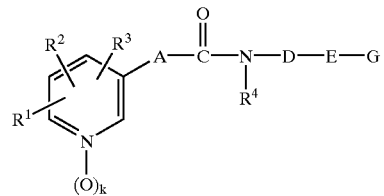  (IV)

wherein
$R^1$ is selected from
hydrogen, hydroxy, halogen, cyano, aminocarbonyl, carboxy, saturated, single or several-fold unsaturated, branched or straight chained or cyclic hydrocarbon residues such as alkyl, alkenyl, alkinyl or cycloalkyl, aryl such as phenyl or heteroaryl such as pyridyl, alkoxy, cycloalkyloxy, alkenyloxy or alkinyloxy or aralkyloxy such as the benzyloxy group, alkoxycarbonyl, alkylaminocarbonyl, dialkylaminocarbonyl, alkanoyloxy, alkoxycarbonyloxy, alkylthio, cycloalkylthio, alkenylthio, alkinylthio, aryloxy such as phenoxy, heteroaryloxy such as pyridyloxy, arylthio such as phenylthio, heteroarylthio such as pyridylthio, trifluoromethyl,
hydroxyalkyl,
$NR^5R^6$, wherein $R^5$ and $R^6$ are selected independent of each other from hydrogen, saturated or unsaturated hydrocarbon residues such as alkyl, alkenyl, alkinyl, or aryl such as phenyl and aralkyl such as benzyl;

$R^2$ is selected from hydrogen, halogen, cyano, saturated hydrocarbon residues such as alkyl, or halogenated hydrocarbon residues such as trifluoromethyl, hydroxy, alkoxy, aralkyloxy residues such as benzyloxy, as well as alkanoyloxy, whereby $R^1$ and $R^2$, in the case that they are immediately adjacent to each other, optionally form a bridge which is selected from —(CH$_2$)$_4$— and —(CH=CH)$_2$— and —CH$_2$O—CR$^7$R$^8$—O—, wherein $R^7$ and $R^8$ are selected independently of each other from hydrogen and alkyl residues;

$R^3$ is selected from Hydrogen, halogen, saturated hydrocarbon residues such as alkyl, or halogenated hydrocarbon residues such as trifluoromethyl, or hydroxyalkyl;

$R^4$ is selected from hydrogen, hydroxy, or single or several-fold unsaturated, branched or straight chained or cyclic hydrocarbon residues such as alkyl, alkenyl, alkinyl or cycloalkyl, alkoxy and aralkyloxy such as benzyloxy;

k is 0 or 1;

A is selected from

Alkylene, which is optionally substituted one to three-fold by straight chained or branched chained hydrocarbon residues such as alkyl, hydroxy, alkoxy, halogen such as fluorine, or aryl such as phenyl, Alkylene, wherein a methylene unit is isosterically replaced by O, S, NR$^9$, CO, SO or SO$_2$ whereby, with the exception of CO, the isosteric substitution cannot be adjacent to the amide group and, in NR$^9$, the residue R$^9$ is selected from hydrogen, alkyl, alkenyl, alkinyl, acyl or alkanesulfonyl;

Cycloalkylene such as 1,2-cyclopropylene;

Alkenylene which is optionally substituted one to three-fold by alkyl, hydroxy, alkoxy, fluorine cyano or aryl such as phenyl;

Alkadienylene, which is optionally substituted once or twice-fold by alkyl, fluorine, cyano or aryl such as phenyl, 1,3,5-hexatrienylene, which is optionally substituted by alkyl, fluorine, cyano or aryl such as phenyl, and ethinylene;

D is selected from alkylene, which is optionally substituted once or twice by alkyl, hydroxy, or alkoxy;

alkenylene, which is optionally substituted once or twice by alkyl, hydroxy, or alkoxy;

alkinylene, which is optionally substituted once or twice by alkyl, hydroxy, or alkoxy, as well as alkylene, alkenylene or alkinylene, wherein one to three methylene units is each isosterically replaced by O, S, NR$^{10}$, CO, SO or SO$_2$, wherein R$^{10}$ has the same meaning as R$^9$ but is selected independently thereof;

E is

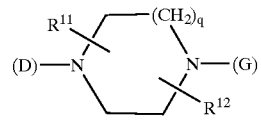

whereby q is 1, 2 or 3;

$R^{11}$ is selected from hydrogen, alkyl, hydroxy, hydroxymethyl, carboxy, or alkoxycarbonyl and $R^{12}$ is selected from hydrogen, alkyl or an oxo group immediately adjacent to a nitrogen atom or $R^{11}$ and $R^{12}$ optionally together, form an alkylene bridge under formation of a bicyclic ring systems;

G is selected from G1, G2, G3, G4 or G5, wherein G$^1$ is

 (G1)

whereby r has the meaning 0 to 3, s is 0 or 1;

$R^{13}$ is selected from hydrogen, alkyl, alkenyl, alkinyl, cycloalkyl; saturated or unsaturated, four to eight-membered heterocycles which can contain one or two hetero-atoms that are selected from N and/or S and /or O; benzyl, phenyl;

monocyclic aromatic five- or six-membered heterocycles which can contain 1 to 3 hetero-atoms that are selected from N and/or S and/or O and are either directly bound or bound over a methelyene group;

anellated bi- and tricyclic aromatic or partially hydrated carbocyclic ring systems with 8 to 16 ring atoms and at least one aromatic ring, whereby the bond can occur either over an aromatic or a hydrated ring and either directly or over a methylene group;

anellated bi- and tricyclic aromatic or partially hydrated heterocyclic ring systems with 8 to 16 ring atoms and at least one aromatic ring, whereby one to three ring atoms can be selected from N and/or S and/or O and the bond can occur either over an aromatic or a hydrated ring and either directly or over a methylene group;

$R^{14}$ has the same meaning as $R^{13}$ but is selected independently thereof;

$R^{15}$ is selected from hydrogen, hydroxy, C$_1$–C$_3$-alkyl, aralkyl such as benzyl or aryl such as phenyl, monocyclic aromatic five or six-membered heterocycles, which can contain one to three hetero-atoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, with the exception of compounds in which G has the meaning —(CH$_2$)$_r$—(CR$^{14}$R$^{15}$)$_s$—R$^{13}$ (G1)

in the case that the following substitutents are simultaneously signify

R$^{13}$ pyridyl or (optionally halogen-, alkyl-, alkoxy- or Trifluoromethyl-substituted) phenyl, R$^{14}$ hydrogen or (phenyl optionally substituted with halogen-, alkyl-, alkoxy- or Trifluoro methyl, R$^{15}$ is hydrogen, and A represents alkylene, optionally substituted ethenylene or butadienylene, D alkylene or alkenylene as well as E piperazine or homopiperazine and s=1;

G$^2$ is selected from

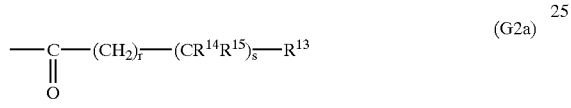
(G2a)

or

(G2b)

whereby r and s as well as the substitutents R$^{13}$ to R$^{15}$ can have the above meaning, or the grouping

—NR$^{13}$R$^{15}$ can also be a nitrogen heterocycle bound over the nitrogen atom selected from saturated or unsaturated monocyclic, four to eight-membered heterocycles, which, aside from the essential nitrogen atom, can still optionally contain one or two further hetero-atoms selected from N and/or S and/or O, or saturated or unsaturated bi- or tricyclic, anellated or bridged heterocycles with 8 to 16 ring atoms, that aside from the essential nitrogen atom, can optionally still contain one or two further hetero-atoms that are selected from N and/or S and/or O;

G$^3$ has the meaning

—SO$_2$—(CH$_2$)$_r$—R$^{13}$ (G3)

wherein r and R$^{13}$ have the above definition,

G$^4$ has the meaning

(G4)

whereby

Ar$^1$ and Ar$^2$ can be selected independently from each other from phenyl, pyridyl or naphthyl;

G$^5$ has the meaning

—COR$^{16}$ (G5)

whereby

R$^{16}$ is selected from trifluoromethyl, alkoxy, alkenyloxy, and aralkyloxy such as benzyloxy, whereby aromatic ring systems in the substitutents R$^1$, R$^2$, R$^4$, R$^5$, R$^6$, R$^{13}$, R$^{14}$, R$^{15}$, R$^{16}$, Ar$^1$ and Ar$^2$ and/or in the ring system —NR$^{13}$R$^{15}$ can be substituted independently from each other by one to three of the same or different groups selected from halogen, cyano, alkyl, halogen alkyl such as trifluoromethyl, cycloalkyl, aryl such as phenyl, arylalkyl such as benzyl; hydroxy, hydroxy alkyl, alkoxy, alkoxy entirely or partially substituted by fluorine, aralkyloxy such as benzyloxy, aryloxy such as phenoxy; mercapto, alkylthio, carboxy, carboxyalkyl, carboxyalkenyl, alkoxycarbonyl, aralkyloxycarbonyl such as benzyloxycarbonyl, nitro, amino, monoalkylamino, dialkylamino and in the case of two adjacent residues on the aromatic ring, also methylendioxy, and whereby alkyl-, alkenyl- and cycloalkyl residues in the groups G$^1$, G$^2$ and G$^3$ can be substituted by one or two of the same or different groups which are selected from hydroxy, carboxy, alkoxycarbonyl, aralkyloxycarbonyl such as benzyloxycarbonyl, amino, monoalkylamino and dialkylamino;

their cis- and trans-isomers, E- and Z-isomers, especially in case that A is a cyclopropane ring or D contains one or more double bonds, including the enantiomers, diastereomers and other isomers as well as their racemic or non-racemic mixtures and the corresponding endo- and exo-isomers for the case that the ring system E is bicyclic;

their tautomeres;

their acid addition salts including their hydrates and solvates.

The compounds of formula (V), disclosed in WO 99/31060, in a preferred embodiment of the invention are not encompassed by the present invention:

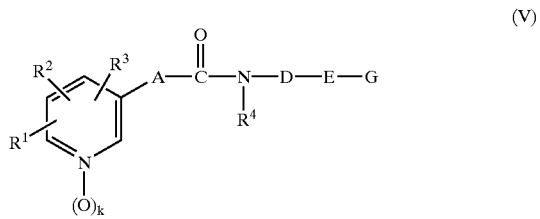
(V)

wherein

R$^1$ is selected from hydrogen, hydroxy, halogen, cyano, carboxy; saturated, single or several-fold unsaturated, branched or straight chained or cyclic hydrocarbon residues such as alkyl, alkenyl, alkinyl or cycloalkyl; trifluoromethyl or hydroxyalkyl;

aryl such as phenyl or heteroaryl such as pyridyl; alkoxy, cycloalkyloxy, alkenyloxy, alkinyloxy or aralkyloxy such as the benzyloxy group, alkoxycarbonyl; aminocarbonyl, alkylaminocarbonyl, dialkylaminocarbonyl, alkanoyloxy, alkoxycarbonyloxy;

alkylthio, cycloalkylthio, alkenylthio, alkinylthio;
aryloxy such as phenoxy, heteroaryloxy such as pyridyloxy, heteroarylthio such as pyridylthio, and $NR^5R^6$, whereby
$R^5$ and $R^6$ are selected independent of each other from hydrogen, saturated or unsaturated hydrocarbon residues such as alkyl, alkenyl, alkinyl, or aryl such as phenyl and aralkyl such as benzyl;
$R^2$ is selected from
hydrogen, halogen, cyano, saturated hydrocarbon residues such as alkyl, or halogenated hydrocarbon residues such as trifluoromethyl, hydroxy, alkoxy, aralkyloxy residues such as benzyloxy, as well as alkanoyloxy,
whereby $R^1$ and $R^2$, in the case that they are immediately adjacent to each other, optionally form a bridge which is selected from —$(CH_2)_4$— and —$(CH=CH)_2$— and —$CH_2O$—$CR^7R^8$—$O$—, wherein
$R^7$ and $R^8$ are selected independently of each other from hydrogen and alkyl residues;
$R^3$ is selected from hydrogen, halogen, saturated hydrocarbon residues such as alkyl, or halogenated hydrocarbon residues such as trifluoromethyl, or hydroxyalkyl;
$R^4$ is selected from hydrogen, hydroxy, saturated, single or several-fold unsaturated, branched or straight chained or cyclic hydrocarbon residues such as alkyl, alkenyl, alkinyl or cycloalkyl, alkoxy and aralkyloxy such as benzyloxy;
k is 0 or 1;
A is selected from alkylene with at least 2 carbon atoms which is optionally substituted one to three-fold by straight chained or branched chained hydrocarbon residues such as alkyl, hydroxy, alkoxy, halogen such as fluorine, or aryl such as phenyl,
alkylene with at least 2 carbon atoms, wherein a methylene unit is isosterically replaced by O, S, $NR^9$, CO, SO or $SO_2$ whereby, with the exception of CO, the isosteric substitution cannot be adjacent to the amide group and, in $NR^9$, the residue $R^9$ is selected from hydrogen, alkyl, alkenyl, alkinyl, acyl or alkanesulfonyl;
cycloalkylene such as 1,2-cyclopropylene;
alkenylene with at least 2 carbon atoms which is optionally substituted one to three-fold by alkyl, hydroxy, alkoxy, fluorine, cyano or aryl such as phenyl;
alkadienylene with at least 4 carbon atoms, which is optionally substituted once or twice by alkyl, fluorine, cyano or aryl such as phenyl;
1,3,5-hexatrienylene, which is optionally substituted by alkyl, fluorine, cyano or aryl such as phenyl; as well as ethinylene;
D is selected from
alkylene with at least 2 carbon atoms, which is optionally substituted once or twice by alkyl, hydroxy, or alkoxy;
alkenylene with at least 4 carbon atoms, which is optionally substituted once or twice by alkyl, hydroxy, or alkoxy;
alkinylene with at least 4 carbon atoms, which is optionally substituted once or twice by alkyl, hydroxy, or alkoxy; as well as
alkylene, alkenylene or alkinylene with at least 2 or 4 carbon atoms respectively, wherein one to three methylene units is each isosterically replaced by O, S, $NR^{10}$, CO, SO or $SO_2$, wherein
$R^{10}$ has the same meaning as $R^9$ but is selected independently thereof;

E is selected from

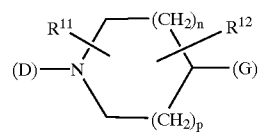

(E1)

and

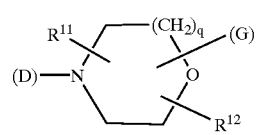

(E2)

whereby the heterocyclic ring can optionally have a double bond and
n and p can be, independent of each other, 0, 1, 2 or 3 with the proviso that n+p≦4.
q is 1, 2 or 3;
$R^{11}$ is selected from hydrogen, alkyl, hydroxy, hydroxymethyl, carboxy, or alkoxycarbonyl with at least 2 carbon atoms; and
$R^{12}$ is selected from hydrogen, alkyl or an oxo group adjacent to a nitrogen atom; or
$R^{11}$ and $R^{12}$, optionally together, form a $C_1$–$C_3$-alkylene bridge under formation of a bicyclic ring system;
G is selected from G1, G2, G3, G4 or G5, wherein
$G^1$ is the residue

(G1)

and
r is a number from 0 to 3 and
s is 0 or 1;
$R^{13}$ is selected from
hydrogen, alkyl, or alkenyl, alkinyl, cycloalkyl with at least 3 carbon atoms in the saturated or cyclic residues; saturated or unsaturated, four to seven-membered heterocycles which can contain one or two hetero-atoms selected from N and/or S and/or O; benzyl, phenyl;
monocyclic aromatic five- or six-membered heterocycles which can contain 1 to 3 hetero-atoms selected from N and/or S and/or O and are either directly bound or bound over a methelyene group;
anellated bi- and tricyclic aromatic or partially hydrated carbocyclic ring systems with 8 to 18, preferably up to 16 ring atoms, and at least one aromatic ring, whereby the linkage can occur either over an aromatic or a hydrated ring and either directly or over a methylene group;
anellated bi- and tricyclic aromatic or partially hydrated heterocyclic ring systems with 8 to 18, preferably up to 16 ring atoms, and at least one aromatic ring, whereby one to three ring atoms can be selected from N and/or S and/or O and the linkage can occur either over an aromatic or a hydrated ring and either directly or over a methylene group;
$R^{14}$ has the same meaning as $R^{13}$ but is selected independently thereof;
$R^{15}$ is selected from
hydrogen, hydroxy, methyl, benzyl, phenyl;
monocyclic aromatic five or six-membered heterocycles, which can contain one to three hetero-atoms selected from the group N and/or S and/or O and are either bound directly or over a methylene group;

anellated bi- and tricyclic aromatic or partially hydrated carbocyclic ring systems with 8 to 18, preferably up to 16 ring atoms, and at least one aromatic ring, wherein the linkage can occur either over an aromatic or a hydrated ring and either directly or over a methylene group;

anellated bi- and tricyclic aromatic or partially hydrated heterocyclic ring systems with 8 to 18, preferably up to 16 ring atoms, and at least one aromatic ring, wherein one to three ring atoms can be selected from N and/or S and/or O and the linkage can occur either over an aromatic ring or a hydrated ring and either directly or over a methylene group;

$G^2$ has the meaning

  (G2), whereby
$R^{13}$ and $R^{15}$ have the above meaning and
u represents the number 0 or 1 or signifies the residue

which is bound by means of a double bond to E in the case that u=1, or can signify a ring system bound over the carbon atom selected from cycloalkyl with at least 3 carbon atoms; saturated, tour to seven-membered heterocycles which can contain one or two hetero-atoms selected from N and/or S and/or O;

anellated bi- and tricyclic partially hydrated carboxocyclic ring system with 8 to 18, preferably up to 16 ring atoms, and at least one aromatic ring;

anellated bi- and tricyclic partially hydrated heterocyclic ring systems with 8 to 18, preferably up to 16 ring atoms, and at least one aromatic ring, wherein one to three ring atoms can be selected from N and/or S and/or O;

or, in the case that u=0, the two germinal substituents $R^{13}$ and $R^{15}$ can form a spirocycle together with the bonding atom of the ring E selected from cycloalkyl, saturated, four to seven-membered heterocycles which can contain one or two hetero-atoms selected from N and/or S and/or O;

anellated bi- and tricyclic partially hydrated carbocyclic ring systems with 8 to 18, preferably 16 ring atoms, and at least one aromatic ring;

anellated bi- and tricyclic partially hydrated heterocyclic ring systems with 8 to 18, preferably up to 16 ring atoms, and at least one aromatic ring, whereby one to three ring atoms can be selected from N and/or S and/or O;

$G^3$ is selected from

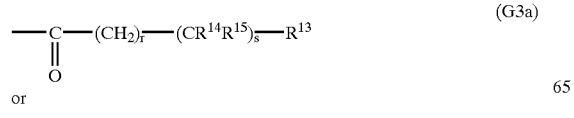

or

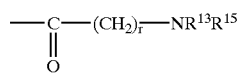 (G3b)

whereby r and s as well as the substituents $R^{13}$, $R^{14}$ and $R^{15}$ can have the above meanings, or the grouping

can also be a nitrogen heterocycle bound over the nitrogen atom selected from
saturated or unsaturated monocyclic, four to eight-heterocycles which, aside from the essential nitrogen atom, can optionally further contain one or two further hetero-atoms selected from N and/or S and/or O,
saturated or unsaturated bi- or tricyclic, anellated or bridged heterocycles with 8 to 18, preferably up to 16 ring atoms, which, aside from the essential nitrogen atom, can optionally contain one or two further hetero-atoms selected from N and/or S and/or O;

$G^4$ has the meaning

 (G4a)

or

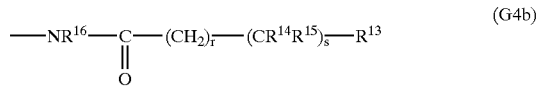 (G4b)

or

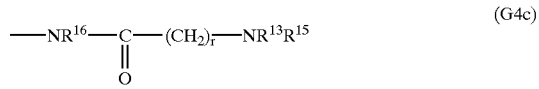 (G4c)

or

 (G4d)

or

 (G4e)

or

 (G4f)

whereby r and s as well as the substituents $R^{13}$, $R^{14}$ and $R^{15}$ can have the above meanings and
$R^{16}$ has the same meanings as $R^5$, but is selected independently thereof,
$R^{17}$ is selected from trifluoromethyl, alkoxy, alkenyloxy with at least 3 carbon atoms; or benzyloxy; and
$Ar^1$ and $Ar^2$, are selected independently from each other from phenyl, pyridyl or naphthyl;

$G^5$ has the meaning

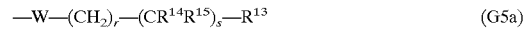 (G5a)

or

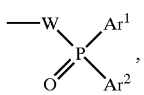  (G5b)

whereby r and s as well as the substitutents $R^{13}$, $R^{14}$, $R^{15}$, $Ar^1$ and $Ar^2$ can have the above meanings and W is O or S, whereby the ring systems $=CR^{13}R^{15}$, $-NR^{13}R^{15}$ and optionally $ER^{13},R^{15}$ as well as aromatic ring systems in the substituents $R^1$, $R^2$, $R^4$, $R^5$, $R^6$, $R^{13}$, $R^{14}$, $R^{15}$, $R^{16}$, $R^{17}$, $Ar^1$ and $Ar^2$ can be substituted independently from each other by one to three of the same or different groups selected from halogen, cyano, alkyl, trifluoromethyl, cycloalkyl with at least 3 carbon atoms, phenyl, benzyl, hydroxy, hydroxyalkyl, alkoxy, alkoxy entirely or partially substituted by fluorine, benzyloxy, phenoxy, mercapto, alkylthio, carboxy, carboxyalkyl, carboxyalkenyl with at least 2 carbon atoms or alkoxycarbonyl with at least 2 carbon atoms, benzyloxycarbonyl, nitro, amino, monoalkylamino, dialkylamino and, for two adjacent residues on the aromatic ring, methylenedioxy, and whereby alkyl-, alkenyl- and cycloalkyl residues in the groups $G^1$ to $G^5$ can be substituted by one or two of the same or different groups selected from hydroxy, carboxy, alkoxycarbonyl with at least 2 carbon atoms, benzyloxycarbonyl, amino, monoalkylamino and dialkylamino, whereby G cannot signify the residue

 $-CHR^{14}-R^{13}$ or

 $-C(OH)R^{14}-R^{13}$ or

 $=CR^{13}R^{15}$ or

 $-O-CHR^{14}-R^{13}$ in the case when simultaneously
$R^{13}$ is hydrogen, alkyl or phenyl optionally substituted by halogen, alkyl, hydroxy, alkoxy or trifluoromethyl
$R^{14}$ and/or $R^{15}$ is pyridyl or phenyl optionally substituted with halogen, alkyl, hydroxy, alkoxy or trifluoromethyl,
A is alkylene, optionally substituted ethenylene or butadienylene,
D is alkylene and
E is piperidine substituted in the 4-position;
the cis- and trans-isomers, E- and Z-isomers of the above defined compounds, especially in case that A is a cyclopropane ring or D contains one or more double bonds, including the enantiomers, diastereomers and other isomers of the above defined compounds as well as their racemic or non-racemic mixtures as well as the pure endo- and/or exo-isomers of the above defined compounds as well as their mixtures;

the respective tautomeric compounds;

and the acid addition salts of the above defined compounds including their hydrates and solvates.

The compounds of formula (VI), disclosed in WO 99/31087, in a further preferred embodiment of the invention, are not encompassed by the present invention:

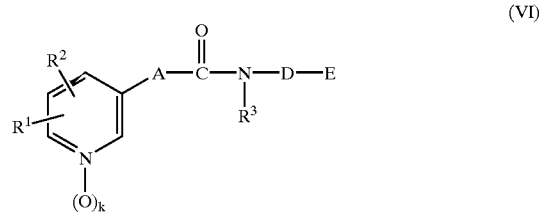  (VI)

wherein the substituents have the following meanings:
$R^1$ is selected from hydrogen, halogen, cyano, alkyl, alkenyl, alkinyl, trifluoromethyl, cycloalkyl, hydroxyalkyl, hydroxy, alkoxy, cycloalkyloxy, aralkyloxy such as benzyloxy, alkanoyloxy, alkylthio, alkoxycarbonyl, aminocarbonyl, alkylaminocarbonyl, dialkylaminocarbonyl, carboxy, aryl such as phenyl, aryloxy such as phenoxy, arylthio such as phenylthio, heteroaryloxy such as pyridyloxy, heteroarylthio such as pyridylthio, and $NR^4R^5$, whereby
$R^4$ and $R^5$ are selected independently from each other from hydrogen, alkyl, alkenyl, alkinyl, aralkyl such as benzyl and aryl such as phenyl;
$R^2$ is selected from hydrogen, halogen, cyano, alkyl, trifluoromethyl, hydroxy, alkoxy and aralkyloxy such as benzyloxy;
$R^3$ is selected from hydrogen, alkyl, alkenyl, alkinyl, hydroxy, alkoxy and aryloxy such as benzyloxy;
k is 0 or 1,
A is selected from
alkylene, optionally substituted one to three-fold by alkyl, hydroxy, alkoxy, fluorine, or aryl such as phenyl, alkylene, wherein a methylene unit is isosterically replaced by O, S, $NR^6$, CO, SO or $SO_2$, whereby, with the exception of CO, the isosteric substitution cannot be adjacent to the amine group and $R^6$ is selected from hydrogen, alkyl, alkenyl, acyl or alkanesulfonyl;
1,2-cyclopropylene;
alkenylene, optionally substituted once or twice by alkyl, hydroxy, alkoxy, fluorine, cyano or aryl such as phenyl;
alkadienylene, optionally substituted once or twice by alkyl, fluorine, cyano or aryl such as phenyl;
hexatrienylene, optionally substituted by $C_1$–$C_3$-alkyl, fluorine, cyano or phenyl; as well as
ethinylene;
D is selected from
alkylene, optionally substituted once or twice by alkyl, hydroxy, or alkoxy;
alkenylene, optionally substituted once or twice by alkyl, hydroxy, or alkoxy; alkinylene, optionally substituted once or twice by alkyl, hydroxy, or alkoxy; as well as
alkylene, alkenylene or alkinylene, in which one to three methylene units is isosterically replaced by O, S, $NR^7$, CO, SO or $SO_2$, wherein $R^7$ is synonymous with $R^6$, but is selected independently thereof;

E is a cyclic imide of the general formula

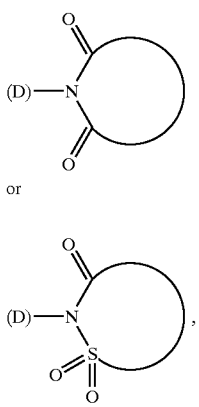

(E 1)

or (E 2)

bound over the imide nitrogen atom to D selected from
saturated or unsaturated monocyclic imides with 5 to 7 ring atoms, whereby, aside from the essential imide nitrogen atom, one or two further hetero-atoms can be present selected from N and/or S and/or O in this imide ring;
saturated, unsaturated or aromatic anellated bi-, tri- or tetracyclic imides with 8 to 18 ring atoms of which, aside from the essential imide nitrogen atom, one to three further hetero-atoms can be present selected from N and/or S and/or O;
saturated or unsaturated, bridged bi-, tri- tetra- or pentacyclic imides with 8 to 22 ring atoms of which, aside from the essential imide nitrogen atom, one to three further hetero-atoms can be present selected from N and/or S and/or O;
saturated or unsaturated spirccyclic imides, optionally anellated once or twice and with a total of 9 to 23 ring atoms of which, aside from the essential imide nitrogen atom, one to three further hetero-atoms can be present selected from N and/or S and/or O;
whereby these cyclic imides can be substituted by one to five of the same or different groups selected independently from each other from
halogen, cyano, alkyl, alkylidene, trifluoromethyl, cycloalkyl, cycloalkylidene, phenylalkyl, phenylalkylidene, diphenylalkyl, diphenylalkylidene, triphenylmethyl, aryl such as phenyl, hydroxy, hydroxyalkyl, alkoxy, alkoxy entirely or partially substituted by fluorine, aralkyloxy such as benzyloxy, aryloxy such as phenoxy, naphthyloxy, mercapto, alkylthio, arylthio such as phenylthio or naphthylthio, heteroarylthio such as pyridylthio, alkanesulfonyl, arylsulfonyl such as phenylsulfonyl or naphthylsulfonyl, heteroarylsulfonyl such as pyridylsulfonyl, sulfo, carboxy, carboxyalkyl, carboxyalkenyl, alkoxycarbonyl, aralkyloxycarbonyl such as benzyloxycarbonyl, nitro, amino, aminoalkyl, mono-alkylamino, di-(alkyl)amino, arylamino such as phenylamino, arylalkylamino such as phenylalkylamino, heteroarylamino such as pyridylamino,
saturated or unsaturated, four- to seven-membered heterocycles which can contain one or two hetero-atoms selected from N and/or S and/or O and are either bound directly or bound over a methylene group or a methine group, monocyclic aromatic five- or six-membered heterocycles which can contain one to three hetero-atoms selected from N and/or S and/or O and are either bound directly or bound over a methylene group or a methine group,
anellated bicyclic, aromatic or partial hydrated carbocyclic ring systems with 8 to 12 ring atoms which are either bound directly or bound over a methylene or a methine group,
anellated bicyclic aromatic or partially hydrated heterocyclic ring systems with 8 to 12 ring atoms, whereby one to three ring atoms can be selected from N and/or S and/or O and are either bound directly or bound over a methylene or a methine group,
and whereby aryl and heteroaryl residues as substituents of the cyclic imides can be substituted themselves by one to three of the same or different groups selected from
halogen, cyano, alkyl, trifluoromethyl, cycloalkyl, aralkyl such as benzyl, aryl such as phenyl, hydroxy, hydroxyalkyl, alkoxy, alkoxy entirely or partially substituted by fluorine, aralkyloxy such as benzyloxy, aryloxy such as phenoxy, mercapto, alkylthio, arylthio such as phenylthio, carboxy, carboxyalkyl, carboxyalkenyl, alkoxycarbonyl, aralkyloxycarbonyl such as benzyloxycarbonyl, nitro, amino, aminoalkyl, mono-alkylamino, di-(alkyl)amino and, for two adjacent residues, methylenedioxy;
their cis- and trans-isomers, E- and Z-isomers of the above defined compounds, especially in the case that A is a cyclopropane ring or D contains one or more double bonds, including the enantiomers, diastereomers and other isomers of the above defined compounds, as well as their racemic and/or non-racemic mixtures, as well as the pure endo- and/or exo-isomers of the above defined compounds in the case that the imide ring system is bicyclic, as well as their mixtures;
their tautomeric compounds in the optimal case that E contains a heterocyclic aromatic ring with simultaneous substitution by free hydroxy, mercapto or amino groups; and the
acid addition salts of the above defined compounds including their hydrates and solvates.

Also, in a preferred embodiment of the invention the compounds of formula (VII), disclosed in WO 99/31064, are not encompassed by the present invention:

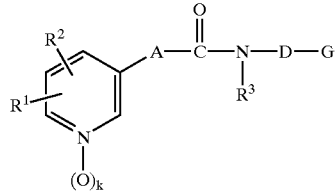

(VII)

wherein the substituents have the following meanings:
$R^1$ is selected from hydrogen, halogen, cyano, alkyl, alkenyl, alkinyl, fluoroalkyl such as trifluoromethyl, cycloalkyl, hydroxyalkyl, hydroxy, alkoxy, cycloalkyloxy, aralkyloxy such as benzyloxy, alkanoyloxy, alkylthio, alkoxycarbonyl, aminocarbonyl, alkylaminocarbonyl, dialkylaminocarbonyl, carboxy, aryl such as phenyl, aryloxy such as phenoxy, arylthio such as phenylthio, heteroaryloxy such as pyridyloxy, heteroarylthio such as pyridylthio, and $NR^4R^5$, whereby $R^4$ and $R^5$ are selected independently of each other from hydrogen, alkyl, alkenyl, alkinyl, aralkyl such as benzyl and aryl such as phenyl;

$R^2$ is selected from hydrogen, halogen, cyano, alkyl, fluoroalkyl such as trifluoromethyl, hydroxy, alkoxy and aralkyloxy such as benzyloxy;

$R^3$ is selected from hydrogen, alkyl, alkenyl, alkinyl, hydroxy, alkoxy and aralkyloxy such as benzyloxy;

k is the number 0 or 1,

A is selected from
- alkylene, optionally substituted one to three-fold by alkyl, hydroxy, alkoxy, fluorine, or aryl such as phenyl;
- alkylene, wherein a methylene unit is isosterically replaced by O, S, $NR^6$, CO, SO or $SO_2$, whereby, with the exception of CO, the isosteric substitution cannot be adjacent to the amide group and $R^6$ is hydrogen, alkyl, alkenyl, acyl or alkanesulfonyl;
- 1,2-cyclopropylene;
- alkenylene, optionally substituted once or twice by alkyl, hydroxy, alkoxy, fluorine, cyano or aryl such as phenyl;
- alkadienylene, optionally substituted once or twice by alkyl, fluorine, cyano or aryl such as phenyl;
- 1,3,5-hexatrienylene, optionally substituted by alkyl, fluorine, cyano or aryl such as phenyl; and
- ethinylene D is selected from
- alkylene with at least 3 carbon atoms, optionally substituted once or twice by alkyl, hydroxy, alkoxy or aryl such as phenyl;
- alkenylene with at least 3 carbon atoms or alkadienylene with at least 5 carbon atoms, optionally substituted once or twice by alkyl, hydroxy, alkoxy or aryl such as phenyl;
- alkinylene with at least 3 carbon atoms or alkeninylene, with at least 5 carbon atoms, optionally substituted once or twice by alkyl, hydroxy, alkoxy or aryl such as phenyl; as well as
- alkylene, alkenylene or alkinylene each with at least 3 carbon atoms, wherein one to three methylene units, with the exception of the (G)-terminal methylene group, are isosterically replaced by O, S, $NR^7$, CO, SO or $SO_2$, whereby $R^7$ is synonymous with $R^6$, but is selected independently thereof;

G is selected from G1, G2, G3, G4, G5 or G6 with the proviso that G must contain at least one aromatic ring, whereby $G^1$ has the meaning $$-(CR^9R^{10})_m-R^8 \quad (G1)$$

whereby
m is the number 0 or 1, and
$R^8$ is selected from
- aralkyl such as benzyl or diphenylmethyl, aryl such as phenyl;
- monocyclic aromatic five- or six-membered heterocycles, which can contain one to three hetero-atoms selected from N and/or S and/or O and are either bound directly or over a methylene group;
- anellated bi- and tricyclic aromatic or partially hydrated carbocyclic ring systems with 8 to 18 ring atoms and at least one aromatic ring, whereby the linkage can occur either over an aromatic or a hydrated ring and either directly or over a methylene group;
- anellated bi- and tricyclic aromatic or partially hydrated heterocyclic ring systems with 8 to 18 ring atoms and at least one aromatic ring, whereby one to three ring atoms can be selected from N and/or S and/or O and the linkage can occur either over an aromatic or a hydrated ring and either directly or over a ethylene group;

$R^9$ is selected from
- hydrogen, alkyl, alkenyl, alkinyl, cycloalkyl; aralkyl such as benzyl, aryl such as phenyl; saturated or unsaturated, four- to six-membered heterocycles, which can contain one or two hetero-atoms selected from N and/or S and/or O;
- monocyclic aromatic five- or seven-membered heterocycles, which can contain one to three hetero-atoms selected from N and/or S and/or O and are either bound directly or over a methylene group;
- anellated bi- and tricyclic aromatic or partially hydrated carbocyclic ring systems with 8 to 18 ring atoms and at least one aromatic ring, whereby the linkage can occur either over an aromatic or a hydrated ring and either directly or over a methylene group;
- anellated bi- and tricyclic aromatic or partially hydrated heterocyclic ring systems with 8 to 18 ring atoms and at least one aromatic ring, whereby one to three ring atoms can be selected from N and/or S and/or O and the linkage can occur either over an aromatic or a hydrated ring and either directly or over a methylene group;

$R^{10}$ is synonymous with $R^9$, but can be selected independently thereof, and also hydroxy;

$G^2$ is the grouping $$=CR^8R^9 \quad (G2)$$

which is bound to D by means of a double bond,
wherein $R^8$ and $R^9$ have the above meaning, or whereby this grouping $=CR^8R^9$ can also be a ring system bound over the carbon atom, selected from
- anellated bi- and tricyclic partially hydrated carbocyclic ring systems with 8 to 18 ring atoms and at least one aromatic ring;
- anellated bi- and tricyclic partially hydrated heterocyclic ring systems with 8 to 18 ring atoms and at least one aromatic ring, whereby one to three ring atoms can be selected from N and/or S and/or O;

$G^3$ is selected from $$-X-(CH_2)_n-(CR^9R^{10})_m-R^8 \quad (G3a)$$

or $$-NR^8R^9 \quad (G3b)$$

whereby m and the substituents $R^8$, $R^9$ and $R^{10}$ can have above meanings, and
n is the number 0, 1 or 2,
X has the meaning $NR^{11}$, O or S, whereby
$R^{11}$ has the same meaning as $R^4$, but is selected independently thereof, or the grouping $-NR^8R^9$ can also be a nitrogen heterocycle bound over the nitrogen atom, selected from anellated bi- and tricyclic aromatic or partially hydrated heterocyclic ring systems with 8 to 18 ring atoms and at least one aromatic ring, which, aside from the essential nitrogen atom, can contain 1 or 2 further hetero-atoms selected from N and/or S and/or O; and G$^4$ is selected from

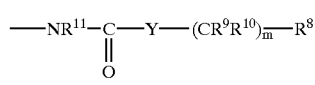
(G4a)

or

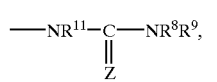
(G4b)

with the proviso that the structural element D—G cannot contain a total of more than 1 amide grouping (>N—CO—C← or →C—CO—N<), whereby m and the substituents R$^8$, R$^9$, R$^{10}$, R$^{11}$ and the grouping NR$^8$R$^9$ can have the above defined meanings with the proviso that the residues

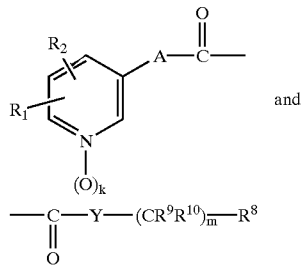

and cannot be identical, and

Y is selected from methylene, ethylene, ethenylene, cycloalkylene or represent a bond, and Z has the meaning O or S;

G$^5$ has the meaning

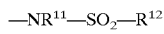 (G5)

wherein

R$^{11}$ has the above meaning, and

R$^{12}$ is selected from alkyl, aryl such as phenyl; monocyclic aromatic five- or six-membered heterocycles, which can contain one to three hetero-atoms selected from N and/or S and/or O;

anellated bi- and tricyclic aromatic or partially hydrated carbocyclic ring systems with 8 to 18 ring atoms and at least one aromatic ring, whereby the linkage can occur either over an aromatic or a hydrated ring;

anellated bi- and tricyclic aromatic or partially hydrated heterocyclic ring systems with 8 to 18 ring atoms and at least one aromatic ring, whereby one to three ring atoms can be selected from N and/or S and/or O and the linkage can occur either over an aromatic or a hydrated ring;

G$^6$ is selected from

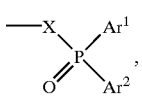
(G6)

wherein

X can have the above meanings and

Ar$^1$ and Ar$^2$ are selected independently from each other from aryl such as phenyl or naphthyl as well as heteroaryl such as pyridyl;

and whereby aromatic ring systems in the substituents R$^1$, R$^2$, R$^3$, R$^4$, R$^5$, R$^8$, R$^9$, R$^{10}$, R$^{11}$, R$^{12}$, Ar$^1$ and Ar$^2$ and/or in ring systems =CR$^8$R$^9$ and —NR$^8$R$^9$ can be substituted independently from each other by one to three of the same or different groups selected from halogen, cyano, alkyl, fluoroalkyl such as trifluoromethyl, cycloalkyl, aralkyl such as benzyl, aryl such as phenyl, hydroxy, hydroxyalkyl, alkoxy, alkoxy entirely or partially substituted by fluorine, aralkyloxy such as benzyloxy, aryloxy such as phenoxy, mercapto, alkylthio, arylthio such as phenylthio, sulfo, carboxy, carboxyalkyl, carboxyalkenyl, alkoxycarbonyl, aralkyloxycarbonyl such as benzyloxycarbonyl, nitro, amino, aminoalkyl, mono-alkylamino, di-(alkyl)amino and, for two adjacent residues on the aromatic ring, methylenedioxy and whereby alkyl and cycloalkyl residues in the group G can be substituted by one or two of the same or different residues selected from hydroxy, carboxy, alkoxycarbonyl, aralkyloxycarbonyl such as benzyloxycarbonyl, amino, mono-alkylamino and di-(alkyl)amino;

the cis- and trans-isomers as well as E- and Z-isomers of the above defined compounds, especially in the case that A is a cyclopropane ring or D contains one or more double bonds, including the enantiomers, diastereomers and other isomers of the above defined compounds, optionally in pure form or as their racemic and/or non-racemic mixtures;

the tautomers of the above defined compounds, in the optional case that G represents a heterocyclic aromatic ring or one which simultaneously contains substitutions by free hydroxy, mercapto or amino groups; as well as the corresponding acid addition salts of the above defined compounds including their hydrates and solvates.

Before the advent of the present invention, no compounds have been described which exclusively inhibit the NAD(P) synthesis at this step. Accordingly, this mode of action is entirely different from that proposed by Morton (Nature 181:540–543, 1958) for tumor therapy. He suggested to inhibit the enzyme NAD pyrophosphorylase, but the inhibition of this enzyme would block the synthesis of NAD(P) from all three precursors (niacinamide, niacin and tryptophan, compare FIG. 1). It was absolutely surprising that the inhibition of NAD synthesis at the step of the formation of niacinamide mononucleotide in the niacinamide pathway was sufficient to kill most tumor cells. The present compounds are the first tools to investigate the importance of the niacinamide pathway in tumor cells. The present inventors found that most tumor cells, for example, HepG2 (liver carcinoma), U-87 MG (glioblastoma, astrocytoma), U-373 MG (glioblastoma, astrocytoma), Caki-1 (renal clear cell carcinoma), KG-1a (myelogenic leukaemia), HL-60 (promyelocytic leukaemia), A549 (lung carcinoma), MCF-7 M1 (breast carcinoma), PC3 (prostate carcinoma), can utilize only on the niacinamide pathway of NAD(P) synthesis. From this finding it is concluded that these compounds can be used for the therapy of the corresponding cancers (e.g. breast, prostate, lung, colon, cervix, ovary, skin, CNS, bladder, pancreas and leukemia and lymphoma). The above cell lines are known and commercially available.

Furthermore, blocking only the niacinamide pathway protects those cells which can also use niacin or tryptophan as precursor from the effect of the compounds. These cells are typical healthy somatic cells, e.g. liver cells, Kupffer cells, lung epithelial cells, renal epithelial cells, lymphocytes, colon epithelial cells or dermal fibroblasts. In regard to side effects, this essentially sole inhibition of the niacinamide pathway is of enormous advantage for the treatment of cancer.

For the detection of specific inhibitors of niacinamide mononucleotide formation the following screening assay is especially useful which comprises the following steps: incubating cultured cells selected from HepG2 cells, U-87 MG cells, MCF-7 M1 cells, Caki-1 cells, HL-60 cells, PC3 cells, U-373 MG cells, A549 cells and KG-1a cells in the presence of [$^{14}$C]niacinamide and a compound to be tested for its activity to inhibit the cellular formation of niacinamide mononucleotide; effecting lysis of the cells; isolating and separating the [$^{14}$C]-labeled compounds and measuring the amount of formed labeled niacinamide mononucleotide, NAD and NADP. More concretely, cultured cells are seeded in a defined density in culture dishes, followed by incubation in the presence of a test compound and by the addition of [$^{14}$C]niacinamide for about 0.1 to 6 hrs. The cells are then lysed with perchloric acid and the resulting extract is neutralized. Finally, the [$^{14}$C]-labeled compounds are separated by thin-layer chromatography on cellulose matrices followed by UV detection and autoradiography. Non-radioactive niacinamide derivatives are used as standards. This assay allows simple and effective screening and selection of the compounds according to the invention.

The present invention also provides a method for assaying the dependency of a given cell type on niacinamide as a precursor for NAD synthesis. This method allows to determine which (malignant) cell types are particularly sensitive to the compounds according to the invention and can be helpful to develop a suitable regimen for combatting various tumors. Accordingly, such an assay would comprise incubating cells to be tested in the presence of a compound according to the invention in a medium containing only niacinamide as a NAD synthesis precursor; and performing a cytotoxicity assay after the incubation period. Such a cytotoxicity assay could, for example, be the "high density cell test" described in the experimental part.

For the detection of specific inhibitors of niacinamide phosphoribosyltransferase (NAPRT) the assay referred to in the Examples Section as Nicotinamide Reversibility Assay can be used in a preferred embodiment of the invention.

For the detection of specific inhibitors of niacinamide phosphoribosyltransferase (NAPRT) the assay referred to in the Examples Section as Niacinamide Phosphoribosyltransferase (NAPRT) Assay can be used in a preferred embodiment of the invention.

EXAMPLES

Material and Methods

Reagents

Trypsin/EDTA: 0.05% (w/v) trypsin (Difco, Detroit, USA)+0.016% (w/v) EDTA (Sigma, Deisenhofen, Germany).

[$^{14}$C]Niacinamide: ARC794, American Radiolabeled Chemicals Inc., St. Louis, Mo., USA, 0.25 mCi/ml; specific activity 50 mCi/mmol.

Lysis buffer: 0.5 M perchloric acid (Merck, Darmstadt, Germany).

Neutralization reagent: 0.5 mM potassium chloride, 2.0 M potassium hydroxide, dissolved in purified water. The chemicals were obtained from Merck, Darmstadt, Germany.

TLC foils: Cellulose F, Art. 1.05565, Merck, Darmstadt, Germany Poly(ethyleneimine) Cellulose F, Art. 1.05579, Merck Darmstadt, Germany.

TLC solvents: 0.05 M lithium chloride or 3 parts 1 M ammonium acetate pH 5.0+7 parts ethanol (Merck, Darmstadt, Germany).

Standards: 10 to 20 mg/ml solutions of the following niacinamide derivatives were prepared: niacin, niacinamide, niacin mononucleotide (dNAM), niacinamide mononucleotide (NAM), niacin adenine dinucleotide (dNAD), niacinamide adenine dinucleotide (NAD), niacinamide adenine dinucleotide phosphate (NADP). All standards were purchased from Sigma, Deisenhofen, Germany.

TCA solution: 500 g trichloro-acetic acid, dissolved in $H_2O$ ad 2 l (25% w/v).

10 mM Tris buffer: 121.1 mg trishydroxymethyl aminomethane (Sigma, Deisenhofen, Germany) dissolved in 100 ml $H_2O$, titrated to pH=10.4 with NaOH.

SRB solution: 400 mg sulforhodamine B (Sigma, Deisenhofen, Germany), dissolved in 100 ml of 1% (v/v) acetic acid.

Test compounds: K22-compounds were synthesized by the department of chemistry at Klinge Pharma GmbH, Munich, Germany. Stock solutions: a 10 mM solution was prepared in dimethylsulfoxide (DMSO) and stored at −18° C.; further dilution steps were done in ethanol.

Cell line: The human-derived tumor cell line HepG2 (liver carcinoma) was obtained from the American Type Culture Collection (ATCC), Rockville, Md., USA.

Growth Medium

Richter's Improved Minimal Essential Medium, Zinc Option (IMEM-ZO), was purchased from Gibco BRL, Life Technologies (Eggenstein, Germany) (Richter, A., Sanford, K. K. and Evans, V. J. (1972), J. Natl. Cancer Inst. 49: 1705–1712). The medium powder was dissolved in deionized water, the pH titrated to 7.2 with HCl/NaOH and sterilized by filtration. The medium was supplemented with 5% or 10% fetal calf serum (FCS), PAN Systems GmbH, Aidenbach, Germany; 100 μg/l insulin (Boehringer, Mannheim, Germany) and 50,000 IU/l penicillin+50 mg/l streptomycin (Sigma, Deisenhofen, Germany).

HEPES-buffered IMEM-ZO: This medium was used for incubation of HepG2 cells with the radiolabeled precursor. In contrast to the above-described Richter's IMEM-ZO, it did not contain niacinamide, $NaHCO_3$ and FCS. This medium was sp.cifically prepared by Gibco BRL, Life Technologies (Eggenstein, Germany). The medium was buffered with 20 mM HEPES (Sigma, Deisenhofen, Germany) and the pH was adjusted to 7.2. The medium was sterilized by filtration.

Determination of NAD(P) Synthesis from [$^{14}$C]niacinamide Cell Culture

The cells were detached from 75 $cm^2$ flasks by removing the growth medium and adding 3 ml trypsin/EDTA solution to each flask. After about 5 minutes incubation at 37° C., when the cells were detached from the surface of the dishes, trypsinization was stopped by adding 3 ml Richter's IMEM-ZO medium containing 10% FCS. The cells were suspended by repeated pipetting. For predilution, an aliquot of 20 µl was added to 10 ml Casyton isotonic solution (No. 043-90037P, Scharfe System, Reutlingen, Germany) using a Sysmex Auto Dilutor Type AD-260 (Toa, Medical Electronics Co. Ltd., Kobe, Japan). The cell number was determined by electronic cell volume measurements and counting with a CASY 1 Cell Counter+Analyzer System, Model TTC (Scharfe System, Reutlingen, Germany) equipped with a 60 µm capillary. Following dilution in IMEM-ZO containing 10% FCS, the cells were finally seeded at a density of $4 \times 10^6/10$ ml per sample in Ø 10 cm tissue culture dishes (Greiner, Frickenhausen, Germany) and incubated at 37° C. in a humidified atmosphere of 5% $CO_2$ in air.

After one day, when the cells were adherent to the dishes, the cultures were replenished with IMEM-ZO containing 5% FCS plus the test compound or the vehicle. Concentrations of organic solvents in the medium after addition of the test compound did not exceed 0.1% in any case. The cells were then incubated at 37° C. for 17 hours in a humidified atmosphere of 5% $CO_2$ in air. This preincubation period is not necessary to achieve a distinct inhibitory action of the compounds and can be shortened for example to 2 or 0 hours. After this period of time, the medium was again discarded and 4 ml HEPES-buffered IMEM-ZO containing the test compound or the vehicle and 0.5 µCi/ml [$^{14}$C] niacinamide were added to each culture for an additional 5 hours at 37° C. and 100% humidity. Just before the cells were harvested with a cell scraper and transferred to 15 ml polypropylene tubes, a 100 µl aliquot was taken from the incubation medium to determine the radioactivity. The culture dishes were rinsed with 4 ml saline supplemented with 10 mM niacinamide and the solutions were pooled with the respective cell suspension. The cells were collected by centrifugation at 250 g for 5 minutes at 4° C.

Extraction of Pyridine Nucleotides

Pyridine nucleotides were extracted by a modification of the procedure of Chatterjee et al. (Chatterjee, S., Hirschler, N. V., Petzold, S. J., Berger, S. J. and Berger, N. A. (1989) Mutant Cells Defective in Poly(ADP-ribose) Synthesis due to Stable Alterations in Enzyme Activity or Substrate Availability. Exp. Cell Res. 184: 1–15). Briefly, each cell pellet was suspended in 200 µl ice-cold 0.5 M perchloric acid and incubated on ice for 20 minutes. After this period of time, the acid extracts were neutralized by adding 55 µl of a KCl/KOH solution and centrifuged at 2500 g for 10 minutes at 4° C. Supernatants were collected and stored at −20° C. until separation by chromatography. A 10 µl aliquot was taken from each supernatant to measure the total amount of radioactivity in the cell extract.

Thin-layer Chromatography

The $^{14}$C-labeled components of the cell extracts were separated and identified using two thin-layer chromatography (TLC) systems. 2 µl of each cell extract was transferred to a cellulose and a poly(ethyleneimine) (PEI) cellulose TLC foil using a DC-Probenautomat III (CAMAG, Muttenz, Switzerland) The cellulose foils were developed using 1 M $NH_4$ acetate:ethanol (3:7) as solvent (Pinder, S., Clark, J. B. and Greenbaum, A. L. (1971) The Assay of Intermediates and Enzymes Involved in the Synthesis of the Nicotinamide Nucleotides in Mammalian Tissues. Methods in Enzymology. Academic Press, New York. Vol. XVIIIB pp. 20–46). The PEI cellulose plates were developed with 0.05 M lithium chloride (Barton, R. A., Schulman, A., Jacobson, E. L. and Jacobson, M. K. (1977) Chromatographic Separation of Pyridine and Adenine Nucleotides on Thin Layers of Poly(ethyleneimine) Cellulose. J. Chromatogr. 130: 145–150).

The chromatograms were run with added non-radioactive standards of NAD, NADP, NAM, dNAM, dNAD, niacin and niacinamide, and the spots were identified by UV absorption. See Table 6 for $R_F$ values. Results are expressed as mean±S.D. For autoradiography, the chromatograms were exposed to an imaging plate BAS-IIIs (Fuji Photo Film Co., Ltd., Japan) in a hypercassette (Amersham Buchler GmbH & Co. KG, Braunschweig, Germany) for at least two days. To avoid high background activity, the cassette was placed in a lead box. After exposure, the imaging plate was read in the bio-imaging analyzer FUJIFILM BAS-1500 (Fuji Photo Film Co., Ltd., Japan). The portion of each [$^{14}$C]-labeled component in the cell extracts was determined as percentage of total radioactivity with the software TINA 2.0 (raytest Isotopenmessgerate GmbH, Straubenhardt, Germany).

TABLE 6

$R_F$-values for NAD, NADP, NAM, dNAM, dNAD, niacin and niacinamide

| | Matrix/Solvent | |
|---|---|---|
| Standard | PEI cellulose/LiCl | Cellulose/$NH_4$ acetate:ethanol |
| Niacin | 0.45 ± 0.03 (n = 12) | 0.73 ± 0.04 (n = 14) |
| Niacinamide | 0.77 ± 0.01 (n = 14) | 0.80 ± 0.04 (n = 14) |
| dNAM | 0.18 ± 0.04 (n = 4) | 0.19 ± 0.04 (n = 4) |
| NAM | 0.52 ± 0.08 (n = 3) | 0.19 ± 0.05 (n = 3) |
| dNAD | 0.07 ± 0.01 (n = 10) | 0.09 ± 0.01 (n = 10) |
| NAD | 0.37 ± 0.02 (n = 14) | 0.11 ± 0.02 (n = 14) |
| NADP | 0.02 ± 0.01 (n = 13) | 0.04 ± 0.01 (n = 13) |

The amount of $^{14}$C-labeled derivatives was calculated by multiplying the total radioactivity of the cell extract by the percentage recovered in each derivative. The results of the assay as shown in Table 3a and Table 3b above are expressed as pmol [$^{14}$C]NAD(P) per $10^6$ cells and as pmol [$^{14}$C]NAD (P) per mg protein. Cell count and cellular protein were determined from cultures prepared in parallel without radioactive precursors.

Protein Determination

The cellular protein was determined with the bicinchoninic acid (BCA) assay purchased from Pierce, Rockford, Ill., USA, according to the manufacturer's instructions. The color of the samples produced from the reaction was measured spectrophotometrically (COBAS FARA II, F. Hoffmann-La Roche AG, Basel, Switzerland).

Determination of Cell Growth Under High-density Conditions (SRB Assay)

Cell Culture

The cells were detached from 75 cm$^2$ flasks by removing the growth medium and adding 3 ml trypsin/EDTA solution to each well. After 5 minutes incubation at 37° C., when the cells were detached from the surface of the dishes, trypsinization was stopped by adding 3 ml Richter's IMEM-ZO medium containing 10% FCS. The cells were suspended by repeated pipetting. For predilution an aliquot of 20 µl was added to 10 ml Casyton isotonic solution (No. 043-90037P, Scharfe System, Reutlingen, Germany) using a Sysmex Auto Dilutor Type AD-260 (Toa, Medical Electronics Co. Ltd., Kobe, Japan). The cell number was determined by electronic cell volume measurements and counting with a CASY 1 Cell Counter+Analyser System, Model TTC (Scharfe System, Reutlingen, Germany) equipped with a 60 µm capillary. Following dilution in growth medium the cells were finally seeded at a density of 200,000 cells per ml and well in 24-well culture dishes (Greiner, Frickenhausen, Germany) Additionally, three negative control wells were incubated in growth medium without any cells.

After one day, when the cells were adherent to the dishes, the cultures were replenished with fresh medium containing 5% FCS plus different concentrations of the test compounds or the vehicle. Triplicate samples were prepared from each concentration and the cells were incubated at 37° C. in a humidified atmosphere of 5% $CO_2$ in air. Concentration of organic solvents in the medium after addition of test compounds did not exceed 0.1% in any cases.

Sulforhodamine B Assay (SRB)

Determination of cell growth was performed by unspecific protein staining with sulforhodamine B according to Skehan et al. (Skehan, P. et al. (1990) New Colorimetric Cytotoxicity Assay for Anticancer-Drug Screening. J. Natl. Cancer Inst. 82: 1107–1112).

The drug incubation period of the cells was stopped by the addition of 250 µl of ice cold TCA solution into the growth medium. After one hour incubation in the refrigerator, the supernatant was discarded, the dishes were rinsed five times with deionized water, dried at room temperature (RT) and finally stored in the refrigerator until staining. 0.5 ml of SRB solution was pipetted into each well and incubated at room temperature for 30 minutes; thereafter, the staining solution was decanted, the dishes were washed four times with 1% (v/v) acetic acid and dried again at RT. SRB stain unspecifically bound to protein was released by adding ml of 10 mM Tris buffer per well and gentle shaking for 5 minutes. 100 µl aliquots of each well were transferred to a 96-well microtiter plate and the light extinction at 490 nm or at 515 nm wavelength was read in an ELISA-reader (Bio-Tek, Deelux, Gödensdorf, Germany). The mean value of negative control wells was subtracted from the test sample readings.

Nicotinamide Reversibility Assay

Hep G2 cells derived from a human liver carcinoma were plated at a density of 20,000 cells/ml in 12-well plastic dishes. Cultivation occurred in Richters IMEM-ZO nutrient medium with 5% fetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test compounds and where applicable of the nicotinamide. For the individual concentrations and the controls without test compounds, three-fold batches were done for each. Three days after the beginning of treatment, the medium was again renewed with the test compounds and where applicable the nicotinamide. After six days of compound incubation, the test was ended and the protein amount in the individual wells was determined with the sulforhodamin-B-method (according to P. Skehan et al.: *New Colorimetric Cytotoxicity Assay for Anticancer-Drug Screening. J. Natl. Cancer Inst.* 82: 1107–1112, 1990). The $IC_{50}$-values were taken from the dose-response curves and given as a comparative measurement for the activity of the test compounds.

Niacinamide Phosphoribosyltransferase (NAPRT) Assay

Material and Methods

Cell Line

The human cell line K-562 (chronic myelogenous leukaemia) is obtained from the American Type Culture Collection (ATCC CCL 243), Rockville, Md., USA. The K-562 cells are cultured in RPMI (Sigma, Deisenhofen, Germany, Product No.: R6504) containing 10% foetal calf serum (PAN Systems GmbH, Aidenbach, Germany), 2.2 g/l $NaHCO_3$ (Merck, Darmstadt, Germany), 50,000 IU/l penicillin and 50 mg/l streptomycin (Sigma).

Cell culture flasks: Two sizes of cell culture flasks are purchased from Greiner, Frickenhausen, Germany: 75 $cm^2$ (Product No.: 658 175), 182 $cm^2$ (Product No.: 660 175).

Tubes: 2 ml Eppendorf tubes (Eppendorf-Netheler-Hinz, Hamburg Germany, Product No.: 0030 120.094). 15 ml polypropylene tubes (Greiner, Product No.: 188 271). 50 ml polypropylene tubes (Greiner, Product No.: 210 270).

Centrifuges: Megafuge 1.0 (Heraeus Sepatech, Munich, Germany). Allegra 64R (Beckman Coulter, Munich, Germany).

Reagents

CMF-PBS: $Ca^{2+}$- and $Mg^{2+}$-free phosphate-buffered saline is prepared as follows: Solution A: 1 g $KH_2PO_4$ (Product No.: 4873.0250), 40 g NaCl (Product No.: 6400), 1 g KCl (Product No.: 4933) and 5.75 g $Na_2HPO_4 \times 2H_2O$ (Product No.: 6580) are dissolved in 400 ml purified water. All chemicals are obtained from Merck. Working solution: 320 ml solution A, 133.4 mg gentamycin sulfate, 606.1 mg penicillin G ad 4 l purified water. The pH is adjusted to 7.2 and the solution sterilised by filtration.

Lysis buffer: 0.01 M $NaH_2PO_4 \times H_2O$ (Merck, Product No.: 6346), pH 7.4, (MW=137.99, 1.38 g/l purified water).

Protamine sulfate: 1% w/v protamine sulfate (Sigma, Product No.: P4020), (100 mg/10 ml purified water). The solution is stored at room temperature.

The water is purified with the system Milli-Q UF Plus (Millipore, Eschborn, Germany).

Method

The K-562 cells are grown in RPMI supplemented with 10% FCS at 37° C. and 100% humidity in a 5% $CO_2$ atmosphere up to a density of $2 \times 10^6$ cells per ml. Under these conditions, the cells grow logarithmically with a generation time of 24 hours. The cells are harvested by aspiration and centrifugation (250×g, 10 min, RT). Thereafter, the cells are washed at least 3 times by repeated centrifugation (250×g, 10 min, RT) and resuspension in CMF-PBS. After counting the cell suspension in a haematocytometer, the cells are spun into a tight pellet (390×g, 10⁻ min, RT) and the supernatant is carefully drawn off with a Pasteur pipette. The cells are then vortexed into suspension in sufficient lysis buffer to give a final concentration of 3×10 cells per ml. The suspension is frozen at −80° C. for at least one day and thawed slowly at room temperature to break up the cells. The breakage is usually greater than 95%, as determined by trypan blue exclusion. Following centrifugation at 23,000×g for 90 min at 0° C., the clarified supernatant is recovered on ice and 70 µl of 1% protamine sulfate is added per ml of supernatant. After 15 min on ice, the cloudy suspension is centrifuged a further 30 min at 23,000×g and 0° C. The final supernatant is stored in small aliquots at −80° C. This supernatant contains about 950 to 1440 µg protein per ml. 120 to 140 µg protein per sample is used in the NAPRT assay (total assay volume: 0.5 ml).

Enzyme Assay

Materials

Heating blocks: Grant QBT 1 (RT-150° C.) with aluminium inserts for 2 ml Eppendorf tubes QB-E2 (CLF, Emersacker, Germany).

Centrifuge: Minifuge T (Heraeus Sepatech).

Tubes: 2 ml Eppendorf tubes (Eppendorf-Netheler-Hinz, Product No.: 0030 120.094). 250 µl screw neck polypropylene vials (Waters, Eschborn, Germany, Product No.: WAT094172) with caps (Product No.: WAT094174).

beta-Counter: Liquid scintillation analyser 2500 TR (Canberra-Packard, Dreieich, Germany)

Scintillation fluid: Ultima Gold MV (Canberra-Packard).

Reagents

ATP: 20 mM adenosine triphosphate (Sigma, Product No.: A7699), (MW=551.1, 110.2 mg/10 ml purified water). The solution is stored at −20° C.

PRPP: 5 mM phosphoribosylpyrophosphate (about 80%, Sigma, Product No.: P8296), (MW=390.1, 25 mg/10.25 ml purified water). The solution is stored at −70° C.

$MgCl_2$: 500 mM $MgCl_2 \times 6H_2O$ (Sigma, Product No.: M0250), (MW=203.3, 10.17 g/100 ml purified water). The solution is stored at 4° C.

Tris buffer: 250 mM TRIS-HCl pH 8.8 (Preset pH 8.6, Sigma, Product No.: T5503), (MW=129.6, 3.24 g/100 ml purified water). The solution is stored at 4° C.

[$^{14}C$]Niacinamide: 0.25 mCi/ml (American Radiolabeled Chemicals Inc., St. Louis, Mo., USA, Product No.: ARC 794, specific activity: 50 mCi/mmol) The stock solution has a concentration of $5 \times 10^{-3}$ M niacinamide and is diluted with purified water to give the desired concentration.

Niacinamide: 100 mM niacinamide (Sigma, Product No.: N0636), (MW=1221, 1.22 g/100 ml purified water). The solution is stored at −20° C.

Method

The niacinamide phosphoribosyltransferase activity is determined in a reaction solution of 0.5 ml consisting of 5 mM $MgCl_2$, 2 mM ATP, 0.5 mM PRPP, and [$^{14}C$] niacinamide ($10^{-5}$ M to $10^{-7}$ M) in 50 mM Tris buffer pH 8.8 (final concentrations in the assay). The reaction is started by adding 100 to 120 µl cell extract. After incubation for 1 hour at 37° C., the enzyme reaction is stopped by adding cold niacinamide (50 µl of a 100 mM niacinamide solution per 0.5 ml reaction mixture) and by heating on a heating block (2 min, 105° C.). The precipitate is removed by centrifugation (2,500×g, 10 min, 4° C.) and the supernatant is collected into a 250 µl polypropylene vial with screw cap and stored at −20° C. until further analysis. A 10 µl aliquot is taken from the supernatant to determine the total amount of radioactivity.

Quantification of the $^{14}C$-labeled Compounds

Materials

Automated sample DC-Probenautomat III (CAMAG, Muttenz, Switzerland).

Bio-imaging analyser: FUJIFILM BAS-1500 (Fuji Photo Film Co., Ltd., Japan).

Imaging plate: BAS-IIIs (Fuji Photo Film Co., Ltd.).

Hypercassette: (Amersham Buchler GmbH & Co. KG, Braunschweig, Germany)

TLC foils: Cellulose F 20×20 cm (Merck, Product No.: 1.05565).

TLC chambers 22×22×12 cm glass chambers (Desaga, Heidelberg, Germany).

Reagents

TLC solvent: 3 parts 1 M ammonium acetate (Sigma, Product No.: A7330) pH 5.0+7 parts ethanol absolute (Merck, Product No.: 1.00983).

Standards: 20 mg/ml solutions of the following niacinamide derivatives were prepared: niacinamide, niacinamide mononucleotide, niacinamide adenine dinucleotide, niacinamide adenine dinucleotide phosphate. All standards were purchased from Sigma.

Method

The $^{14}C$-labelled components of the reaction mixture are separated and identified using thin-layer chromatography (TLC). 5 to 7.5 µl of each sample is transferred to a cellulose TLC foil using an automated sample applicator. The cellulose foil is developed using 1 M $NH_4$ acetate:ethanol (3:7) as solvent. The chromatogram is run with added non-radioactive standards of NAD, NADP, NAM and niacinamide, and the spots were identified by UV absorption ($R_F$ values see Table 7). For autoradiography, the chromatogram is exposed to an imaging plate BAS-IIIs in a hyper-cassette for at least two days. To avoid high background activity, the cassette is placed in a lead box. After exposure, the imaging plate is read in the bio-imaging analyser FUJI-FILM BAS-1500. The portion of each $^{14}C$-labelled component in the sample is determined as percentage of total radioactivity with the software TINA 2.0 (raytest Isotopen-messgeraete GmbH, Straubenhardt, Germany) The amount of $^{14}C$-labelled derivatives is calculated by multiplying the total radioactivity of the cell extract by the percentage recovered in each derivative.

TABLE 7

| Standard | $R_F$ value |
| --- | --- |
| Niacinamide | 0.80 ± 0.04 (n = 14) |
| NAN | 0.19 ± 0.05 (n = 3) |
| NAD | 0.11 ± 0.02 (n = 14) |
| NADP | 0.04 ± 0.01 (n = 13) |

$R_F$ values of niacinamide and its derivatives.
Results are expressed as mean ± S.D.
n refers to the number of measurements.

As an alternative method for the quantification of NAM acetone precipitation according to the following description can be applied:

Elliott et al. Anal. Biochem. 107: 199–205 (1980)

After finishing the NAPRT assay, remove duplicate 50 µl samples of the reaction mix to separate 2 ml aliquots of acetone. (This procedure will stop the enzymatic reaction. Addition of cold niacinamide to the reaction mix and heating at 100° C. is not necessary any more.)

Place acetone pre-soaked 2.5 cm Whatman GF/A filters for each sample on a suction manifold.

Rinse the filter once with 2 ml acetone before passing the sample through the filter. Maintain mild suction such that the 2 ml of acetone pass through the filter in 3 to 5 sec.

Mix the sample (vortex) and pass it through the filter.

Rinse the filter twice with 2 ml aliquots of acetone.

Proceed as described above with the next sample.

Transfer the filters to empty scintillation vials and allow them to dry.

Add 15 ml of scintillation fluid and vortex the vials thoroughly.

Determine the radioactivity in a beta-counter.

References

Pinder, S., Clark, J. B. and Greenbaum, A. L. (1971) The Assay of Intermediates and Enzymes Involved in the Synthesis of the Nicotinamide Nucleotides in Mammalian Tissues. Methods in Enzymology. Academic Press, New York. Vol XVIIIB pp. 20–46

Elliott, G. C., Rechsteiner, M. C. (1982) Evidence for a Physiologically Active Niacinamide Phosphoribosyl-transferase in Cultured Human Fibroblasts. Biochem. Biophys. Res. Commun. 104: 996–1002

Abbreviations

| | |
|---|---|
| ATP | adenosine triphosphate |
| CMF-PBS | $Ca^{2+}$- and $Mg^{2+}$-free phosphate-buffered saline |
| g | gravitation force |
| Min | minutes |
| NAD | niacinamide adenine dinucleotide |
| NADP | niacinamide adenine dinucleotide phosphate |
| NAM | niacinamide mononucleotide |
| Pi, PPi | inorganic phosphate |
| PRPP | phosphoribosylpyrophosphate |
| RT | room temperature |
| TLC | thin-layer chromatography |

Therapeutic Administration Form

The production of medicaments with an amount of one or more compounds according to the invention and/or their use in the application according to the invention occurs in the customary manner by means of common pharmaceutical technology methods. For this, the active ingredients as such or in the form of their salts are processed together with suitable, pharmaceutically acceptable adjuvents and carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are among the most important systemically employed medicaments for tumor treatment as well as for other indications.

Preferably, injections are administered for the treatment of tumors. These are prepared either in the form of vials or also as so-called ready-to-use injection preparations, for example as ready-to-use syringes or single use syringes in addition to perforation bottles for multiple withdrawals. Administration of the injection preparations can occur in the form of subcutaneous (s.c.), intramuscular (i.m.), intravenous (i.v.) or intracutaneous (i.c.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired active ingredient dosage. Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemulsions and liquids based on mixed micelles, for example, based on phospholipids. As with injection preparations, infusion formulations can also be prepared in the form of concentrates to dilute. The injectable formulations can also be applied in the form of continuous infusions as in stationary as well as in out-patient therapy, for example in the form of mini-pumps.

Albumin, plasma expanders, surface active compounds, organic solvents, pH influencing compounds, complex forming compounds or polymeric compounds can be added to the parenteral medicinal forms, especially as compounds for influencing the adsorption of the active ingredients to protein or polymers or also with the aim of decreasing the adsorption of the active ingredient to materials such as injection instruments or packaging materials, for example plastic or glass.

The active ingredients can be bound to nanoparticles in the preparations for parenteral use, for example on finely dispersed particles based on poly(meth)acrylates, polyacetates, polyglycolates, polyamino acids or polyether urethanes. The parenteral formulations can also be constructively modified as depot preparations, for example on the multiple unit principle, where the active ingredients are incorporated in a most finely distributed and/or dispersed, suspended form or as crystal suspensions, or on the single unit principle, where the active ingredient is enclosed in a medicinal form, for example, a tablet or a seed which is subsequently implanted. Often, these implantations or depot medicaments in single unit and multiple unit medicinal forms consist of so-called biodegradable polymers, such as for example, polyether urethanes of lactic and glycolic acid, polyether urethanes, polyamino acids, poly(meth)acrylates or polysaccharides.

Sterilized water, pH value influencing compounds, such as for example organic and inorganic acids or bases as well as their salts, buffer compounds for setting the pH value, agents for isotonicity, such as for example sodium chloride, monosodium carbonate, glucose and fructose, tensides and/ or surface active compounds and emulsifiers, such as for example, partial fatty acid esters of polyoxyethylene sorbitan (Tween®) or for example fatty acid esters of polyoxyethylene (Cremophor®), fatty oils such as for example peanut oil, soybean oil and castor oil, synthetic fatty acid esters, such as for example ethyl oleate, isopropyl myristate and neutral oil (Miglyol®) as well as polymer adjuvents such as for example gelatin, dextrane, polyvinylpyrrolidone, organic solvent additives which increase solubility, such as for example propylene glycol, ethanol, N,N-dimethylacetamide, propylene glycol or complex forming compounds such as for example citrates and urea, preservatives, such as for example hydroxypropyl benzoate and hydroxymethyl benzoate, benzyl alcohol, anti-oxidants, such as for example sodium sulfite and stabilizers, such as for example EDTA, are suitable as adjuvents and carriers in the production of preparations for parenteral use.

In suspensions, addition of thickening agents to prevent the settling of the active ingredients from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fatty acid esters. The active ingredient can also be incorporated in liquid formulations in the form of inclusion compounds, for example with cyclodextrins. As further adjuvents, dispersion agents are also suitable. For production of lyophilisates, builders are also used, such as for example mannite, dextrane, saccharose, human albumine, lactose, PVP or gelatin varieties.

As long as the active ingredients are not incorporated in the liquid medicinal formulations in the form of a base, they are used in the form of their acid addition salts, hydrates or solvates in the preparations for parenteral use.

A further systemic application form of importance is peroral administration as tablets, hard or soft gelatin capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized active ingredients, diffusions and erosion forms based on matrices, for example by using fats, wax-like and/or polymeric compounds, or so-called reservoir systems. As a retarding agent and/or agent for controlled release, film or matrix forming compounds, such as for example ethylcellulose, hydroxypropylmethylcellulose, poly(meth)acrylate derivatives (for example Eudragit®), hydroxypropylmethylcellulose phthalate are suitable in organic solutions as well as in the form of aqueous dispersions. In this connection, so-called bio-adhesive preparations are also to be named in which the increased retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of active ingredient, are especially suitable. For purposes of a targeted release of active ingredients in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatin capsules.

Anti-stick and lubricant and separating agents, dispersion agents such as flame dispersed silicone dioxide, disintegrants, such as various starch types, PVC, cellulose esters as granulating or retarding agents, such as for example wax-like and/or polymeric compounds on the basis of Eudragit®, cellulose or Cremophor® are used as a further adjuvents for the production of compressives, such as for example tablets or hard and soft gelatin capsules as well as coated tablets and granulates.

Anti-oxidants, sweetening agents, such as for example saccharose, xylite or mannite, masking flavors, aromatics, preservatives, colorants, buffer compounds, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methylcellulose, hydroxypropylcellulose or silica, talcum powder, stearates, such as for example magnesium stearate, aluminum stearate, calcium stearate, talc, siliconized talc, stearic acid, acetyl alcohol and hydrated fats are used.

In this connection, oral therapeutic systems constructed especially on osmotic principles, such as for example GIT (gastrointestinal therapeutic system) or OROS (oral osmotic system), are also to be mentioned.

Effervescent tablets or tabs. both of which represent immediately drinkable instant medicinal forms which are quickly dissolved or suspended in water are among the perorally administratable compressives. Among the perorally administratable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspisated juices which are formulated with water before ingestion. Ion exchange resins in combination with one or more active ingredients are also to be mentioned for the production of liquid ingestable forms.

A special release form consists in the preparation of so-called floating medicinal forms, for example based on tablets or pellets which develop gas after contact with body fluids and therefore float on the surface of the gastric fluid. Furthermore, so-called electronically controlled release systems can also be formulated by which active ingredient release can be selectively adjusted to individual needs.

A further group of systemic administration and also optionally topically effective medicinal forms are represented by rectally applicable medicaments. Among these are suppositories and enema formulations. The enema formulations can be prepared based on tablets with aqueous solvents for producing this administration form. Rectal capsules can also be made available based on gelatin or other carriers.

Hardened fat, such as for example Witepsol®, Massa Estarinum®, Novata®, coconut fat, glycerol-gelatin masses, glycerol-soap-gels and polyethylene glycols are suitable as suppository bases.

For long-term application with a systematic active ingredient release up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the active ingredient in a controlled manner over longer or shorter time periods based on different layers and/or mixtures of suitable adjuvents and carriers. Aside from suitable adjuvents and carriers such as solvents and polymeric components, for example based on Eudragit®, membrane infiltration increasing compounds and/or permeation promoters, such as for example oleic acid, Azone®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations: vaginally or genitally applicable emulsions, creams, foam tablets, depot implants, ovular or transurethral administration installation solutions. For ophthalmological application, highly sterile eye ointments, solutions and/or drops or creams and emulsions are suitable.

In the same manner, corresponding otological drops, ointments or creams can be designated for application to the ear. For both of the above-mentioned applications, the adminstration of semi-solid formulations, such as for example gels based on Carbopols® or other polymer compounds such as for example polyvinylpyrrolidone and cellulose derivatives is also possible.

For customary application to the skin or also to the mucus membrane, normal emulsions, gels, ointments, creams or mixed phase and/or amphiphilic emulsion systems (oil/water-water/oil mixed phase) as well as liposomes and transfersomes can be named. Sodium algenate as a gel builder for production of a suitable foundation or cellulose derivatives, such as for example guar or xanthane gum, inorganic gel builders, such as for example aluminum hydroxides or bentonites (so-called thixotropic gel builder), polyacrylic acid derivatives, such as for example Carbopol®, polyvinylpyrrolidone, microcrystalline cellulose or carboxymethylcellulose are suitable as adjuvents and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and vaseline.

Anionic, cationic or neutral tensides can be employed as emulsifiers, for example alkalized soaps, methyl soaps, amine soaps, sulfanated compounds, cationic soaps, high fatty alcohols, partial fatty acid esters of sorbitan and polyoxyethylene sorbitan, for example lanette types, wool wax, lanolin, or other synthetic products for the production of oil/water and/or water/oil emulsions.

Hydrophilic organogels can be formulated, for example, on the basis of high molecular polyethylene glycols. These gel-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, Tris-buffer or triethanolamine are used for adjusting the pH value.

Preservatives, for example such as methyl or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base.

Powders or topically applicable powders can contain for example starch varieties such as wheat or rice starch, flame dispersed silicon dioxide or silica, which also serve as diluents, for increasing flowability as well as lubricity as well as for preventing agglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administration of the active ingredients.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated for example as active ingredient-soft pellets, as an active ingredient-pellet mixture with suitable carriers, such as for example lactose and/or glucose. For inhalation or insufflation, common applicators are suitable which are suitable for the treatment of the nose, mouth and/or pharynx. The active ingredients can also be applied by means of an ultrasonic nebulizing device. As a propellant gas for aerosol spray formulations and/or controlled dosage aerosols, tetrafluoroethane or HFC 134a and/or heptafluoropropane or HFC 227 are suitable, wherein non-fluorinated hydrocarbons or other propellants which are gaseous at normal pressure and room temperature, such as for example propane, butane or dimethyl ether can be preferred. Instead of controlled dosage aerosols, propellant-free, manual pump systems can also be used.

The propellant gas aerosols can also suitably contain surface active adjuvents, such as for example isopropyl myristate, polyoxyethylene sorbitan fatty acid ester, sorbitan trioleate, lecithins or soya lecithin.

For regional application in situ, solutions for installation, for example for transurethral administration in bladder tumors or genital tumors, or for profusion in liver tumors or other organ carcinomas are suitable.

Literature References from Table 1
1. Hunting, D., Gowans, B. Henderson, J. F. Henderson. (1985) Effects of 6-aminonicotinamide on cell growth, poly(ADP-ribose) synthesis and nucleotide metabolism. Biochem. Pharmacol. 34: 3999–4003
2. Saunders, P. P., Muhs, M. A., Arimilli, S. (1996) Mechanisms of resistence to 6-aminonicotinamide. Anticancer Res. 16: 843–848
3. Street, J. C., Alfieri, A. A., Koutcher, J. A. (1997) Quantitation of metabolic and radiobiological effects of 6-aminonicotinamide in RIF-1 tumor cells in vitro. Cancer Res. 57: 3956–3962
4. Berger, N. A., Berger, S. J., Catino, D. M., Petzold, S. J., Robins, R. K. (1985) Modulation of nicotinamide adenine dinucleotide and poly(adenosine diphosphoribose) metabolism by the synthetic "C" nucleoside analogs, tiazofurin and selenazofurin. J. Clin. Invest. 75: 702–709
5. Boulton, S., Kyle, S., Durkacz, B. W. (1997) Low nicotinamide mononucleotide adenylyltransferase activity in a tiazofurin-resistant cell line: effects on NAD metabolism and DNA repair. Br. J. Cancer. 76: 845–851
6. Hillyard, D., Rechsteiner, M. C., Olivera, B. M. (1973) Pyridine nucleotide metabolism in mammalian cells in culture. J. Cell Physiol. 82: 165–180
7. Barclay, R. K., Phillipps, M. A. (1966) Effects of 6-Diazo-5-oxo-L-norleucine and other tumor inhibitors on the biosynthesis of nicotinamide adenine dinucleotide in mice. Cancer Res. 26: 282–286
8. Althaus, F. R., Richter, Ch. (1987) ADP-ribosylation of protein of proteins. Enzymology and biological significance. Chapter 2: Poly(ADP-Ribose) biosynthesis. Springer-Verlag, Berlin: 12–37
9. Althaus, F. R., Richter, Ch. (1987) ADP-ribosylation of protein of proteins. Enzymology and biological significance. Chapter 6: Poly-ADP-Ribosylation in the recovery of mammalian cells from DNA damage. Springer-Verlag, Berlin: 66–92
10. DeVita, V. T., Hellman, S., Rosenberg, S. A. (1993) Cancer: Principles & Practice of Oncology. $4^{th}$ Edition, J. B. Lippincott Company, Philadelphia.

What is claimed is:

1. A biologically active compound effective for inhibiting cellular formation of niacinamide mononucleotide.

2. A biologically active compound according to claim 1 having an inhibitory activity on cellular NAD biosynthesis from precursor niacinamide.

3. A biologically active compound according to claim 2 wherein the biologically active compound is present at a concentrations of about 10 $\mu$M or less.

4. A biologically active compound according to claim 2 wherein inhibitory activity is at least about 50%.

5. A biologically active compound according to claim 2 wherein inhibitory activity is at least about 80%.

6. A biologically active compound according to claim 2 wherein inhibitory activity is at least about 90%.

7. A biologically active compound according to claim 1 or 2 which is an inhibitor of niacinamide phosphoribosyl transferase (NAPRT).

8. A biologically active compound according to claim 7 represented by general formula (A):

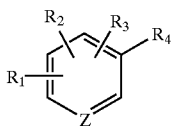

wherein

Z is CH or N,

R$_1$, R$_2$, R$_3$, and R$_4$, are selected independently from each other from carbohydrate groups, and from carbohydrate groups containing one or more of the elements selected from the group consisting of N, O, P, F, Cl, Br and I; and pharmaceutically acceptable salts thereof.

9. A biologically active compound according to claim 8, wherein R$_4$, is represented by formula (B)

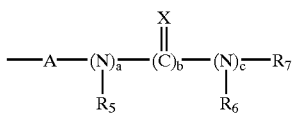

wherein

A is selected from the group consisting of a bond, a bivalent carbohydrate group and a bivalent carbohydrate group containing one or more of the elements selected from N, O, P, F, Cl, Br and I;

X is O, S or NR$_8$;

R$_5$, R$_6$, R$_7$, and R$_8$, are selected independently from each other from carbohydrate groups, and from carbohydrate groups containing one or more of the elements selected from the group consisting of N, O, P, F, Cl, Br and I;

a, b and c are 0 or 1, wherein if a and b are both 1, then c is 1.

10. Biologically active compound according to claim 9 which is selected from the group consisting of:

1-[4-(1-benzhydryl-piperidine-4-yl)-butyl]-3-pyridine-3-yl-urea;
4-benzhydryl-piperazine-1-carboxylic acid-[6-(3-pyridine-3-yl-methylureido)-hexyl]-amide;
1-(3,3-diphenylpropyl)-3-[6-(3-pyridine-3-yl-methylureido)-hexyl]-urea;
1-[5-(1-benzhydryl-piperidine-4-yl)-pentyl]-3-pyridine-3-yl-thiourea;
6-(4-benzhydryl-piperazine-1-yl)-hexanoic acid-(2-pyridine-3-yl-ethyl)-amide;
1-(6,6-diphenyl-5-hexenyl)-3-(pyridine-3-yl-methylene-amino)-thiourea;
N-(4-{1-[4-benzhydryl-piperidine-4-yl)-butyl]-piperidine-4-yl}-butyl)-3-pyridine-3-yl-propanoic acid amide;
1-[4-(1-benzhydryl-piperidine-4-yl)-butyl]-3(2-pyridine-3-yl-ethyl)-urea;
N-{2-[5-(4-benzhydryl-piperazine-1-yl-methyl)-1-methyl-1H-pyrrole-2-yl]-ethyl}-3-pyridine-3-yl-acrylamide;
1-{4-[1-(naphthalin-2-sulfonyl)-piperidine-4-yl)-butyl}-3-pyridine-3-yl-urea;
1-{4-[1-(10,11-dihydro-dibenzene[b,f]azepine-5-carbonyl)-piperidine-4-yl]-butyl}-3-pyridine-3-yl-urea;
2-amino-3-[4-hydroxy-3-(2-{4-[4(3-pyridine-3-yl-acryloyl-amino)-butyl]-piperidine-1-carbonyl}-phenylazo)-phenyl]-propanoic acid trihydrate; and N-(8,8-diphenyl-octyl)-3-pyrid-3-yl-acrylamide.

11. A pharmaceutical composition comprising a biologically active compound represented by formula (A), or a pharmaceutically acceptable salt thereof,

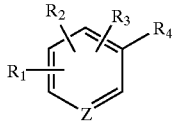

wherein

Z is CH or N,

R$_1$, R$_2$, R$_3$, and R$_4$, are selected independently from each other from carbohydrate groups, and from carbohydrate groups containing one or more of the elements selected from the group consisting of N, O, P, F, Cl, Br and I; and pharmaceutically acceptable salts thereof.

12. A pharmaceutical composition according to claim 11, wherein R$_4$, is represented by formula (B)

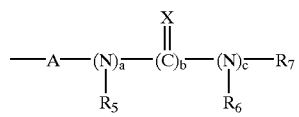

wherein

A is selected from the group consisting of a bond, a bivalent carbohydrate group and a bivalent carbohydrate group containing one or more of the elements selected from N, O, P, F, Cl, Br and I;

X is O, S or NR$_8$;

R$_5$, R$_6$, R$_7$, and R$_8$, are selected independently from each other from carbohydrate groups, and from carbohydrate groups containing one or more of the elements selected from the group consisting of N, O, P, F, Cl, Br and I;

a, b and c are 0 or 1, wherein if a and b are both 1, then c is 1.

13. A pharmaceutical composition according to claim 12 further comprising a pharmaceutically acceptable formulation additive.

14. A method for treatment of cancer in mammals comprising administering an effective amount of a biologically active compound represented by formula (A), or a pharmaceutically acceptable salt thereof,

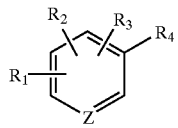

wherein

Z is CH or N,

R$_1$, R$_2$, R$_3$ , and R$_4$, are selected independently from each other from carbohydrate groups, and from carbohydrate groups containing one or more of the elements selected from the group consisting of N, O, P, F, Cl, Br and I; and pharmaceutically acceptable salts thereof.

15. A method for treatment of cancer in mammals according to claim 14, wherein R$_4$, is represented by formula (B)

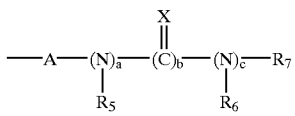

wherein
- A is selected from the group consisting of a bond, a bivalent carbohydrate group and a bivalent carbohydrate group containing one or more of the elements selected from N, O, P, F, Cl, Br and I;
- X is O, S or $NR_8$;
- $R_5$, $R_6$, $R_7$, and $R_8$, are selected independently from each other from carbohydrate groups, and from carbohydrate groups containing one or more of the elements selected from the group consisting of N, O, P, F, Cl, Br and I;
- a, b and c are 0 or 1, wherein if a and b are both 1, then c is 1.

16. A method for treatment of cancer in mammals according to claim 14 wherein the cancer is selected from the group consisting of breast, prostate, lung, colon, cervix, ovary, skin, CNS, bladder, pancreas and leukemia and lymphoma.

17. A method for treatment of cancer in mammals according to claim 14 wherein the composition is formulated for intraperitoneal, subcutaneous, oral, intravenous, rectal, buccal, intramuscular, intravaginal, topic or pulmonal administration.

18. A method for immunosuppression in mammals comprising administering an effective amount of a biologically active compound represented by formula (A), or a pharmaceutically acceptable salt thereof,

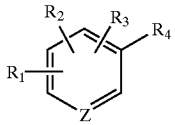

wherein
- Z is CH or N,
- $R_1$, $R_2$, $R_3$, and $R_4$, are selected independently from each other from carbohydrate groups, and from carbohydrate groups containing one or more of the elements selected from the group consisting of N, O, P, F, Cl, Br and I; and pharmaceutically acceptable salts thereof.

19. A method for immunosuppression in mammals according to claim 18, wherein $R_4$, is represented by formula (B)

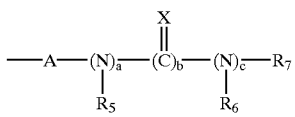

wherein
- A is selected from the group consisting of a bond, a bivalent carbohydrate group and a bivalent carbohydrate group containing one or more of the elements selected from N, O, P, F, Cl, Br and I;
- X is O, S or $NR_8$;
- $R_5$, $R_6$, $R_7$, and $R_8$, are selected independently from each other from carbohydrate groups, and from carbohydrate groups containing one or more of the elements selected from the group consisting of N, O, P, F, Cl, Br and I;
- a, b and c are 0 or 1, wherein if a and b are both 1, then c is 1.

20. A method for immunosuppression in mammals according to claim 18 wherein the composition is formulated for intraperitoneal, subcutaneous, oral, intravenous, rectal, buccal, intramuscular, intravaginal, topic or pulmonal administration.

21. A method for preparing a pharmaceutical composition effective for treatment of cancer in mammals comprising blending a biologically active compound represented by formula (A), or a pharmaceutically acceptable salt thereof, to provide a pharmaceutical composition, formula (A) having the structure

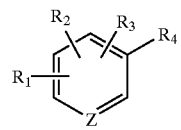

wherein
- Z is CH or N,
- $R_1$, $R_2$, $R_3$, and $R_4$, are selected independently from each other from carbohydrate groups, and from carbohydrate groups containing one or more of the elements selected from the group consisting of N, O, P, F, Cl, Br and I; and pharmaceutically acceptable salts thereof.

22. A method for preparing a pharmaceutical composition according to claim 21, wherein $R_4$, is represented by formula (B)

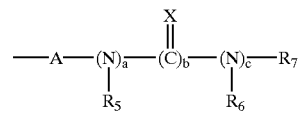

wherein
- A is selected from the group consisting of a bond, a bivalent carbohydrate group and a bivalent carbohydrate group containing one or more of the elements selected from N, O, P, F, Cl, Br and I;
- X is O, S or $NR_8$;
- $R_5$, $R_6$, $R_7$, and $R_8$, are selected independently from each other from carbohydrate groups, and from carbohydrate groups containing one or more of the elements selected from the group consisting of N, O, P, F, Cl, Br and I;
- a, b and c are 0 or 1, wherein if a and b are both 1, then c is 1.

23. A method for screening and detecting biologically active compounds effective for inhibiting cellular formation of niacinamide mononucleotide, the method comprising:
- incubating cultured cells selected from the group consisting of HepG2 cells, U-87 MG cells, MCF-7 M1 cells, Caki-1 cells, HL-60 cells, PC3 cells, U-373 MG cells, A549 cells and KG-1a cells in the presence of [$^{14}$C] niacinamide and a compound to be tested for its activity to inhibit the cellular formation of niacinamide mononucleotide;
- effecting lysis of the cells;
- isolating and separating [$^{14}$C]-labeled compounds; and
- measuring the amount of formed labeled niacinamide mononucleotide, NAD and NADP.

24. A method for determining the dependency of a cell type on niacinamide as a precursor for NAD synthesis comprising:

incubating cells to be assayed in the presence of a compound represented by general formula (A) in a medium containing only niacinamide as a NAD synthesis precursor; and performing a cytotoxicity assay after the incubation period, wherein formula (A) is

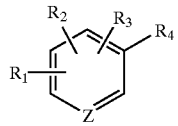

wherein
Z is CH or N,
$R_1$, $R_2$, $R_3$, and $R_4$, are selected independently from each other from carbohydrate groups, and from carbohydrate groups containing one or more of the elements selected from the group consisting of N, O, P, F, Cl, Br and I; and pharmaceutically acceptable salts thereof.

25. A method for determining the dependency of a cell type on niacinamide as a precursor for NAD synthesis according to claim 24, wherein $R_4$, is represented by formula (B)

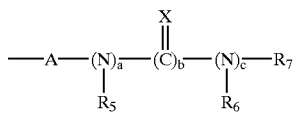

wherein
A is selected from the group consisting of a bond, a bivalent carbohydrate group and a bivalent carbohydrate group containing one or more of the elements selected from N, O, P, F, Cl, Br and I;
X is O, S or $NR_8$;
$R_5$, $R_6$, $R_7$, and $R_8$, are selected independently from each other from carbohydrate groups, and from carbohydrate groups containing one or more of the elements selected from the group consisting of N, O, P, F, Cl, Br and I;
a, b and c are 0 or 1, wherein if a and b are both 1, then c is 1.

* * * * *